(12) United States Patent
Huff et al.

(10) Patent No.: US 11,884,673 B2
(45) Date of Patent: *Jan. 30, 2024

(54) MODULATORS OF ION CHANNEL RECEPTORS AND USES THEREOF

(71) Applicant: BIONOMICS LIMITED, Thebarton (AU)

(72) Inventors: Belinda Huff, Thebarton (AU); Courtney Hollis, Mitchell Park (AU); Hamish Toop, Thebarton (AU); Nathan Kuchel, Cumberland Park (AU); Lorna Helen Mitchell, Thebarton (AU); Rajinder Singh, Torrensville (AU)

(73) Assignee: BIONOMICS LIMITED, Eastwood (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/724,601

(22) Filed: Apr. 20, 2022

(65) Prior Publication Data

US 2022/0251099 A1   Aug. 11, 2022

Related U.S. Application Data

(63) Continuation of application No. 17/056,248, filed as application No. PCT/AU2019/050472 on May 17, 2019, now Pat. No. 11,384,085.

(30) Foreign Application Priority Data

May 17, 2018 (AU) .................................. 2018901729
Aug. 20, 2018 (AU) .................................. 2018903047

(51) Int. Cl.
C07D 487/04 (2006.01)
C07D 209/24 (2006.01)
C07D 213/64 (2006.01)
C07D 471/04 (2006.01)

(52) U.S. Cl.
CPC ......... *C07D 487/04* (2013.01); *C07D 209/24* (2013.01); *C07D 213/64* (2013.01); *C07D 471/04* (2013.01)

(58) Field of Classification Search
CPC .. C07D 487/04; C07D 209/24; C07D 213/64; C07D 471/04
See application file for complete search history.

(56) References Cited

U.S. PATENT DOCUMENTS

2010/0041694 A1* 2/2010 Takaishi ................. A01N 43/42
514/367

FOREIGN PATENT DOCUMENTS

| EP | 2248423 A1 | 11/2010 |
| EP | 2937335 A1 | 10/2015 |
| WO | 2008126684 A2 | 10/2008 |
| WO | 2013131018 A1 | 9/2013 |
| WO | 2018125968 A1 | 7/2018 |

OTHER PUBLICATIONS

International Search Report and Written Opinion for PCT/AU2019/050472, dated Jul. 19, 2019, 16 pages.
Wei, C. et al., "Development of GLUT4-selective antagnoists for multiple myeloma therapy", European Journal of Medicinal Chemistry (2017), 139, 573-586.
Database CA [Online], Database accession No. 2017:1384156, XP055845330.

* cited by examiner

*Primary Examiner* — D Margaret M Seaman
(74) *Attorney, Agent, or Firm* — WARNER NORCROSS + JUDD LLP

(57) ABSTRACT

Compounds useful in the modulation of ion channel activity in cells are disclosed herein. This disclosure also relates to use of these compounds in the treatment of pain, and pharmaceutical compositions containing these compounds and methods for their preparation.

16 Claims, No Drawings

MODULATORS OF ION CHANNEL RECEPTORS AND USES THEREOF

CROSS-REFERENCE TO RELATED APPLICATIONS

This application is a continuation of U.S. application Ser. No. 17/056,248 filed on 17 Nov. 2020, which is the U.S. National Stage of International Appl. No. PCT/AU2019/050472 filed on 17 May 2019, which claims priority to and all advantages of Australian Patent Application No. 2018901729, filed on 17 May 2018 and Australian Patent Application No. 2018903047, filed on 20 Aug. 2018, the contents of which are incorporated herein by reference.

FIELD

The present invention relates to compounds useful in the modulation of ion channel activity in cells. The invention also relates to use of these compounds in the treatment of pain, and pharmaceutical compositions containing these compounds and methods for their preparation.

BACKGROUND

Voltage gated sodium channels are essential for the initiation and propagation of action potentials in excitable tissues such as muscle and nerve. Sodium channels are expressed principally in the central nervous system (CNS) and peripheral nervous system (PNS) on neurons and glial cells. To date nine subtypes have been identified: Nav1.1, Nav1.2, Nav1.3 and Nav1.6 which occur predominantly in the CNS (and less in the PNS), Nav1.4 which is specific to skeletal muscle, Nav1.5 in cardiac muscle and Nav1.7-1.9 which are distributed primarily in the peripheral nervous system in sensory neurons. Increased Nav1.x channel activity leads to nerve hyper excitability and underlies a number of pathological conditions including: epilepsy (Nav1.1 and Nav1.2), Cardiac arrhythmia (Nav1.5), myotonia (Nav1.4) and pain (Nav1.3, Nav1.7, Nav1.8 and Nav 1.9).

Pharmacological, molecular and genetic studies in both human and rodents, have identified several channels as pivotal for pain signal transmission, including Nav1.3, Nav1.7, Nav1.8, and Nav1.9. Genetic mutations in the SCN9A gene, resulting in a loss of function mutation in Nav1.7 lead to congenital insensitivity to pain (Cox et al, Nature. (2006) 444(7121) 894-898; Goldberg et al., 2007), while gain-of-function mutations cause debilitating pain syndromes such as erythromelalgia, paroxysmal extreme pain disorder, and small-fiber neuropathy (Yang et al., 2004; Fertleman et al., 2006; Faber et al., 2012). Furthermore, genetic linkages studies have shown mutations in the SCN10A gene which encodes Nav1.8 results in hyperexcitability and decreased pain thresholds in small fiber neuropathy patients, and SCN11A (Nav1.9) mutations, that produce gain-of-function effects in painful peripheral neuropathy and familial episodic pain.

Sodium channel blockers are commonly used as analgesics and are represented across three drug classes: local anaesthetics, class I antiarrhythmic and antiepileptic drugs. Although generally well tolerated, these drugs exhibit poor Nav1.x subtype selectivity and have a limited dose range due to side effects expected of interfering with CNS, cardiac and skeletal muscle sodium channel function including convulsions, ataxia, motor impairment, arrhythmias and paralysis. Despite their poor Nav1.x selectivity, these drugs are nevertheless tolerated due to their relatively low potency for Nav1.x channels in the resting (closed) state and greater potency for the inactivated state which commonly presides in Nav1.x channels mediating pain signals. In addition to this "state-dependence", the potency of local anaesthetic like compounds tends to increase with the frequency of channel opening (use-dependence) which again presides more in pathogenic states such as pain, epilepsy and ventricular fibrillation. Thus Nav1.x blockers can exhibit functional selectivity as well as subtype selectivity.

Pain has both peripheral and central components that are affected by the large network of pathways, thus peripheral neuron-targeted drugs may need to be BBB permeant to affect their actions. Nav1.7 is distributed primarily in the peripheral nervous system in dorsal root and sympathetic ganglia where it plays a role in setting the threshold for action potential firing thus controlling sensory neuron sensitivity to incoming stimuli. However, peripheral sensory neurons have terminals in the spinal cord within the blood brain barrier (BBB) and these terminals have high concentrations of Nav1.7 channels that is involved in neurotransmitter release. Hence, although Nav1.7 is distributed primarily in the peripheral nervous system, Nav1.7 inhibitors may need to be CNS penetrant, to block all aspects of Nav1.7 function.

Development of a potent and subtype selective inhibitors for any one or more of Nav1.7, Nav 1.3, Nav1.8 and Nav 1.9 are expected to provide substantial benefit over existing analgesics targeting sodium channels which lack selectivity and consequently are associated with a range of dose limiting CNS and cardiovascular side effects.

There is still a need for improved and specific therapies for the treatment of pain.

SUMMARY OF THE INVENTION

The present invention provides compounds of formula (I) and pharmaceutical compositions thereof. In certain embodiments compounds of formula (I) have utility in the treatment of pain disorders.

In a first aspect, the invention provides compounds of formula (I)

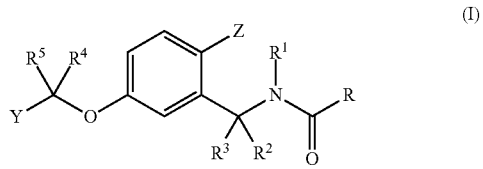

or salts, stereoisomers, solvates or prodrugs thereof, wherein
R is optionally substituted aryl, optionally substituted heterocycyl or optionally substituted heteroaryl;
$R^1$ is H or optionally substituted $C_1$-$C_4$ alkyl;
$R^2$, $R^3$, $R^4$ and $R^5$ are independently H or $C_1$-$C_4$ alkyl or $R^2$ and $R^3$, or $R^4$ and $R^5$ together form a cycloalkyl ring;
Y is selected from

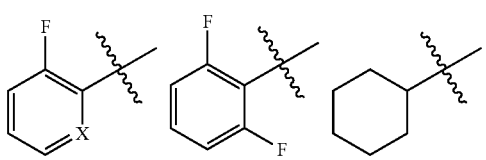

-continued

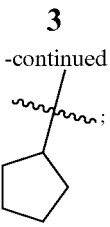

X is CH or N; and
Z is H, F or CF$_3$.

In certain embodiments, the invention provides compounds of formula (I)

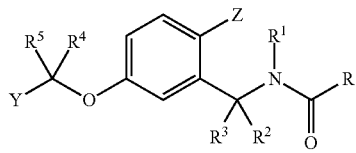

(I)

or salts, stereoisomers, solvates or prodrugs thereof, wherein
R is optionally substituted heteroaryl;
R$^1$ is H or optionally substituted C$_1$-C$_4$ alkyl;
R$^2$, R$^3$, R$^4$ and R$^5$ are independently H or C$_1$-C$_4$ alkyl, or R$^2$ and R$^3$, or R$^4$ and R$^5$ together form a cycloalkyl ring;
Y is selected from

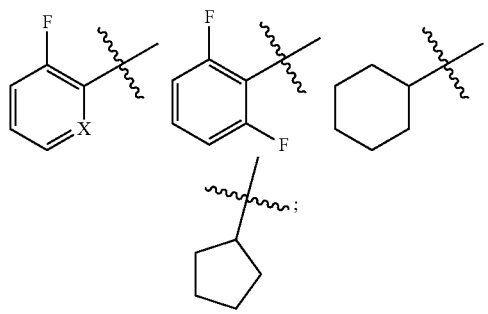

X is CH or N; and
Z is H, F or CF$_3$.

In certain embodiments, the invention provides compounds of the formula (I)

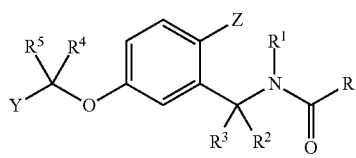

(I)

or salts, stereoisomers, solvates or prodrugs thereof, wherein
R is optionally substituted 7-12 membered heteroaryl;
R$^1$ is H or optionally substituted C$_1$-C$_4$ alkyl;
R$^2$, R$^3$, R$^4$ and R$^5$ are independently H or C$_1$-C$_4$ alkyl, or R$^2$ and R$^3$, or R$^4$ and R$^5$ together form a cycloalkyl ring;
Y is selected from

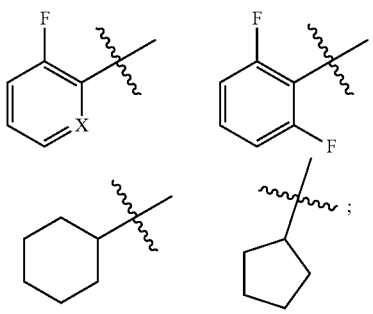

X is OH or N; and
Z is H, F or CF$_3$.

In certain embodiments, the invention provides compounds of the formula (I)

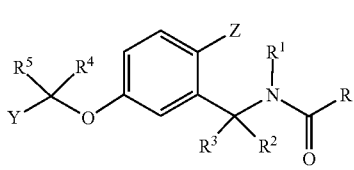

(I)

or salts, stereoisomers, solvates or prodrugs thereof, wherein
R is optionally substituted 7-12 membered heteroaryl with 2 or more N atoms;
R$^1$ is H or optionally substituted C$_1$-C$_4$ alkyl;
R$^2$, R$^3$, R$^4$ and R$^5$ are independently H or C$_1$-C$_4$ alkyl, or R$^2$ and R$^3$, or R$^4$ and R$^5$ together form a cycloalkyl ring;
Y is selected from

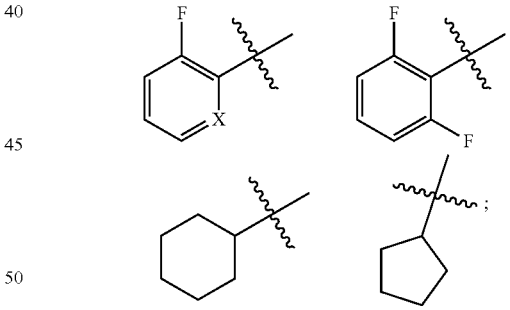

X is CH or N; and
Z is H, F or CF$_3$.

In certain embodiments, the invention provides compounds of the formula (I)

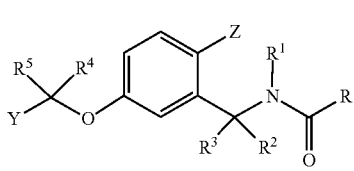

(I)

or salts, stereoisomers, solvates or prodrugs thereof, wherein
R is optionally substituted 7-12 membered heteroaryl with 2 nitrogen atoms;
$R^1$ is H or optionally substituted $C_1$-$C_4$ alkyl;
$R^2$, $R^3$, $R^4$ and $R^5$ are independently H or $C_1$-$C_4$ alkyl, or $R^2$ and $R^3$, or $R^4$ and $R^5$ together form a cycloalkyl ring;
Y is selected from

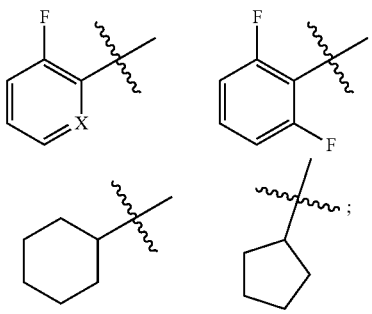

X is CH or N; and
Z is H, F or $CF_3$.

In another aspect, the present invention relates to pharmaceutical compositions comprising of at least one compound provided herein and a pharmaceutical carrier, excipient or diluent. The pharmaceutical composition can comprise one or more compounds described herein. It will be understood that compounds provided herein useful in the pharmaceutical composition and treatment methods disclosed below, can be pharmaceutically acceptable as prepared and used.

In still a further aspect, the invention provides or relates to methods for preventing, treating or ameliorating a condition from among those listed herein, particularly pain disorders (including pain associated with cancer, surgery, and bone fracture, acute pain, inflammatory pain and neuropathic pain). Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain (e.g., toothache), cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

In another aspect the invention provides methods for treating or preventing pain disorders, said method including the step of administering to a patient a compound of formula (I)

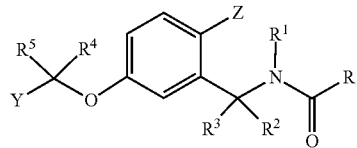

or salts, stereoisomers, solvates or prodrugs thereof,
wherein
R is optionally substituted aryl, optionally substituted heterocycyl or optionally substituted heteroaryl;
$R^1$ is H or optionally substituted $C_1$-$C_4$ alkyl;
$R^2$, $R^3$, $R^4$ and $R^5$ are independently H or $C_1$-$C_4$ alkyl or $R^2$ and $R^3$, or $R^4$ and $R^5$ together form a cycloalkyl ring;
Y is selected from

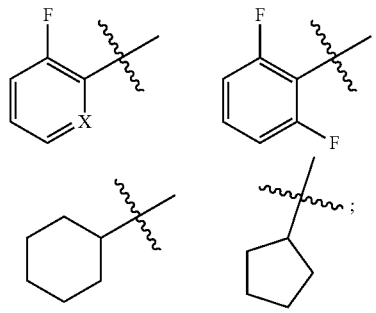

X is CH or N.

In an embodiment the invention relates to the treatment of chronic pain.
In an embodiment the invention relates to the treatment of neuropathic pain.
In an embodiment the invention relates to the treatment of inflammatory pain.
In an embodiment the invention relates to the treatment of cancer pain.
In an embodiment the invention relates to the treatment of trigeminal neuralgia, lower back pain, post-operative pain, toothache, arthritic pain (rheumatoid, osteoarthritis, gout), pain from irritable bowel, inherited erythromelalgia, paroxysmal extreme pain syndrome, post herpetic neuralgia (shingles), musculoskeletal pain, multiple sclerosis, sciatica, diabetic neuropathy, and HIV related neuropathy.
In an embodiment the invention relates to the treatment of chronic itch.
In an embodiment the invention relates to the treatment of pathological cough.
In a further embodiment the invention provides compounds to treat or prevent conditions resulting from membrane hyperexcitablility mediated by aberrant Nav channel activity for state and use-dependent Nav blockers; including: CNS conditions (for instance, epilepsy, anxiety, depression, bipolar);
Cardiac conditions (for instance, arrhythmias, atrial and ventricular fibrillation); and Muscular (for instance, restless leg, tetanus).
In addition to methods of treatment set forth above, the present invention extends to the use of any of the compounds of the invention in the preparation of medicaments that may be administered for such treatments, as well as to such compounds for the treatments disclosed and specified. In additional aspects, the present invention is directed to methods for synthesising the compounds described herein, with representative synthetic protocols and pathways described below.

Accordingly, in certain embodiments it is an aim of the present invention to provide new compounds that can modulate the activity of at least one voltage-gated sodium ion channel and thus prevent or treat any conditions that may be casually related to aberrations in such acts.

Accordingly the invention provides compounds that can treat or alleviate maladies or symptoms of same, such as pain, that may be causally related to the activation of a sodium channel.

In a further aspect the invention provides a method for treating or preventing conditions that may be casually related to the activation of at least one sodium channel, said method including the step of administering to a patient a compound of formula (I)

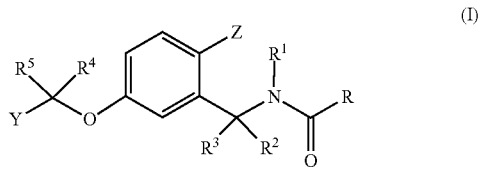

(I)

or salts, stereoisomers, solvates or prodrugs thereof, wherein

R is optionally substituted aryl, optionally substituted heterocycyl or optionally substituted heteroaryl;

$R^1$ is H or optionally substituted $C_1$-$C_4$ alkyl;

$R^2$, $R^3$, $R^4$ and $R^5$ are independently H or $C_1$-$C_4$ alkyl or $R^2$ and $R^3$, or $R^4$ and $R^5$ together form a cycloalkyl ring;

Y is selected from

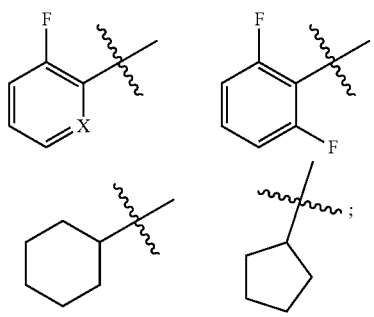

X is CH or N; and

Z is H, F or $CF_3$.

In an embodiment the compounds of the present invention display subtype and/or functional selectivity in relation to anyone one or more of Nav1.7, Nav1.3, Nav1.8 and Nav1.9 inhibition.

DETAILED DESCRIPTION

The term "alkyl" as used alone or in combination herein refers to a straight or branched chain saturated hydrocarbon group. The term "$C_{1-12}$ alkyl" refers to such a group containing from one to twelve carbon atoms and "lower alkyl" refers to $C_{1-6}$ alkyl groups containing from one to six carbon atoms, such as methyl ("Me"), ethyl ("Et"), n-propyl, isopropyl, n-butyl, isobutyl, sec-butyl, tert-butyl and the like.

The term "cycloalkyl" refers to non-aromatic, saturated non-aromatic carbocycles. The term "$C_{3-9}$ cycloalkyl", for instance, refers to such a group having from 3 to 9 carbon atoms. Examples include cyclopropyl, cyclobutyl, cyclopentyl and cyclohexyl.

The term "alkenyl" refers to a straight or branched hydrocarbon containing one or more double bonds, preferably one or two double bonds. The term "$C_{2-12}$ alkenyl", for instance, refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "cycloalkenyl" refers to cyclic alkenyl groups having a single cyclic ring or multiple condensed rings, and at least one point of internal unsaturation, preferably incorporating 4 to 11 carbon atoms. Examples of suitable cycloalkenyl groups include, for instance, cyclobut-2-enyl, cyclopent-3-enyl, cyclohex-4-enyl, cyclooct-3-enyl, indenyl and the like.

The term "alkynyl" refers to a straight or branched hydrocarbon containing one or more triple bonds, preferably one or two triple bonds. The term "$C_{2-12}$ alkynyl", for instance, refers to such a group containing from two to twelve carbon atoms. Examples include 2-propynyl and 2- or 3-butynyl.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl, benzothienyl, or benzofuranyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1,2,3 and 1,2,4-oxadiazolyls) thiazolyl, isoxazolyl, furazanyl, isothiazolyl, pyrazolyl, pyrazolinyl, pyrazolidinyl, imidazolyl, imidazolinyl, triazolyl (including 1,2,3- and 1,3,4-triazolyls), tetrazolyl, thiadiazolyl (including 1,2,3- and 1,3,4-thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like.

The term "arylalkyl" refers to carbocyclic aromatic rings or ring systems as previously described and substituted by an alkyl group, also as previously described. Unless otherwise indicated the aryl substituent is attached by the alkyl part of the substituent.

An example of an arylalkyl group is a benzyl group. Likewise the terms "aryl $C_{1-12}$ alkyl", "aryl $C_{2-12}$ alkenyl" and "aryl $C_{2-12}$ alkynyl" refer to carbocyclic aromatic rings or ring systems as previously described and substituted by a $C_{1-12}$ alkyl, $C_{2-12}$ alkenyl or $C_{2-12}$ alkynyl group, as previously described.

The terms "halo" and "halogen" refers to fluoro, chloro, bromo and iodo groups.

The term "halo alkyl" group has one or more of the hydrogen atoms on an alkyl group replaced with halogens. Notable examples are —$CF_3$ or —$CF_2H$.

The term "aryloxy" refers to an aryl group as earlier described linked to the parent structure via an oxygen linkage (—O—). A notable example is phenoxy. Similarly the term "heteroaryloxy" refers to a heteroaryl group as earlier described linked to the parent structure via an oxygen group. A notable example is a 4, 6 or 7-benzo[b]furanyloxy group.

The term "acyl" refers to groups H—C(O)—, alkyl-C(O)—, cycloalkyl-C(O)—, aryl-C(O)—, heteroaryl-C(O)— and heterocyclyl-C(O)—, where alkyl, cycloalkyl, aryl, heteroaryl and heterocyclyl are described herein.

The term "oxyacyl" refers to groups HOC(O)—, alkyl-OC(O)—, cycloalkyl-OC(O)—, aryl-OC(O)—, heteroaryl-OC(O)—, and heterocyclyl-OC(O)—, where alkyl, cycloalkyl, aryl, heteroaryl and heterocyclyl are as described herein.

The term "acylamino" refers to the group —NR"C(O)R" where each R" is independently hydrogen, alkyl, cycloalkyl, aryl, heteroaryl and heterocyclyl and where each of alkyl, cycloalkyl, aryl, heteroaryl and heterocyclyl are as described herein.

The term "aminoacylamino" refers to the group —NR"C(O)NR'R" where each R" is independently hydrogen, alkyl, cycloalkyl, aryl, heteroaryl and heterocyclyl and where each of alkyl, cycloalkyl, aryl, heteroaryl and heterocyclyl are as described herein.

The term "alkylene" refers to divalent alkyl groups preferably having from 1 to 10 carbon atoms and more preferably 1 to 6 carbon atoms. Examples of such alkylene groups include methylene (—$CH_2$—), ethylene (—$CH_2CH_2$—), and the propylene isomers (e.g., —$CH_2CH_2CH_2$— and —$CH(CH_3)CH_2$—), and the like.

The term "optionally substituted" means that a group may include one or more substituents. One or more hydrogen atoms on the group may be replaced by substituent groups independently selected from halogens (for example halo alkyl such as —$CF_3$ or —$CF_2H$), $C_{1-6}$ alkyl, $C_{2-6}$ alkenyl, $C_{2-6}$ alkynyl, —$(CH_2)_pC_{3-7}$ cycloalkyl, —$(CH_2)_pC_{4-7}$ cycloalkenyl, —$(CH_2)_p$ aryl, —$(CH_2)_p$ heterocyclyl, —$(CH_2)_p$ heteroaryl, —$C_6H_4S(O)_qC_{1-6}$ alkyl, —$C(Ph)_3$, —CN. —OR, —O—$(CH_2)_{1-6}$—R, —O—$(CH_2)_{1-6}$—OR, —OC(O)R, —C(O)R, —C(O)OR, —OC(O)NR'R", —NR'R", —NRC(O)R', —NRC(O)NR'R", —NRC(S)NR'R", —NRS(O)_2R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO_2R', —C(S)NR'R", —S(O)_qR, —SO_2NR'R", —SO_2NRC(O)R', —OS(O)_2R, —PO(OR)_2 and —NO_2;

where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —$CO_2H$, $CF_3$, CN, phenyl, $NH_2$ and —$NO_2$; or when R' and R" are attached to the same nitrogen atom, they may, together with the atom to which they are attached, form a 5 to 7 membered nitrogen containing heterocyclic ring.

A list of optional substituents includes: halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), $C_{1-6}$ alkoxy($C_{1-6}$)alkyl, $C_{3-6}$ cycloalkyl, —OH, phenyl, benzyl, phenoxy, benzyloxy, benzoyl, —$NH_2$, —NHC_{1-4} alkyl, —N($C_{1-4}$ alkyl)_2, —CN, —$NO_2$, mercapto, —P=O(OH)($NH_2$), —S(O)_2NH_2, —S(O)_2NHC_{1-4} alkyl, —S(O)_2N($C_{1-4}$ alkyl)_2, $C_{1-6}$ alkylcarbonyl, $C_{1-6}$ alkoxycarbonyl, $CO_2H$, —S(O)R''' (where R''' is lower alkyl or cycloalkyl) and —S(O)_2R''' (where R''' is lower alkyl, cycloalkyl or OH).

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, alkoxy, alkoxyalkyl, cycloalkyl, aryl, heteroaryl or heterocyclyl group, the group may itself be optionally substituted with one to six of the same or different substituents selected from halogen, $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —NHC_{1-4} alkyl, —N($C_{1-4}$ alkyl)_2, —CN, —$NO_2$, mercapto, —P=O(OH)($NH_2$), —S(O)_2NH_2, —S(O)_2NHC_{1-4} alkyl, —S(O)_2N($C_{1-4}$ alkyl)_2, $C_{1-6}$ alkylcarbonyl, $C_{1-6}$ alkoxycarbonyl, $CO_2H$, —S(O)R''' (where R''' is lower alkyl or cycloalkyl) and —S(O)_2R''' (where R''' is lower alkyl, cycloalkyl or OH).

In an embodiment, R is an optionally substituted aryl group. In another embodiment, R is an optionally substituted aryl group, wherein the aryl group is one or more fused 6-membered rings. In another embodiment, R is a monosubstituted aryl group. In another embodiment, R is an optionally substituted aryl group, wherein there is more than one substituent on the aryl group. In another embodiment, R is an unsubstituted phenyl group. In another embodiment, R is an optionally substituted phenyl group. In another embodiment, R is an optionally substituted phenyl group, wherein the substituents are selected from H, halogen, alkyl, alkenyl, alkynyl, acyl, amino, acylamino, nitro, nitrile, silyl, aryl and heteroaryl. In another embodiment, R is an optionally substituted phenyl group, wherein the substituent is a fluoro group. In another embodiment, R is an optionally substituted phenyl group, wherein the substituent is in the para position. In another embodiment, R is an optionally substituted phenyl group, wherein the substituent is in the meta position. In another embodiment, R is an optionally substituted phenyl group, wherein the substituent is in the ortho position. In a further embodiment, R is a para-fluoro-substituted phenyl group.

In an embodiment, R is an optionally substituted heterocycyl group. In another embodiment, R is an optionally substituted heterocycyl group, wherein the heterocycyl group is 5-12 membered. In another embodiment, R is an optionally substituted heterocycyl group, wherein the heterocycyl group is 6-12 membered. In another embodiment, R is an optionally substituted heterocycyl group, wherein the heterocycyl group is 6-10 membered. In another embodiment, R is an optionally substituted heterocycyl group, wherein the cycyl group is one or more fused rings. In another embodiment, R is an optionally substituted 5 membered heterocycyl group selected from, but not limited to, pyrrolidinyl, pyrazolidinyl, imidazolidinyl, tetrahydrofuranyl, 1,3-dioxolanyl, tetrahydrothiophenyl, 1,2-oxathiolanyl, 1,3-oxathiolanyl, sulfolanyl, 2,4-thiazolidinedionyl, succinimidyl, 2-oxazolidonyl, hydantoinyl and pyrrolidonyl. In another embodiment, R is an optionally substituted 6 membered heterocycyl group selected from, but not limited to, piperidinyl, piperazinyl, tetrahydropyranyl, 1,4-dioxanyl, thianyl, 1,3-dithianyl, 1,4-dithianyl, 1,3,5-trithianyl, morpholinyl and thiomorpholinyl. In another embodiment, R is an optionally substituted 7-12 membered heterocycyl group selected from, but not limited to, oxepanyl, azocanyl, thiocanyl and azonanyl. In another embodiment, R is an optionally substituted fused heterocycyl group selected from, but not limited to, pyrrolizidinyl, decahydroisoquinolinyl, decahydroquinolinyl, quinuclidinyl, 1-azaadamantanyl and 2-azaadamantanyl.

In an embodiment, R is an optionally substituted heteroaryl group. In another embodiment, R is an optionally substituted heteroaryl group, wherein the heteroaryl group is 5-membered or 6-membered. In another embodiment, R is an optionally substituted 5-membered heteroaryl group, selected from furan, pyrrole, thiophene, imidazole, pyrazole, oxazole, isoxazole and thiazole. In another embodiment, R is an optionally substituted 6-membered heteroaryl group selected from pyridine, pyrazine, pyrimidine, pyridazine and triazine. In another embodiment, R is an optionally substituted heteroaryl group, wherein the heteroaryl group is one or more fused 6-membered rings. In another embodiment, R is an optionally substituted heteroaryl group selected from quinolone, isoquinoline, quinoxaline and quinazoline. In another embodiment, R is an optionally substituted heteroaryl group, wherein the heteroaryl group has more than one heteroatom. In another embodiment, R is a monosubstituted heteroaryl group. In another embodiment, R is an optionally substituted heteroaryl group, wherein there is more than one substituent on the heteroaryl group. In another embodiment, R is an unsubstituted heteroaryl group. In another embodiment, R is an optionally substituted heteroaryl selected from, but not limited to, imidazopyridinyl, pyrazolopyrimidinyl, triazopyridinyl, pyrropyridinyl, pyrazopyridinyl, isoxazolyl, pyridinyl, pyrazolyl, imidazolyl, thiazolyl, isothiazolyl, pyrimidinyl, triazolyl, oxadiazolyl, pyrazinyl, indolyl, isoindolyl, tetrazopyridinyl and pyridonyl.

In an embodiment, R is selected from the following:

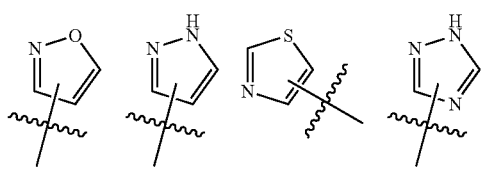

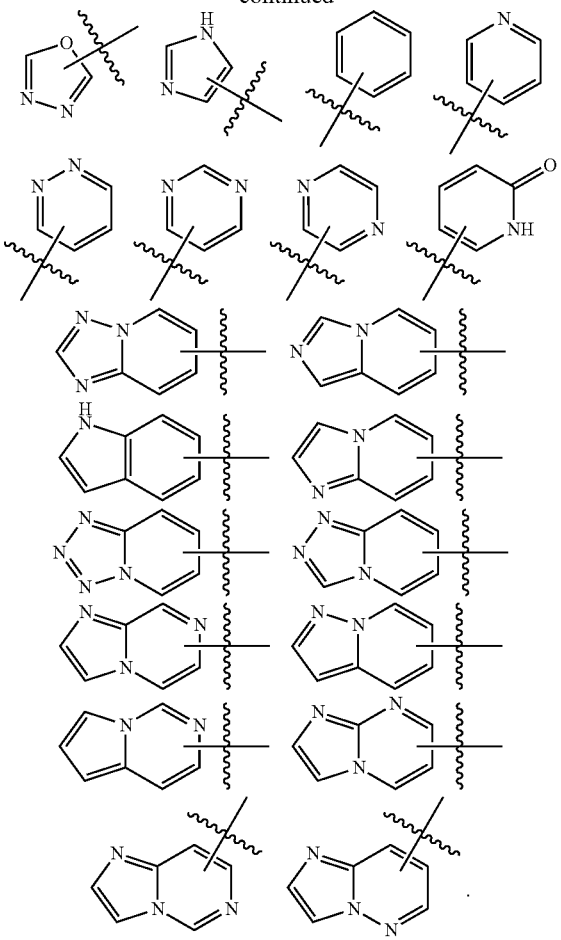

In another embodiment, R is optionally substituted 7-12 membered heteroaryl. In another embodiment, R is selected from:

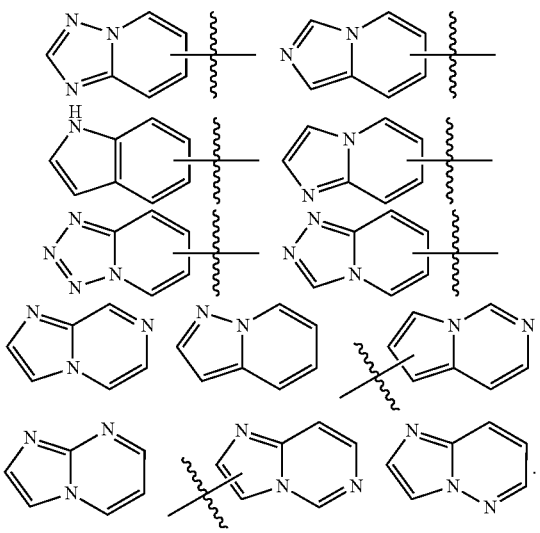

In another embodiment, R is optionally substituted 7-12 membered heteroaryl with 2 or more nitrogen atoms. In another embodiment, R is selected from:

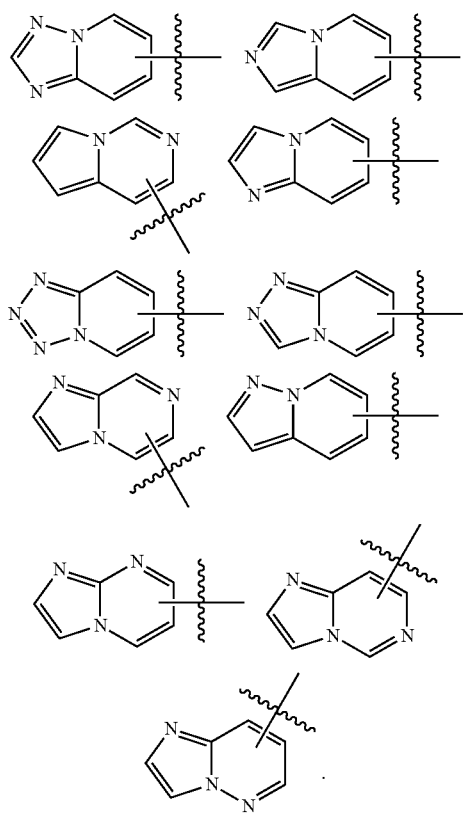
In another embodiment, R is optionally substituted 7-12 membered heteroaryl with 2 nitrogen atoms. In another embodiment, R is selected from:
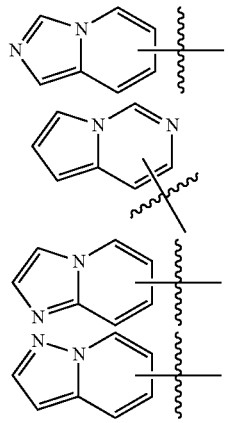
In another embodiment, R is selected from:
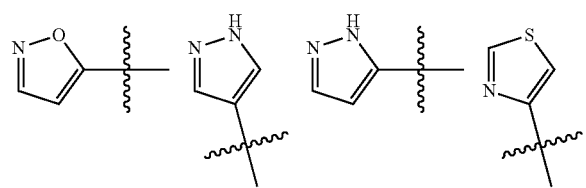
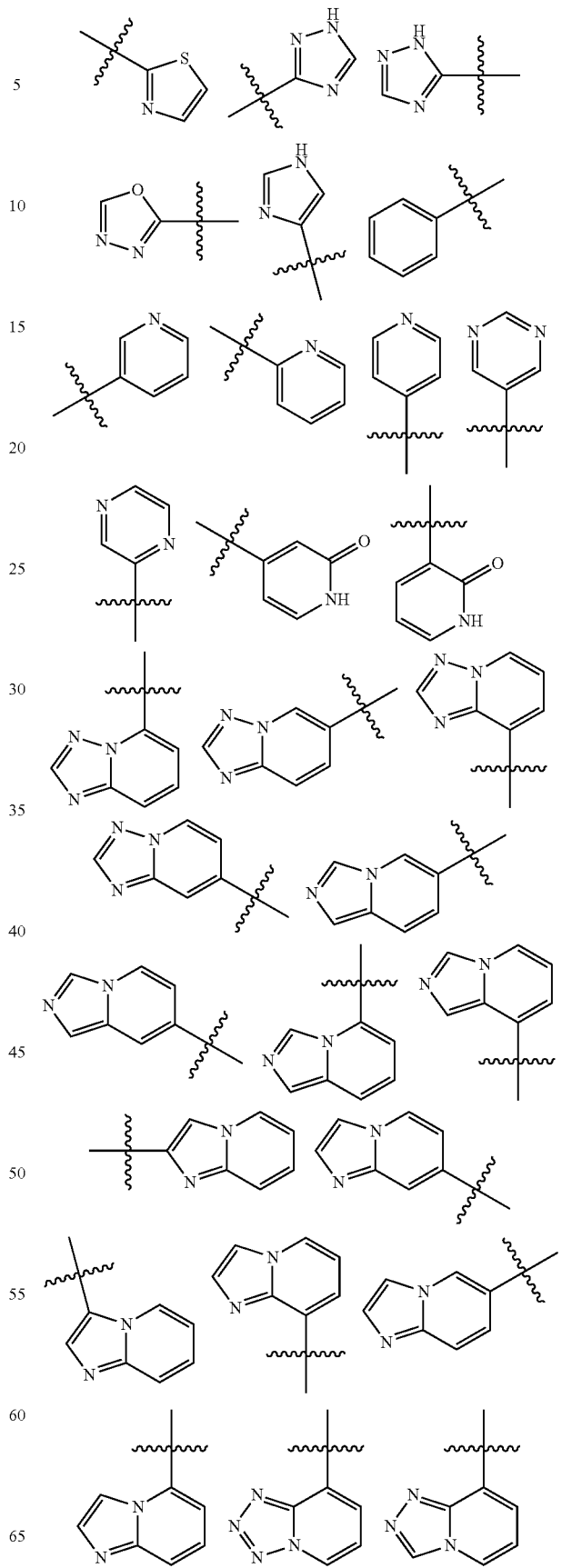

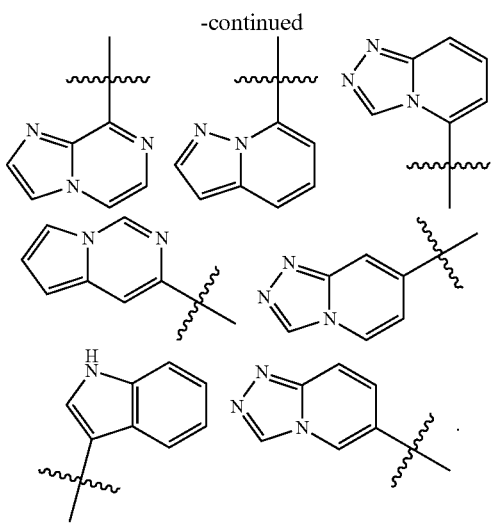

In an embodiment, $R^1$ is H or optionally substituted $C_1$-$C_4$ alkyl. In some embodiments, $R^1$ is H. In some embodiments, $R^1$ is optionally substituted $C_1$-$C_4$ alkyl. In other embodiments, $R^1$ is optionally substituted methyl, optionally substituted ethyl, optionally substituted propyl, optionally substituted isopropyl, optionally substituted butyl, optionally substituted sec-butyl, optionally substituted isobutyl or optionally substituted tert-butyl.

In an embodiment, when $R^1$ is an optionally substituted $C_1$-$C_4$ alkyl, the alkyl group has one or more substituent. In an embodiment, $R^1$ is $C_1$-$C_4$ alkyl substituted 1 to 3 times independently selected from halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, —P=O(OH)($NH_2$), —S(O)$_2NH_2$, —S(O)$_2$NH$C_{1-4}$ alkyl, —S(O)$_2$N($C_{1-4}$ alkyl)$_2$, $C_{1-6}$ alkylcarbonyl, $C_{1-6}$ alkoxycarbonyl, $CO_2$H, —S(O)R''' (where R''' is lower alkyl or cycloalkyl) and —S(O)$_2$R''' (where R''' is lower alkyl, cycloalkyl or OH). In some embodiments, $R^1$ is $C_1$-$C_4$ alkyl substituted with 1 or more groups selected from $C_1$-$C_4$ alkoxy and OH.

In some embodiments $R^1$ is

CH(OH)CH$_2$OCH$_3$.

In an embodiment, $R^2$, $R^3$, $R^4$ and $R^5$ are independently H or $C_1$-$C_4$ alkyl. In some embodiments, $R^2$, $R^3$, $R^4$ and $R^5$ are H. In some embodiments, $R^2$, $R^3$, $R^4$ and $R^5$ are independently $C_1$-$C_4$ alkyl. In another embodiment, $R^2$, $R^3$, $R^4$ and $R^5$ are independently H, methyl, ethyl, propyl, isopropyl, butyl, sec-butyl, isobutyl or tert-butyl.

In an embodiment, $R^2$ and $R^3$ together form a cycloalkyl ring. In another embodiment, $R^2$ and $R^3$ together form a $C_3$-$C_6$ cycloalkyl ring. In another embodiment, $R^2$ and $R^3$ together form a $C_3$-$C_6$ cycloalkyl ring, selected from cyclopropyl, cyclobutyl, cyclopentyl and cyclohexanyl.

In an embodiment, $R^4$ and $R^5$ together form a cycloalkyl ring. In another embodiment, $R^4$ and $R^5$ together form a $C_3$-$C_6$ cycloalkyl ring. In another embodiment, $R^4$ and $R^5$ together form a $C_3$-$C_6$ cycloalkyl ring, selected from cyclopropyl, cyclobutyl, cyclopentyl and cyclohexanyl.

In an embodiment, Y is selected from

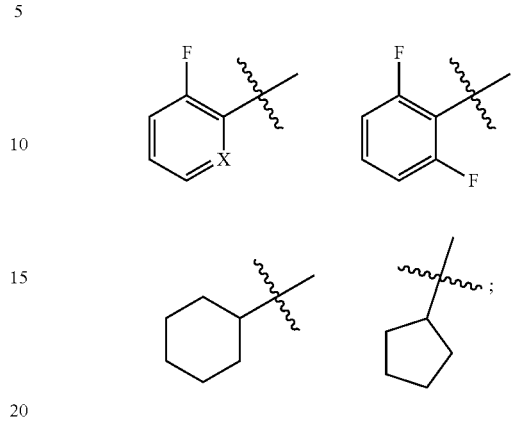

wherein X is CH or N.

In another embodiment, Y is selected from

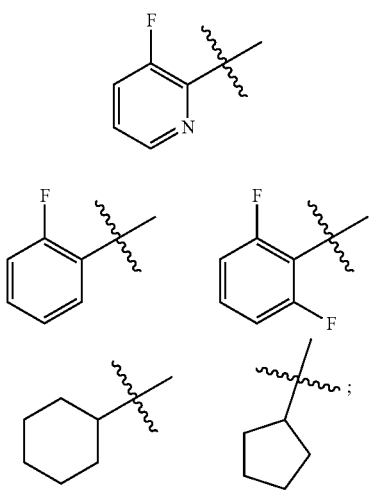

In some embodiments, Y is selected from

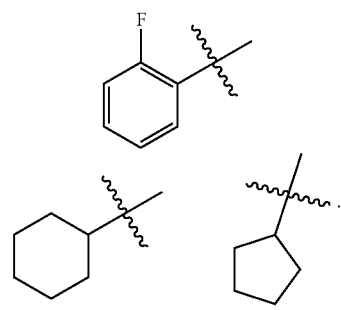

In an embodiment, Z is H, F or $CF_3$. In another embodiment, Z is H or F.

In an embodiment, R is optionally substituted heteroaryl;
$R^1$ is H or optionally substituted $C_1$-$C_4$ alkyl;
$R^2$, $R^3$, $R^4$ and $R^5$ are independently H or $C_1$-$C_4$ alkyl;

Y is selected from

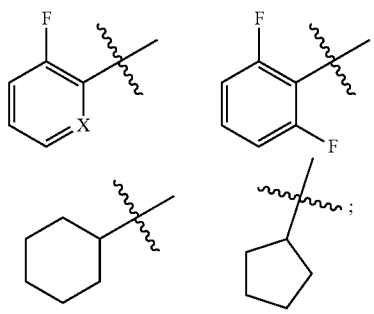

Z is selected from H, F or $CF_3$.
In an embodiment, R is optionally substituted heteroaryl;
$R^1$ is H or optionally substituted $C_1$-$C_4$ alkyl;
$R^2$, $R^3$, $R^4$ and $R^5$ are independently H or methyl;
Y is selected from

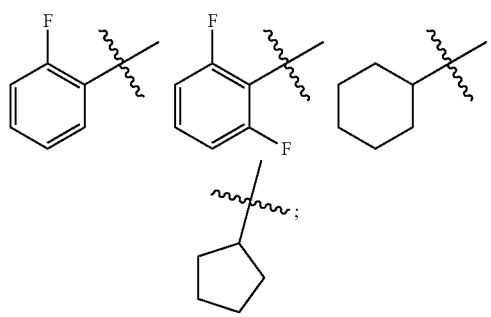

Z is selected from H, F or $CF_3$.
In an embodiment, R is optionally substituted heteroaryl;
$R^1$ is H;
$R^2$, $R^3$, $R^4$ and $R^5$ are independently H or methyl;
Y is selected from

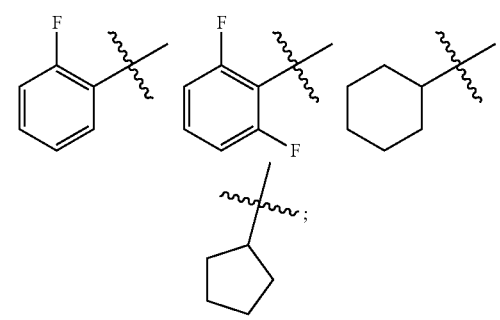

Z is selected from H, F or $CF_3$.
In an embodiment, R is optionally substituted heteroaryl;
$R^1$, $R^2$ and $R^3$ are H;
$R^4$ and $R^5$ are methyl;
Y is selected from

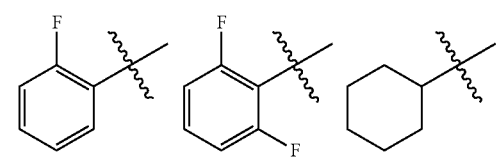

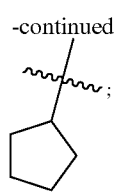

Z is selected from H, F or $CF_3$.
In an embodiment, R is optionally substituted heteroaryl;
$R^1$, $R^4$ and $R^5$ are H;
$R^2$ and $R^3$ are methyl;
Y is selected from

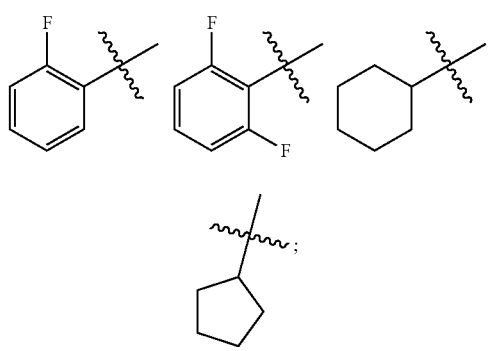

Z is selected from H, F or $CF_3$.
In an embodiment, R is optionally substituted 7-12 membered heteroaryl;
$R^1$ is H or optionally substituted $C_1$-$C_4$ alkyl;
$R^2$, $R^3$, $R^4$ and $R^5$ are independently H or methyl;
Y is selected from

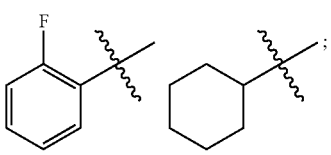

Z is selected from H or F.
In an embodiment, R is optionally substituted 7-12 membered heteroaryl with 2 or more nitrogen atoms;
$R^1$ is H or optionally substituted $C_1$-$C_4$ alkyl;
$R^2$, $R^3$, $R^4$ and $R^5$ are independently H or methyl;
Y is selected from

and
Z is selected from H or F.

In an embodiment, R is optionally substituted heteroaryl selected from

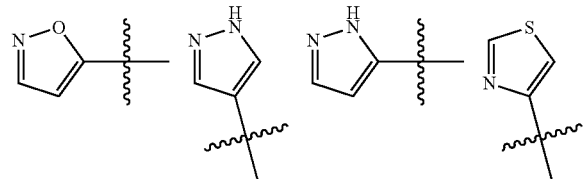
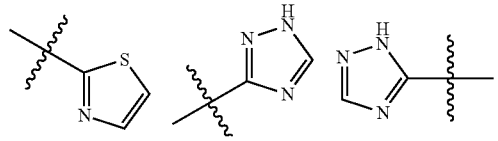
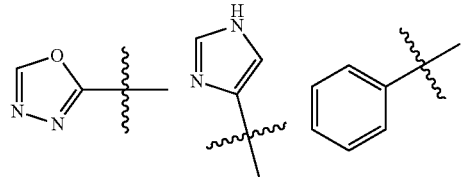
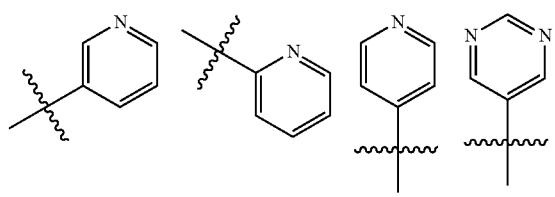
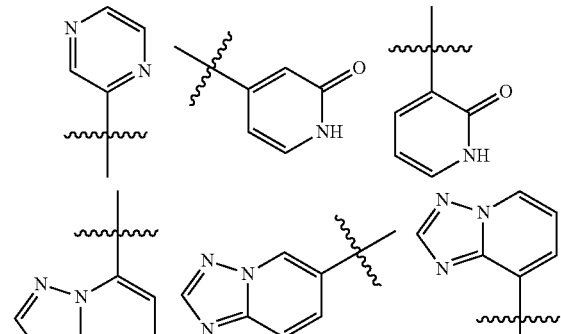
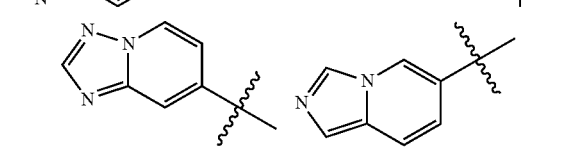
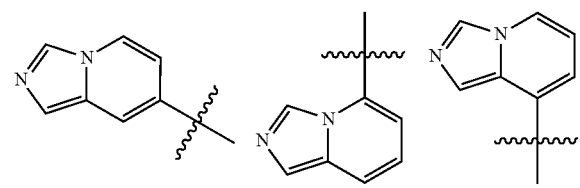
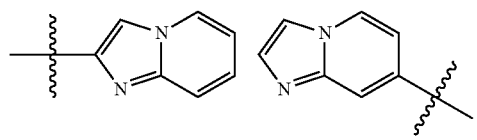

-continued

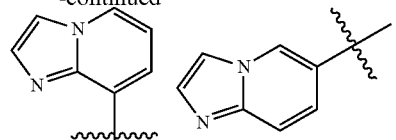
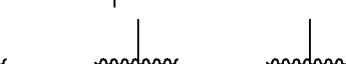
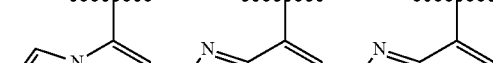
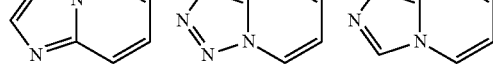
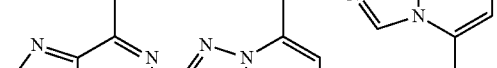
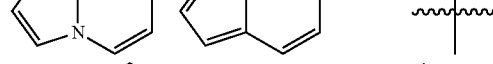
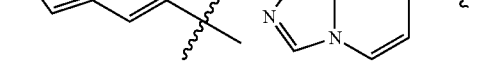
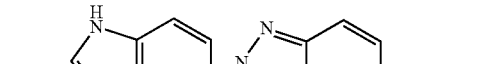

R$^1$ is H or optionally substituted C$_1$-C$_4$ alkyl;
R$^2$, R$^3$, R$^4$ and R$^5$ are independently H or C$_1$-C$_4$ alkyl, or R$^2$ and R$^3$, or R$^4$ and R$^5$ together form a cycloalkyl ring;
Y is selected from

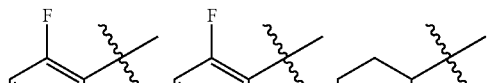
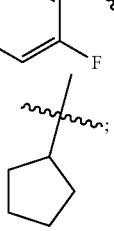

X is CH or N; and
Z is H, F or CF$_3$.

In an embodiment, R is optionally substituted heteroaryl selected from

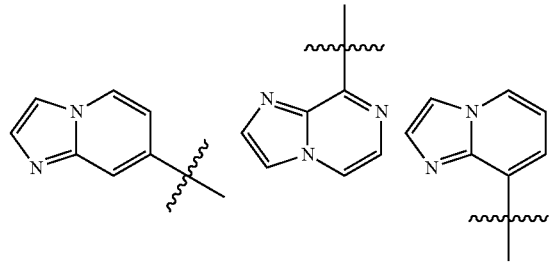

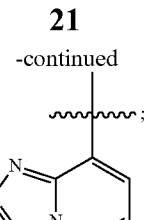

R[1] is H or optionally substituted $C_1$-$C_4$ alkyl;

R[2], R[3], R[4] and R[5] are independently H or $C_1$-$C_4$ alkyl, or R[2] and R[3], or R[4] and R[5] together form a cycloalkyl ring;

Y is selected from

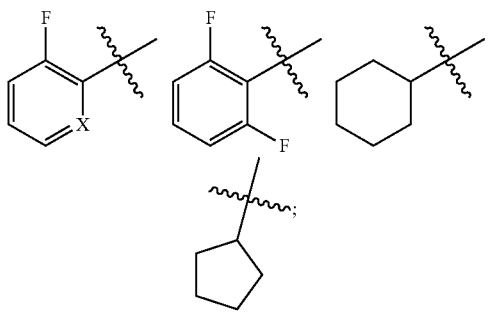

X is CH or N; and

Z is H, F or $CF_3$.

In an embodiment, R is optionally substituted heteroaryl selected from

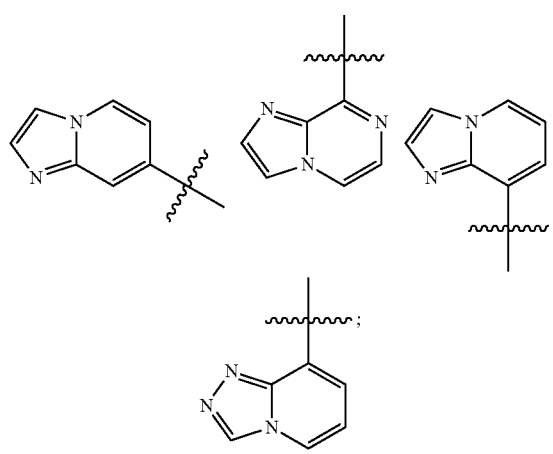

R[1] is H;

R[2], R[3], R[4] and R[5] are independently H or $C_1$-$C_4$ alkyl;

Y is selected from

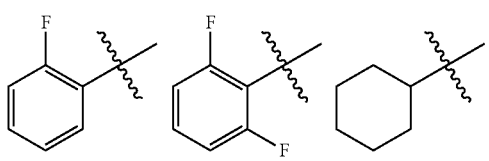

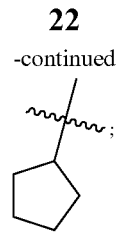

Z is selected from H, F or $CF_3$.

In an embodiment, R is optionally substituted heteroaryl selected from

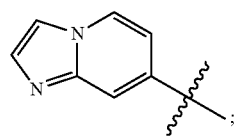 [SMILES: *c1ccn2ccnc2c1 ; ";"]

R[1] is H or optionally substituted $C_1$-$C_4$ alkyl;

R[2], R[3], R[4] and R[5] are independently H or $C_1$-$C_4$ alkyl, or R[2] and R[3], or R[4] and R[5] together form a cycloalkyl ring;

Y is selected from

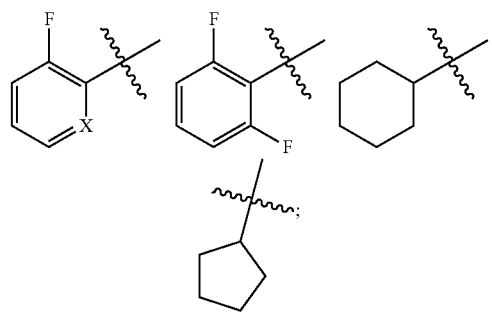

X is CH or N; and

Z is H, F or $CF_3$.

In an embodiment, R is optionally substituted heteroaryl selected from

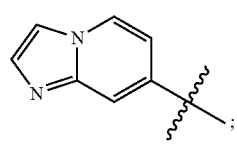

R[1] is H;

R[2], R[3], R[4] and R[5] are independently H or $C_1$-$C_4$ alkyl;

Y is selected from

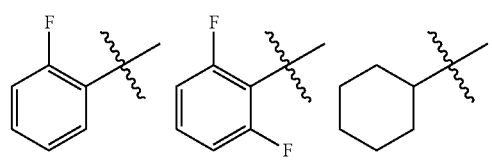

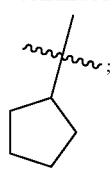
and
Z is selected from H, F or CF$_3$.
Representative examples of Compounds of Formula (I) include:
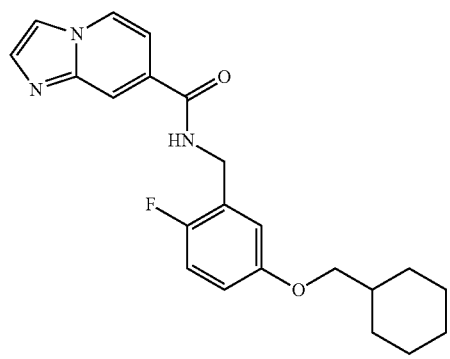
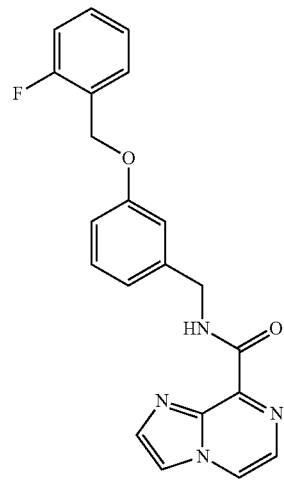
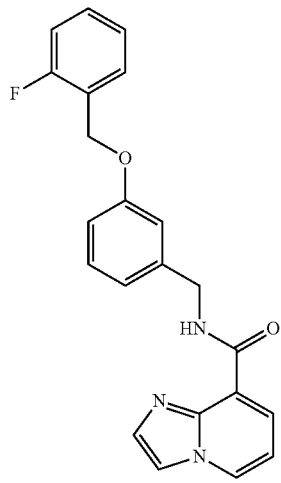
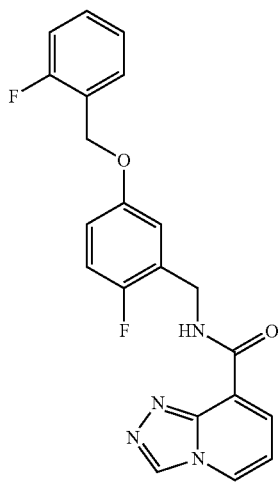
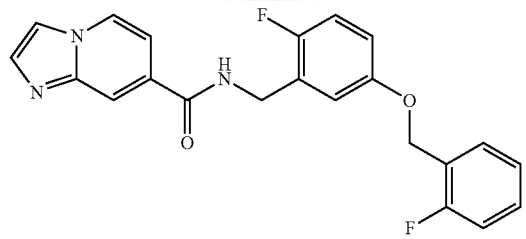
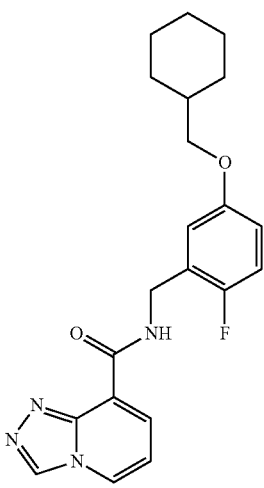
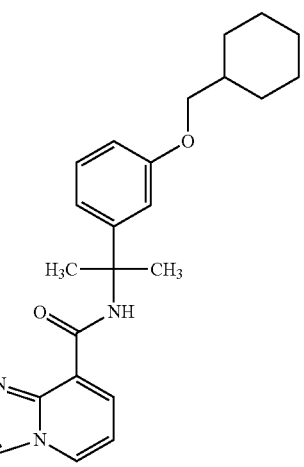
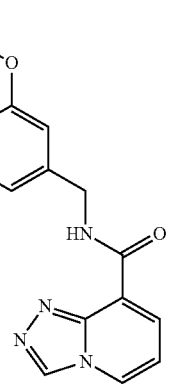

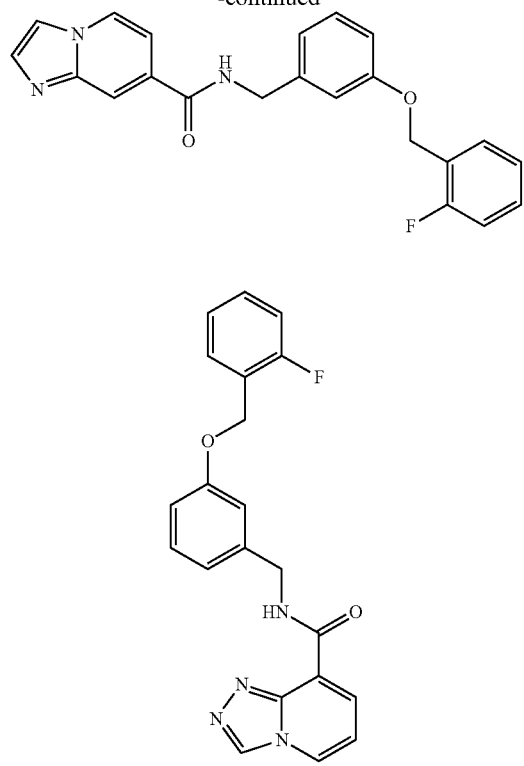
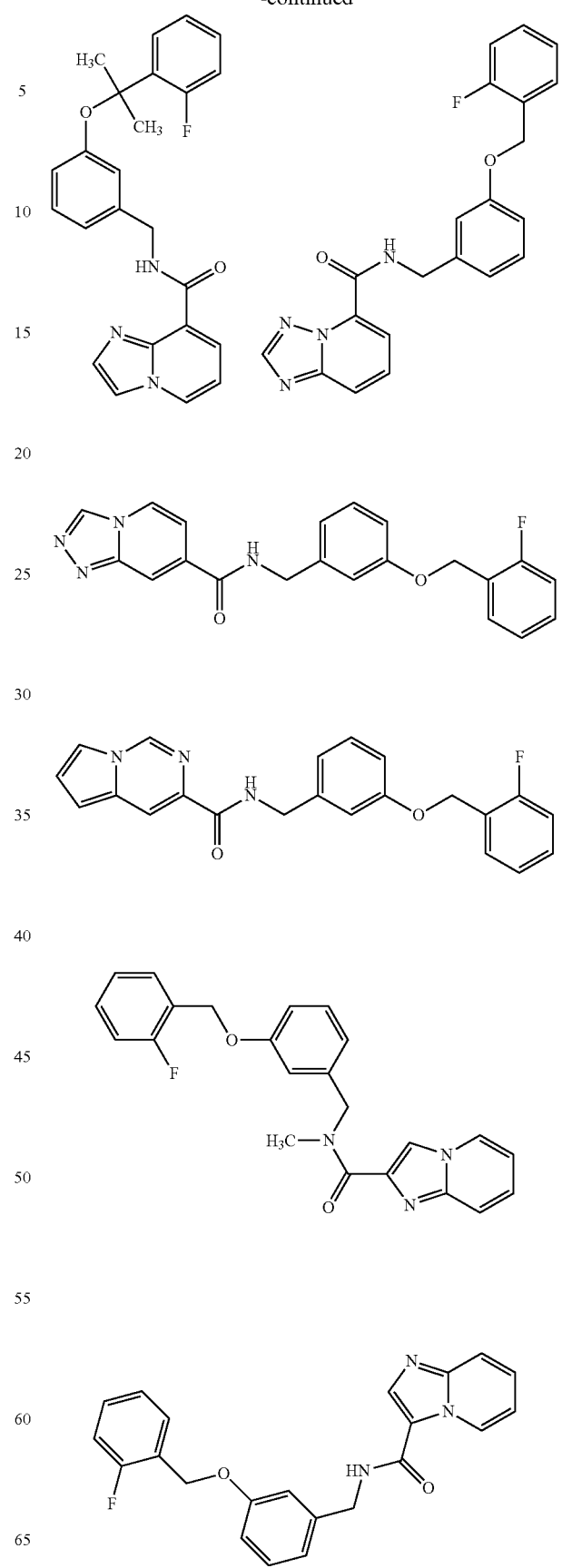

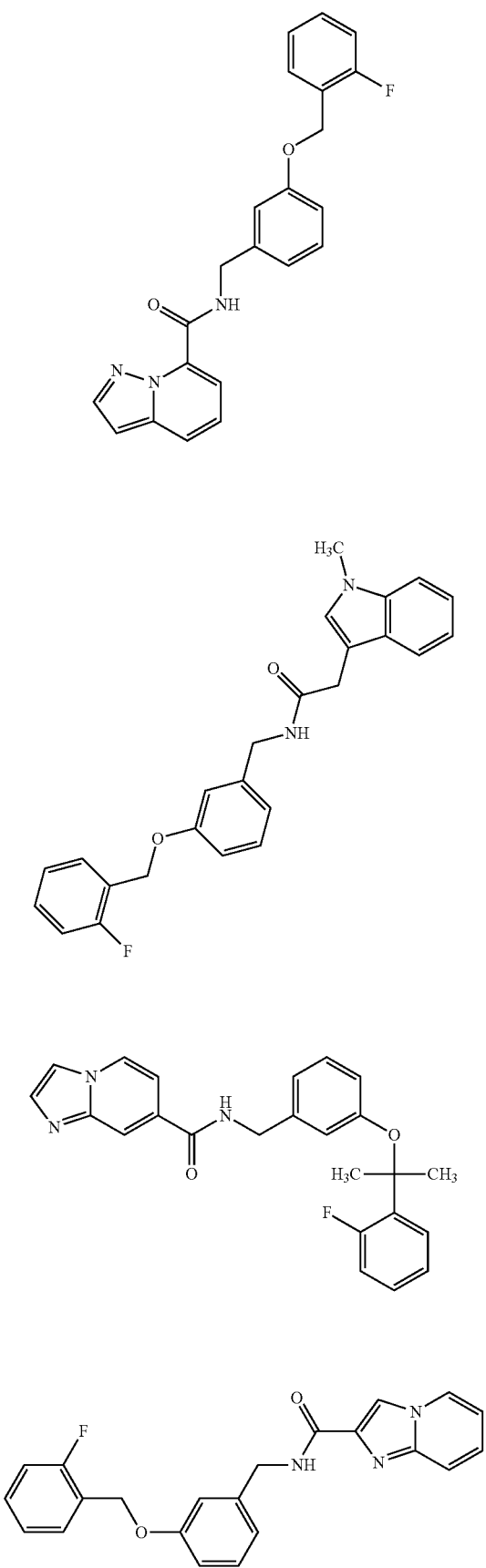

-continued
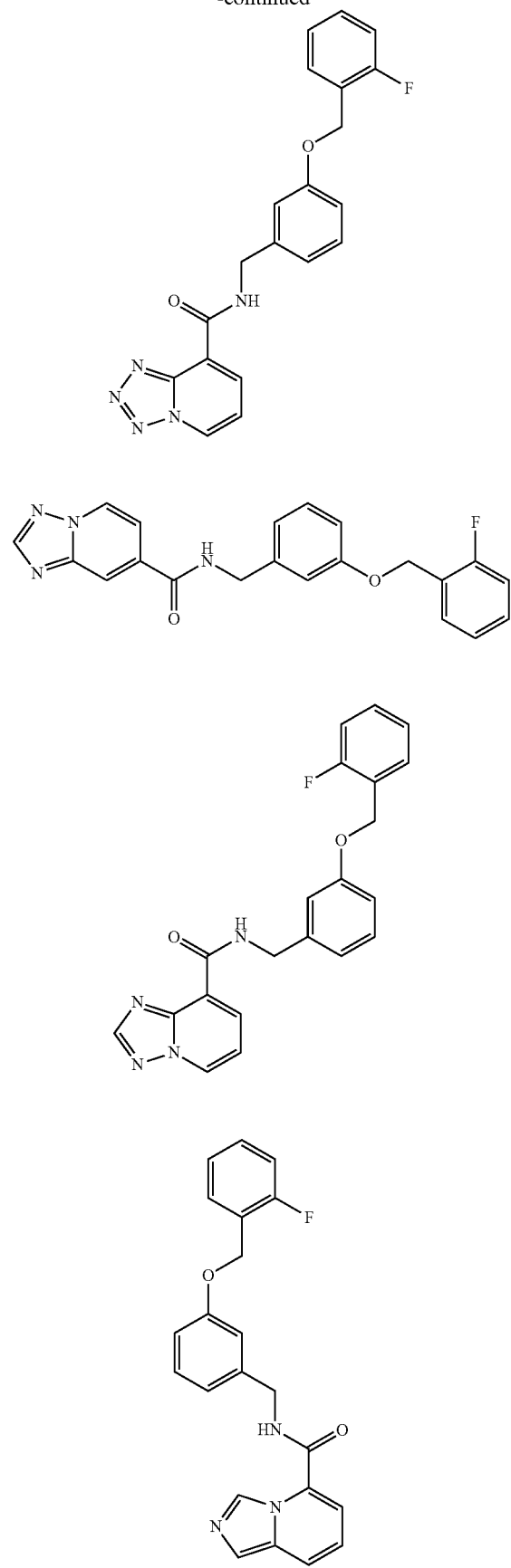
-continued
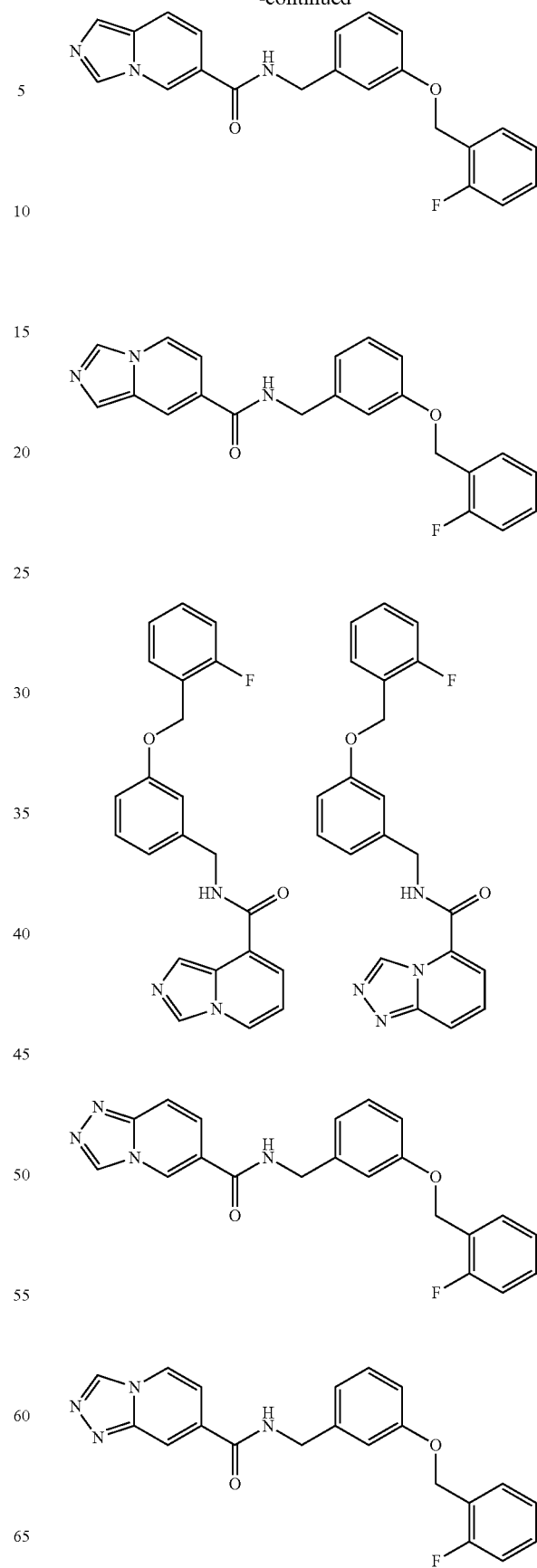

31
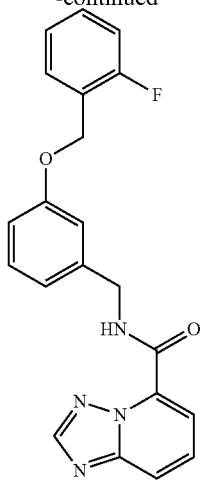
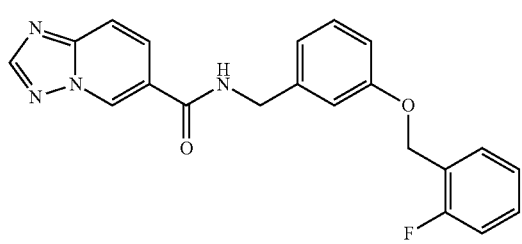
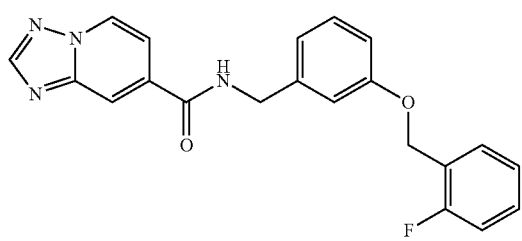
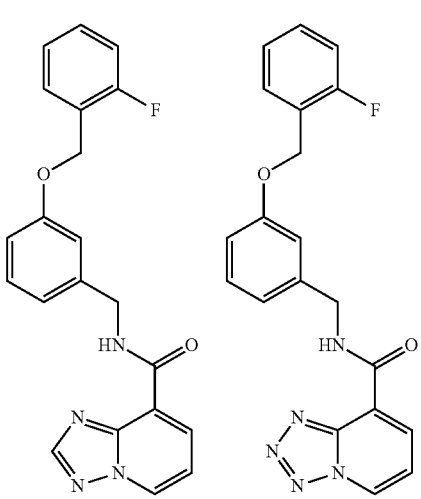
32
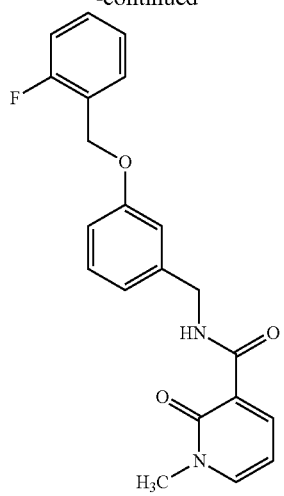
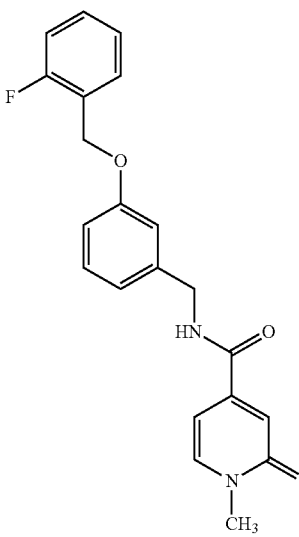
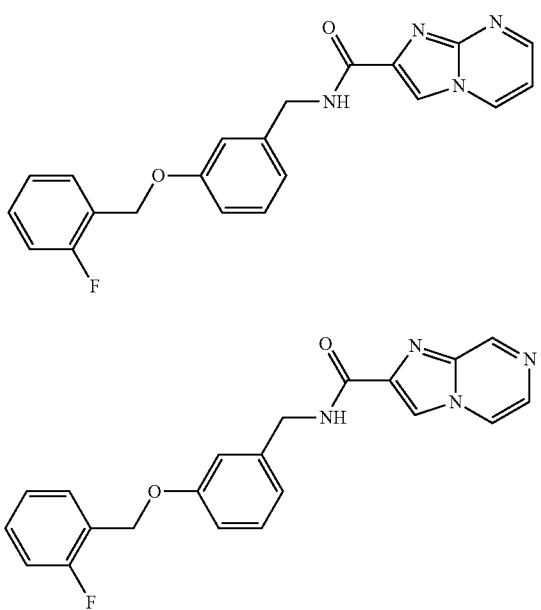

33
-continued
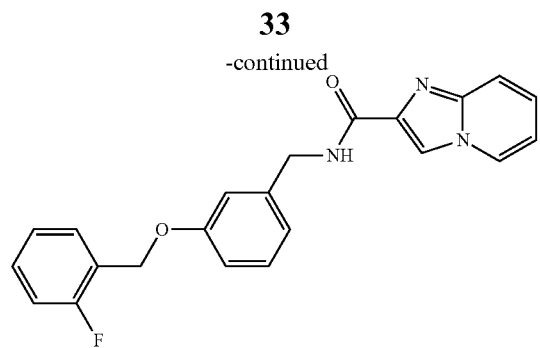
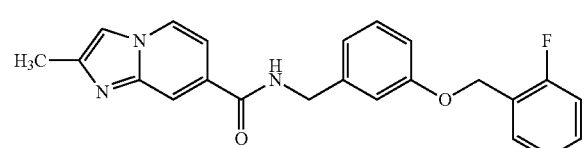
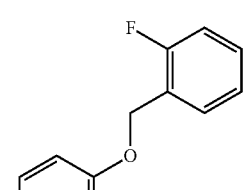
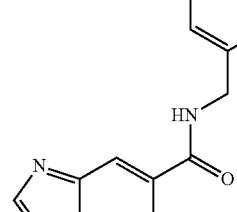
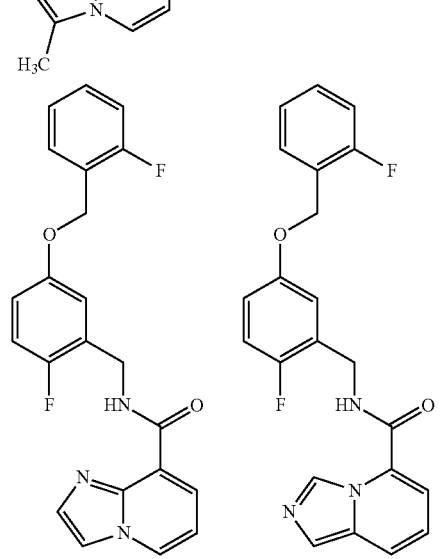
34
-continued
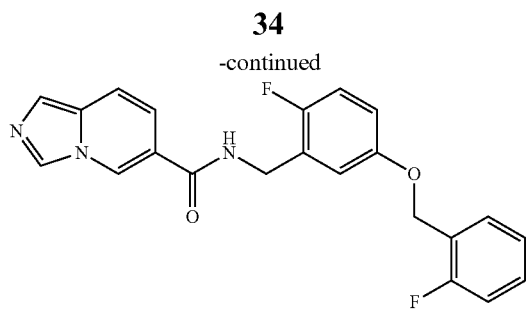
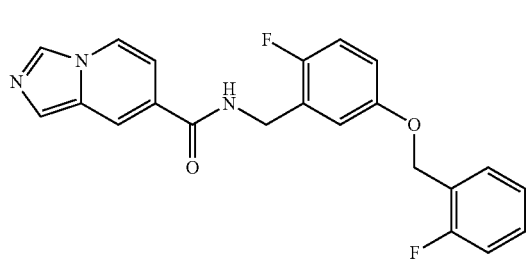
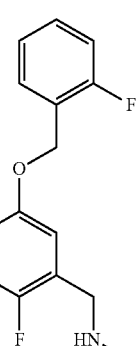
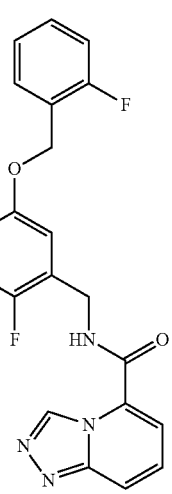
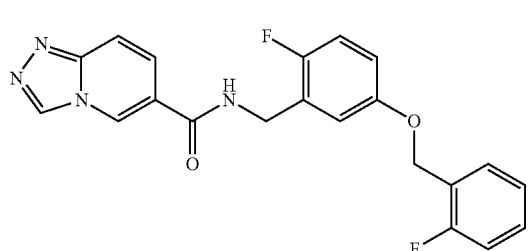
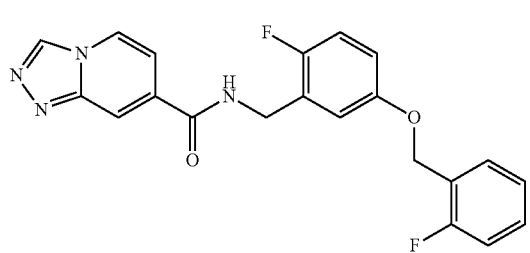

35
-continued
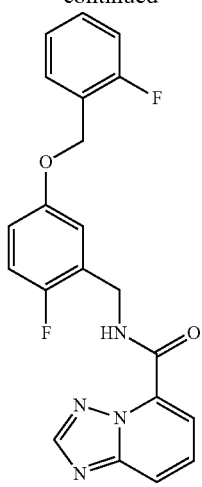
36
-continued
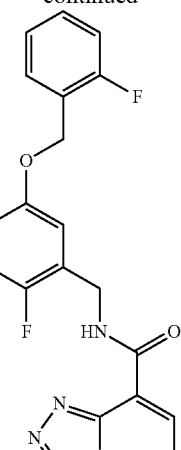
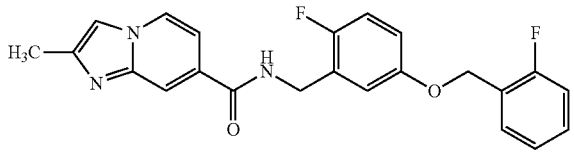
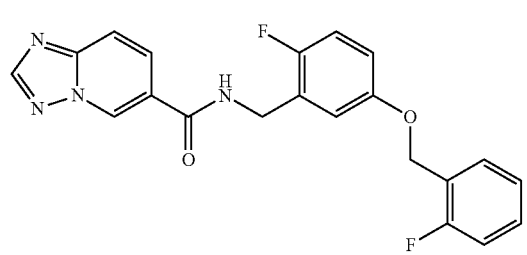
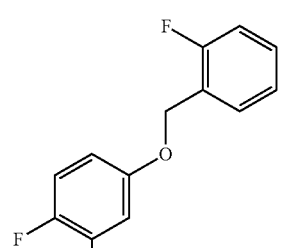
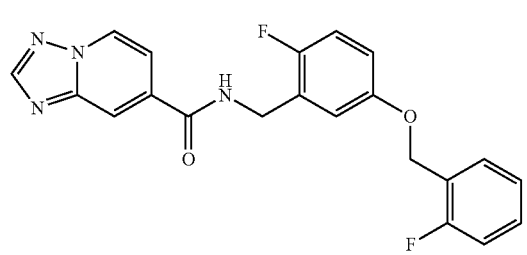
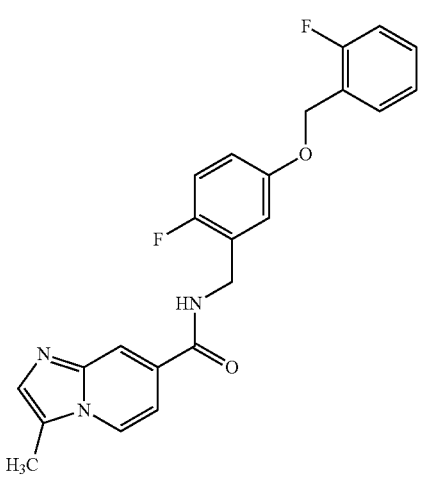
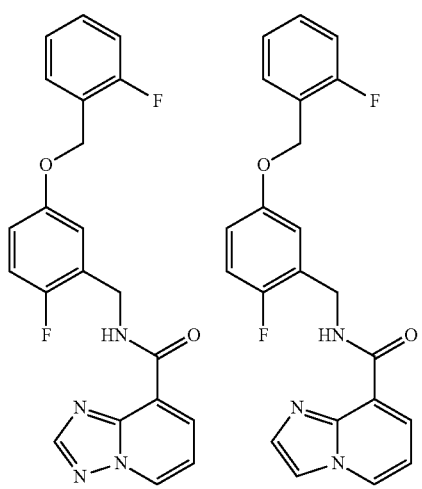
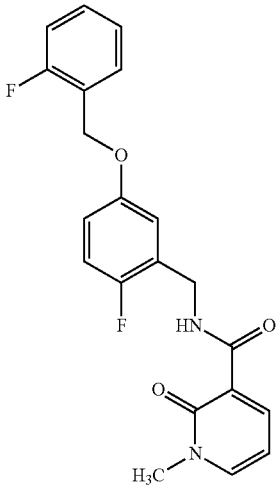

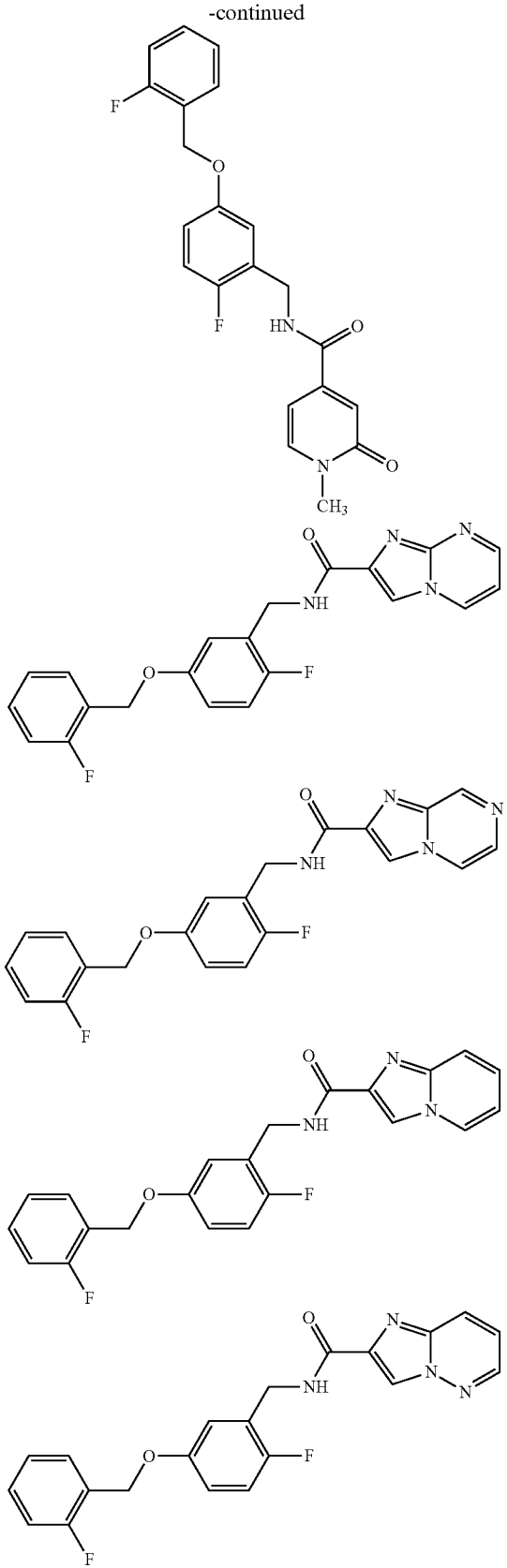

The salts of the compounds of the invention are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of the invention, and the salts thereof, can be presented in the form of pharmaceutically acceptable derivatives. The term "pharmaceutically acceptable derivative" includes pharmaceutically acceptable esters, prodrugs, solvates and hydrates of the compounds of Formula (I), or salts thereof. Pharmaceutically acceptable derivatives may include any pharmaceutically acceptable hydrate or any other compound or prodrug which, upon administration to a subject, is capable of providing (directly or indirectly) a compound of Formula (I), or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form and/or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of the invention or of salt thereof.

It will be appreciated that the compounds of the invention may have at least one asymmetric centre, and therefore are capable of existing in more than one stereoisomeric form.

The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds or pharmaceutically acceptable salts thereof, including pharmaceutically acceptable derivatives thereof, and optionally a pharmaceutically acceptable carrier or diluent.

In another aspect, the present invention provides pharmaceutical compositions for use as a sodium ion channel modulators, more particularly as pain relief agents, the composition comprising an effective amount of a Compound of Formula (I), or a pharmaceutically acceptable salt thereof, including a pharmaceutically acceptable derivative thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of the compound of the invention to be administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The pharmaceutical preparations of the compounds according to the present invention may be co-administered with one or more other active agents in combination therapy.

For example the pharmaceutical preparation of the active compound may be co-administered (for example, separately, concurrently or sequentially), with one or more other agents used to treat cognitive impairment or mood disorders such as acetylcholine esterase inhibitors, antipsychotics, and antidepressants.

General Synthetic Schemes and Description
General Procedures

Examples

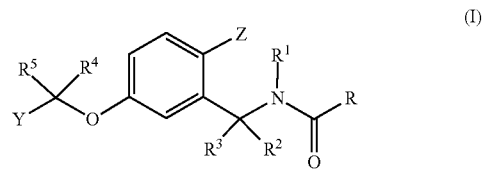

(I)

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), ether or diethyl ether ($Et_2O$), ethyl acetate (EtOAc), triethylamine ($Et_3N$), dichloromethane (methylene chloride, DCM), trifluoroacetic acid (TFA), trifluoroethanol (TFE), dimethylformamide (DMF), sodium sulphate ($Na_2SO_4$), tetrahydrofuran (THF), meta-chloroperbenzoic acid (mCPBA), hexamethyldisilazane sodium salt (NaHMDS), O-(7-azabenzotriazol-1-yl)-N,N,N',N'-tetramethyluronium hexafluorophosphate (HATU), dimethylsulfoxide (DMSO), magnesium sulphate ($MgSO_4$), sodium hydrogen carbonate ($NaHCO_3$), tert-butanol (t-BuOH), 1-ethyl-3-(3-dimethylaminopropyl) carbodiimide hydrochloride salt (EDCI·HCl), tetra-n-butylammonium fluoride (TBAF), N,N-diisopropylethylamine (DIPEA), 1-hydroxybenzotriazole (HOBt), trans-dichlorobis(triphenylphosphine)palladium(II) ($PdCl_2(PPh_3)_2$), tetrakis(triphenylphosphine)palladium(0) ($Pd(PPh_3)_4$) tris (dibenzylideneacetone) dipalladium(0) ($Pd_2(dba)_3$), tri-t- butyl phosphonium tetrafluoroborate (t-Bu$_3$PH·BF$_4$), 4,5-bis(diphenylphosphino)-9,9-dimethylxanthene (Xantphos), triphenylphosphine (PPh$_3$), diisopropyl azodicarboxylate (DIAD), pyridinium chlorochromate (PCC), borane dimethylsulfide (BMS), titanium isopropoxide (TiOiPr$_4$), sodium triacetoxyborohydride (NaBH(OAc)$_3$), sodium cyanoborohydride (NaBH$_3$(CN)), ammonium chloride (NH$_4$Cl), chloroform (CHCl$_3$), manganese dioxide (MnO$_2$), potassium carbonate (K$_2$CO$_3$) and 1,2-dichloroethane (DCE).

General Experimental Details

Unless otherwise stated the following generalisations apply.

NMR, HPLC, MS and Mp data provided in the examples described below are registered on:

NMR: Agilent DD2 (500 MHz), Aglient DD2 (600 MHz) or Varian DD2 (300 MHz) using residual signal of deuterated solvent as internal reference.

LCMS: Agilent Technologies LC/MS (1260 Infinity, 6120 Quadrupole LC/MS), column Zorbax SB-C8, 4.6×150 mm, 5µ, with mobile phase 80% ACN, 15% H$_2$O, 5% buffer (3:1 MeOH/H$_2$O, 315 mg HCO$_2$NH$_4$, 1 mL AcOH) and MS detection (ESI method).

Mp: SRS OptiMelt—Automated Melting Point System

Analytical thin-layer chromatography (TLC) was performed on Merck silica gel 60F254 aluminium-backed plates which were visualised using fluorescence quenching under UV light or using an acidic anisaldehyde or a basic potassium permanganate dip. Flash chromatography was performed using either a Teledyne Isco CombiFlash Rf purification system using standard RediSep® cartridges. Microwave irradiation was achieved using a CEM Explorer 48 Microwave Reactor. All reactions carried out using microwave irradiation were stirred.

Where necessary, anhydrous solvents were prepared using a Glascontour purification system or purchased from Sigma-Aldrich.

A—General Procedure for Benzylamine Synthesis

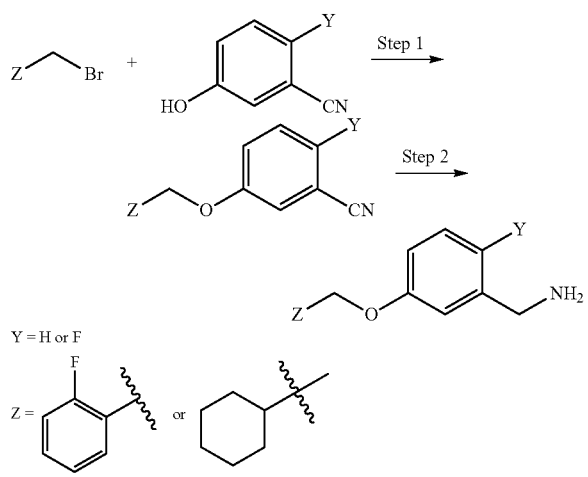

Step 1: Benzylamine Synthesis

Sodium carbonate or potassium carbonate (1.1 eq) was added to a solution of the bromide (1.0 eq) and phenol (1.1 eq) in acetone or dimethylformamide. The mixture was stirred at room temperature or at elevated temperature (for example 60° C.) overnight or until the reaction was complete. The mixture was then extracted with ethyl acetate, dried over magnesium sulfate, filtered and evaporated. The residue was purified by flash chromatography on silica gel.

Step 2: Benzylamine Synthesis

At 0° C., lithium aluminum hydride (3.0 eq) was suspended in tetrahydrofuran. A solution of the benzonitrile from step 1 (1.0 eq) in tetrahydrofuran was added dropwise at 0° C. The mixture was stirred from 0° C. to room temperature overnight or until the reaction was complete. The reaction mixture was then cooled down to 0° C. again and quenched by careful addition of water. A 2 M solution of sodium hydroxide was then added. The mixture was stirred at 0° C. for 1 h and was then filtered through a short pad of celite, which was rinsed with methylene chloride and ethyl acetate. The filtrate was evaporated to afford the benzylamine. Purification if required was carried out by flash chromatography in silica gel.

B—Synthesis of 2-(3-(cyclohexylmethoxy)phenyl)propan-2-amine

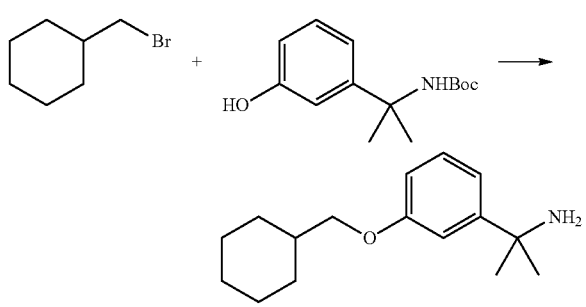

Tert-butyl (2-(3-hydroxyphenyl)propan-2-yl)carbamate, (bromomethyl)cyclohexane (130 mL) and Cs$_2$CO$_3$ (304.4 mg, 0.934 mmol) were combined in a flask under N$_2$ and taken up in dry DMA (5 mL). The reaction was warmed at 100° C. over the weekend. LCMS showed formation of the desired product. The reaction was quenched with saturated NH$_4$Cl solution and then extracted with EtOAc (2×). The extracts were combined, washed with H$_2$O (×3) and brine, dried over MgSO$_4$, filtered and concentrated in vacuo. The crude material was purified by flash column chromatography on silica using a ethyl acetate hexane gradient as eluent.

C—Synthesis of 2-(3-((2-fluorobenzyl)oxy)phenyl)propan-2-amine

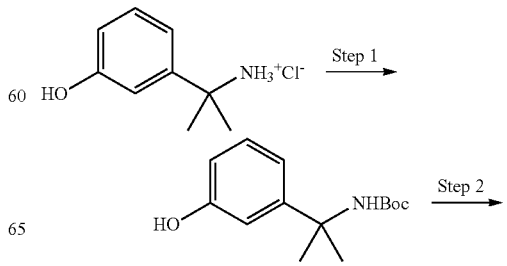

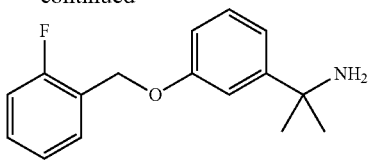

Step 1:

2-(3-Hydroxyphenyl)propan-2-aminium chloride (301 mg, 1.60 mmol) was taken up in dry dichloromethane (10 mL) and triethylamine (450 uL, 3.23 mmol) under N₂. The mixture was cooled to 0° C. before di-tert-butyl dicarbonate (363 mg, 1.66 mmol) was added and the reaction mixture was allowed to achieve ambient temperature over 3 h. Additional triethylamine (250 uL, 1.79 mmol) and di-tert-butyl dicarbonate (368 mg, 1.69 mmol) was added and the reaction was stirred at ambient temperature overnight. The reaction was quenched with saturated NH₄Cl solution and then extracted with EtOAc (2×). The extracts were combined, dried over MgSO₄, filtered and concentrated in vacuo. The crude material was purified by flash column chromatography on silica using an ethyl acetate dichloromethane gradient as eluent to give the desired product (349 mg, 86%).

Step 2:

1-(bromomethyl)-2-fluorobenzene (75 uL, 0.622 mmol), potassium carbonate (102 mg, 0.739 mmol) and the product from Step 1 (148 mg, 0.589 mmol) were combined in a flask under N₂ and taken up in dry dichloromethane (5 mL). The reaction mixture was stirred at 70° C. over the weekend. The reaction was quenched with saturated NH₄Cl solution and then extracted with EtOAc (2×). The extracts were combined, washed with H₂O (×3) and brine, dried over MgSO₄, filtered and concentrated in vacuo. The crude material was purified by flash column chromatography on silica using an ethyl acetate hexane gradient as eluent. The product thus obtained was taken up in 4M HCl in dioxane (3 mL). The reaction was stirred at room temperature over 3 h. The reaction was concentrated in vacuo and the crude material triturated with n-pentane and dried in vacuo to give the desired product (58%).

D—General Procedure for Amide Couplings

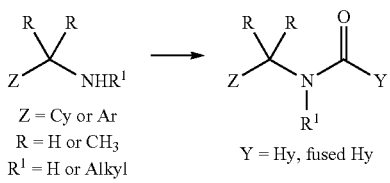

Z = Cy or Ar
R = H or CH₃
R¹ = H or Alkyl
Y = Hy, fused Hy

Amide couplings were performed using standard methods. In general, the benzylamine or the salt thereof and the carboxylic acid (1.05 eq) were combined in a flask under N₂ and taken up in a solvent such as DMF or 1,2-dichloroethane (10 mL). A base (1-2.5 eq), such as diisopropylethylamine, was added followed by an amide coupling reagent (1-2 eq) (for example hexafluorophosphate azabenzotriazole tetramethyl uronium or 50% propylphosphonic anhydride in ethyl acetate). The mixture was stirred at room temperature or at elevated temperature (for example 50° C.) overnight or until the reaction was complete. In some cases, microwave irradiation was required to effect the desired amide formation (for example irradiation at 140° C. for 1 h). The reaction was quenched with either saturated NH₄Cl or saturated NaHCO₃ solution and then extracted with solvent (for example ethyl acetate), dried over magnesium sulfate, filtered and evaporated. The residue was purified by standard methods (for example flash chromatography on silica gel, preparative HPLC, trituration or Sephadex purification).

E—Synthesis of [3-[1-(2-fluorophenyl)-1-methyl-ethoxy]phenyl]methanamine

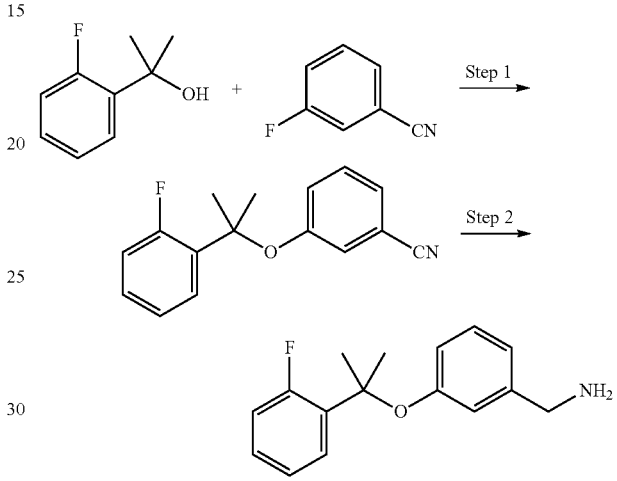

Step 1:

Sodium hydride (60% in oil, 525 mg, 13.1 mmol, 1.1 eq) was added at 0° C. to a solution of 2-(2-fluorophenyl)propan-2-ol (1.8 g, 12 mmol, 1.0 eq) in 15 mL of DMF. The mixture was stirred at 0° C. during 15 min. Then, 3-fluorobenzonitrile (1.4 g, 12 mmol, 1.0 eq) was added at the same temperature. The mixture was warmed up to room temperature for 30 min then stirred at 50° C. for 20 h. After cooling, water was added followed by saturated solution of ammonium chloride before extraction with ethyl acetate (×3). The organic layers were dried over magnesium sulfate, filtered and concentrated under vacuo. The residue was purified by flash chromatography over silica gel using cyclohexane and ethyl acetate (10:0 to 5:5) to afford the expected compound as yellow oil (858 mg, 26% yield).

Step 2:

A lithium aluminium hydride solution (2M in THF, 3.3 mL, 6.7 mmol, 2.0 eq) was added dropwise at 0° C. to a solution of 3-[1-(2-fluorophenyl)-1-methyl-ethoxy]benzonitrile (850 mg, 3.33 mmol, 1.0 eq) in 20 mL of THF. The mixture was stirred from 0° C. to room temperature for 20 h. The reaction mixture was then cooled down to 0° C. and 0.26 mL of water was added carefully. After stirring 15 min at 0° C., 0.26 mL of a 2M solution of sodium hydroxide was added followed by 0.76 mL of water. The mixture was stirred at 0° C. during 15 min then filtered through a short pad of celite and rinsed with methylene chloride and ethyl acetate. The filtrate was evaporated and purified by flash chromatography on silica gel using dichloromethane and methanol to afford the expected compound as yellow oil (541 mg, 63% yield).

F—General Procedure for Methylation

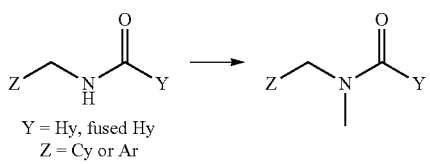

Y = Hy, fused Hy
Z = Cy or Ar

To an ice-cold solution of amide (1.0 eq) in anhydrous DMF under a nitrogen atmosphere was added 60% NaH in mineral oil (1.3 eq). The mixture was stirred for 15 minutes at 0° C. before the dropwise addition of iodomethane (3.0 eq). The cooling bath was removed, and the reaction stirred at room temperature until complete. The reaction was then diluted with EtOAc and brine was added. The aqueous phase was extracted with ethyl acetate (×3) and the combined organic phases were washed with brine (×3), dried over magnesium sulfate, filtered and evaporated. The residue was purified by flash chromatography on silica gel to afford the expected product.

G—Synthesis of 3-[(2-fluorophenyl)methoxy]benzaldehyde

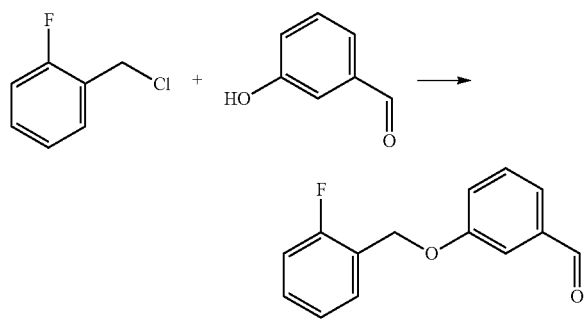

Potassium carbonate (2.5 eq) was added to a solution of 2-fluorobenzylchloride (1.0 eq) and 3-hydroxybenzaldehyde (1.1 eq) in dimethylformamide. The mixture was stirred at 60° C. overnight. After cooling down, it was evaporated, and water and ethyl acetate were added. The aqueous phase was extracted with ethyl acetate and the combined organic phases were washed with water, dried over magnesium sulfate, filtered and evaporated. The residue was purified by flash chromatography on silica gel using cyclohexane and ethyl acetate to afford the expected compound as colorless oil with 94% yield.

H—General Procedure for Reductive Amination

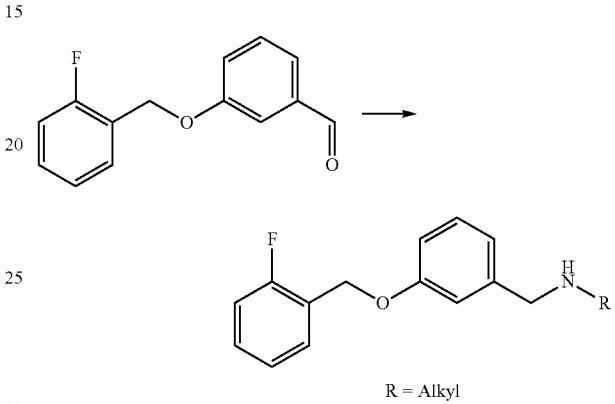

R = Alkyl

To a solution of 3-[(2-fluorophenyl)methoxy]benzaldehyde (1.1 eq) and amine (1.0 eq) in methanol was added dropwise titanium (IV) ethoxide (2.0 eq). The reaction mixture was stirred at room temperature for 18 h and sodium borohydride (1.5 eq) was added. After stirring 3 h at room temperature, the mixture was quenched with a saturated solution of sodium hydrogencarbonate. The suspension was filtered through a short pad of celite. The filtrate was extracted with dichloromethane and the combined organic phases were dried over magnesium sulfate, filtered and evaporated. The residue was purified by flash chromatography on silica gel using dichloromethane and methanol.

TABLE 1

| Number | Structure | Mol Weight | Mass (M + H) | Mass (M − H) | Synthesis - Benzylamine | Synthesis - Amide Coupling |
|---|---|---|---|---|---|---|
| 1 | 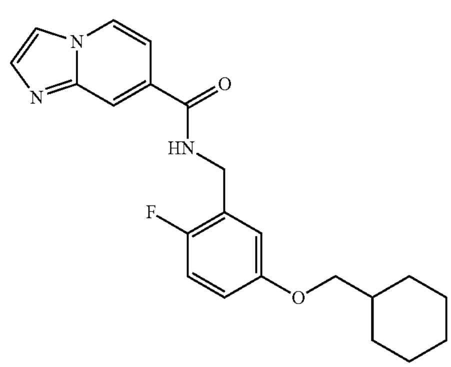 [SMILES: O=C(NCc1cc(OCC2CCCCC2)ccc1F)c1ccn2ccnc2c1] | 381.45 | 382.20 | 380.10 | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 2 | 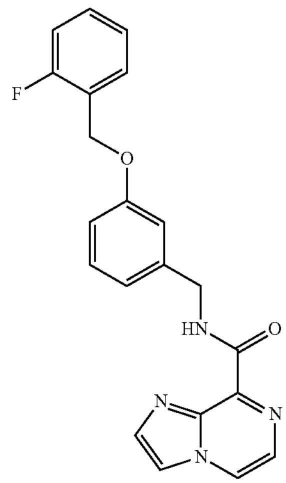 | 376.39 | 377.10 | | A | D |
| 3 | 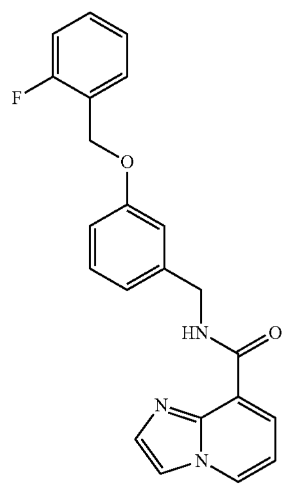 [SMILES: O=C(NCc1cccc(OCc2ccccc2F)c1)c1nccn2ccnc12] | 375.40 | 376.10 | | A | D |
| 4 | 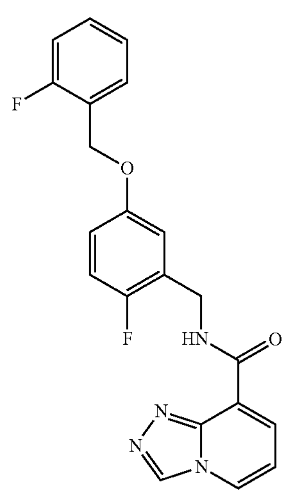 | 394.38 | 395.10 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 5 | 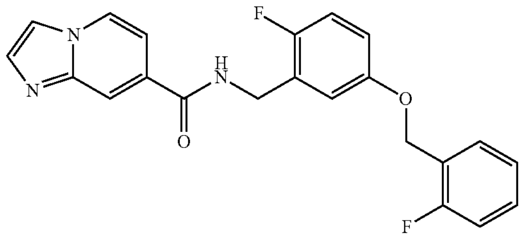 [SMILES: O=C(NCc1cc(OCc2ccccc2F)ccc1F)c1ccn2ccnc2c1] | 393.39 | 394.10 | 392.00 | A | D |
| 6 | 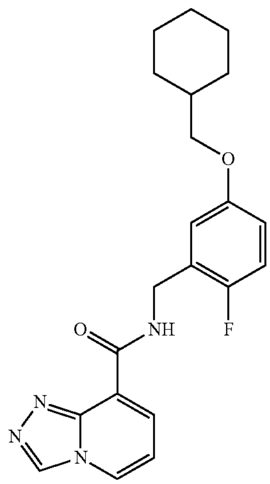 [SMILES: O=C(NCc1cc(OCC2CCCCC2)ccc1F)c1cccn2cnnc12] | 382.44 | 383.20 | | A | D |
| 7 | 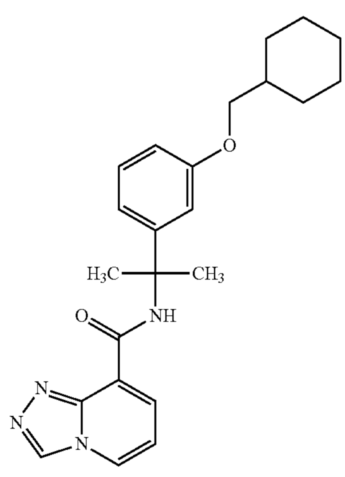 [SMILES: CC(C)(NC(=O)c1cccn2cnnc12)c1cccc(OCC2CCCCC2)c1] | 392.50 | 393.20 | | B | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 8 | 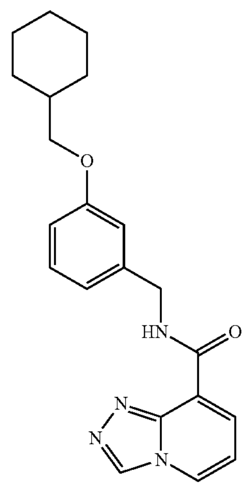 [SMILES: O=C(NCc1cccc(OCC2CCCCC2)c1)c1cccn2cnnc12] | 364.45 | 365.20 | | A | D |
| 9 | 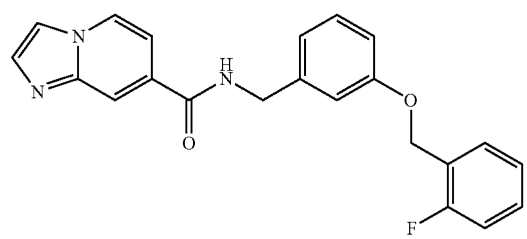 [SMILES: O=C(NCc1cccc(OCc2ccccc2F)c1)c1ccn2ccnc2c1] | 375.40 | 376.10 | | A | D |
| 10 | 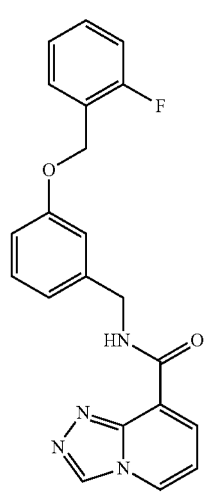 | 376.39 | 377.20 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 11 | 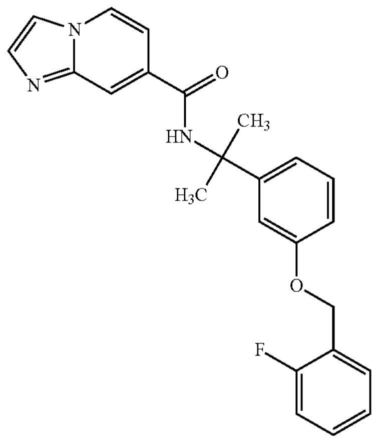 [SMILES: CC(C)(NC(=O)c1ccn2ccnc2c1)c1cccc(OCc2ccccc2F)c1] | 403.46 | 404.20 | 402.10 | C | D |
| 12 | 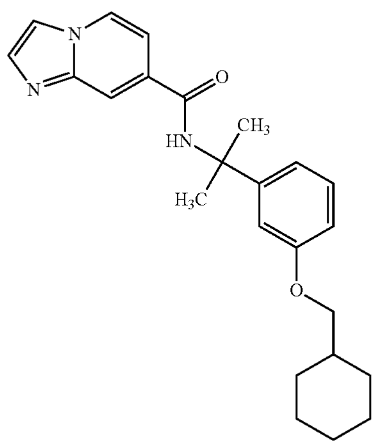 [SMILES: CC(C)(NC(=O)c1ccn2ccnc2c1)c1cccc(OCC2CCCCC2)c1] | 391.52 | 392.20 | 390.10 | B | D |
| 13 | 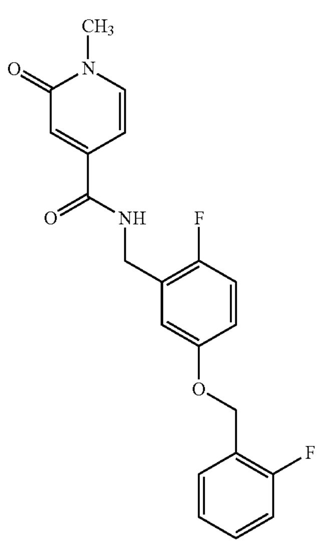 [SMILES: Cn1ccc(C(=O)NCc2cc(OCc3ccccc3F)ccc2F)cc1=O] | 384.383 | 385.33 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 14 | 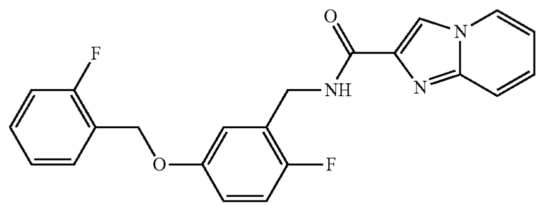 [SMILES: O=C(NCc1cc(OCc2ccccc2F)ccc1F)c1cn2ccccc2n1] | 393.394 | 394.25 | | A | D |
| 15 | 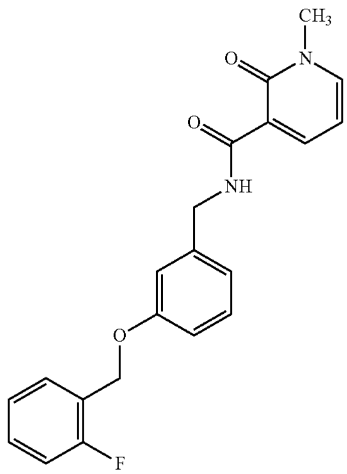 [SMILES: Cn1cccc(C(=O)NCc2cccc(OCc3ccccc3F)c2)c1=O] | 366.392 | 367.25 | | A | D |
| 16 | 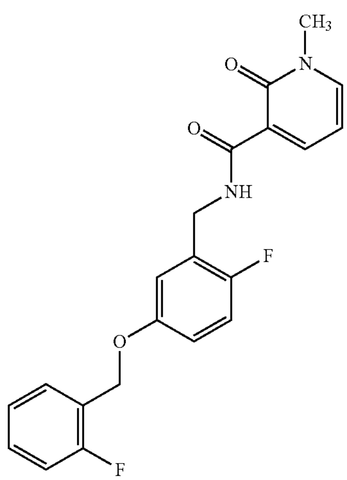 [SMILES: Cn1cccc(C(=O)NCc2cc(OCc3ccccc3F)ccc2F)c1=O] | 384.383 | 385.25 | | A | D |
| 17 | 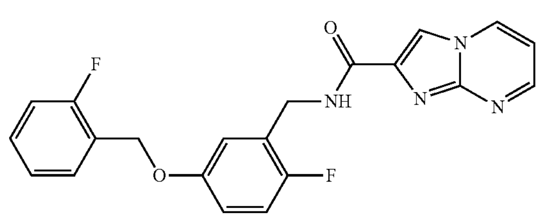 | 394.382 | 395.33 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 18 | 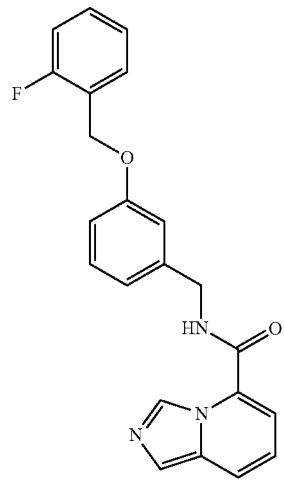 | 375.403 | 376.33 | | A | D |
| 19 | 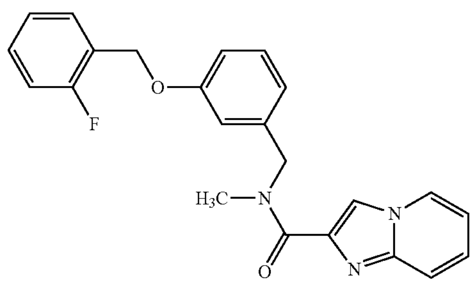 [SMILES: CN(Cc1cccc(OCc2ccccc2F)c1)C(=O)c1cn2ccccc2n1] | 389.43 | 390.33 | | A | D |
| 20 | 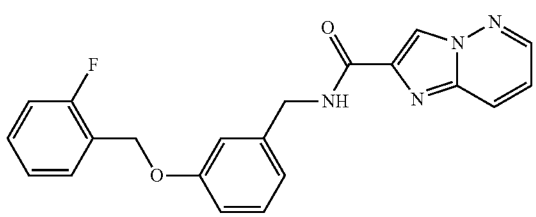 [SMILES: O=C(NCc1cccc(OCc2ccccc2F)c1)c1cn2ncccc2n1] | 376.391 | 377.33 | | A | D |
| 21 | 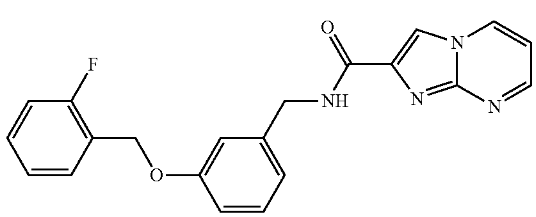 | 376.391 | 377.25 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 22 | 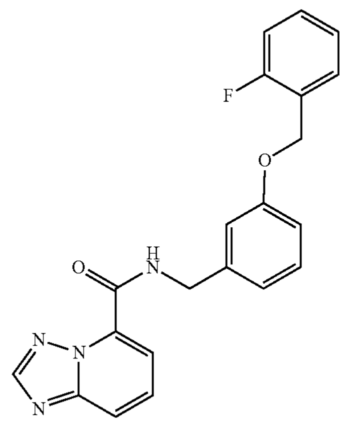 [SMILES: O=C(NCc1cccc(OCc2ccccc2F)c1)c1cccc2ncnn12] | 376.391 | 377.33 | | A | D |
| 23 | 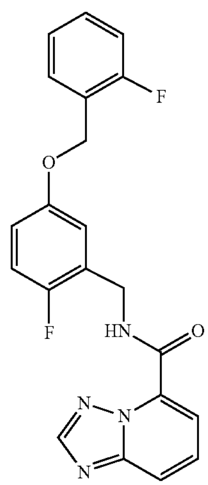 [SMILES: O=C(NCc1cc(OCc2ccccc2F)ccc1F)c1cccc2ncnn12] | 394.382 | 395.17 | | A | D |
| 24 | 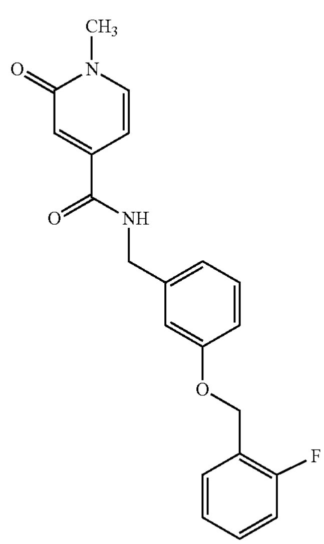 [SMILES: Cn1ccc(C(=O)NCc2cccc(OCc3ccccc3F)c2)cc1=O] | 366.392 | 367.33 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 25 | 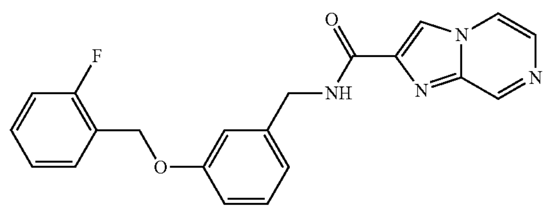 [SMILES: O=C(NCc1cccc(OCc2ccccc2F)c1)c1cn2ccncc2n1] | 376.391 | 377.25 | | A | D |
| 26 | 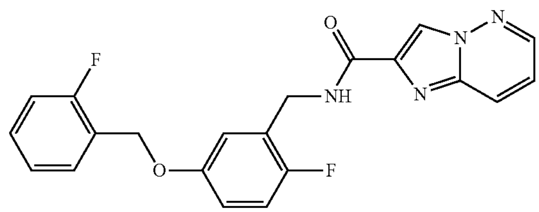 [SMILES: O=C(NCc1cc(OCc2ccccc2F)ccc1F)c1cn2ncccc2n1] | 394.382 | 395.33 | | A | D |
| 27 | 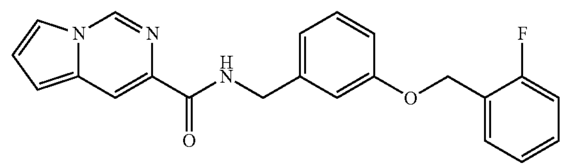 [SMILES: O=C(NCc1cccc(OCc2ccccc2F)c1)c1cc2cccn2cn1] | 375.403 | 376.25 | | A | D |
| 28 | 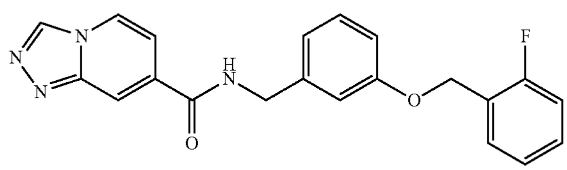 [SMILES: O=C(NCc1cccc(OCc2ccccc2F)c1)c1ccn2cnnc2c1] | 376.391 | 377.33 | | A | D |
| 29 | 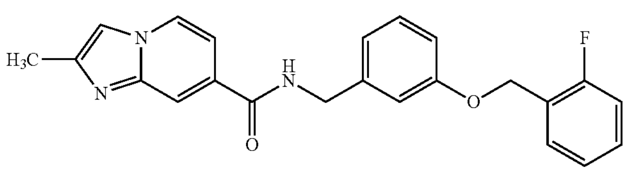 [SMILES: Cc1cn2ccc(C(=O)NCc3cccc(OCc4ccccc4F)c3)cc2n1] | 389.43 | 390.33 | | A | D |
| 30 | 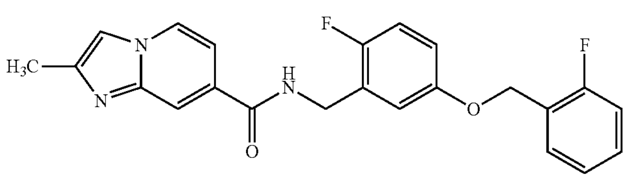 [SMILES: Cc1cn2ccc(C(=O)NCc3cc(OCc4ccccc4F)ccc3F)cc2n1] | 407.421 | 408.25 | | A | D |
| 31 | 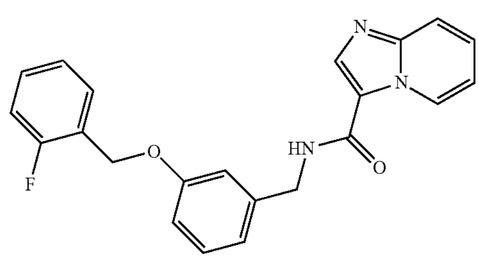 [SMILES: O=C(NCc1cccc(OCc2ccccc2F)c1)c1cnc2ccccn12] | 375.403 | 376.33 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 32 | 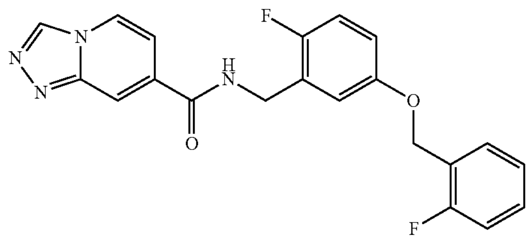 [SMILES: O=C(NCc1cc(OCc2ccccc2F)ccc1F)c1ccn2cnnc2c1] | 394.382 | 395.42 | | A | D |
| 33 | 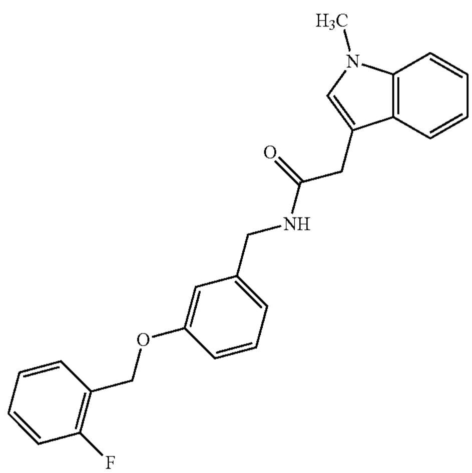 [SMILES: Cn1cc(CC(=O)NCc2cccc(OCc3ccccc3F)c2)c2ccccc21] | 402.469 | 403.33 | | A | D |
| 34 | 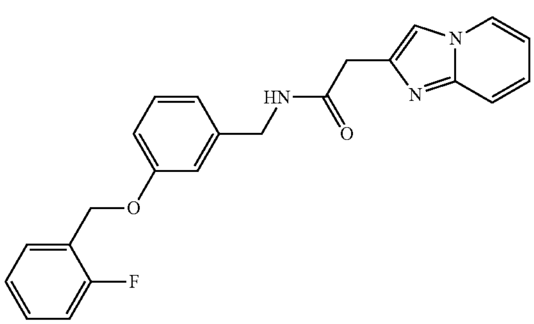 [SMILES: O=C(Cc1cn2ccccc2n1)NCc1cccc(OCc2ccccc2F)c1] | 389.43 | 390.33 | | A | D |
| 35 | 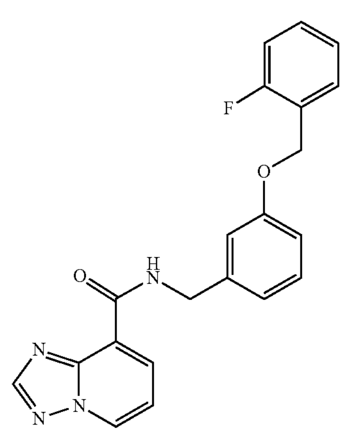 [SMILES: O=C(NCc1cccc(OCc2ccccc2F)c1)c1cccn2ncnc12] | 376.931 | 377.25 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 36 | 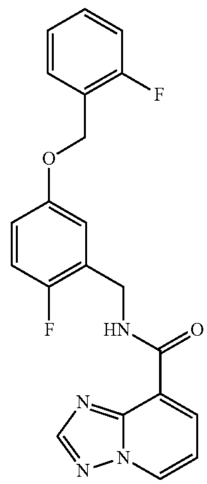 | 394.382 | 395.25 | | A | D |
| 37 | 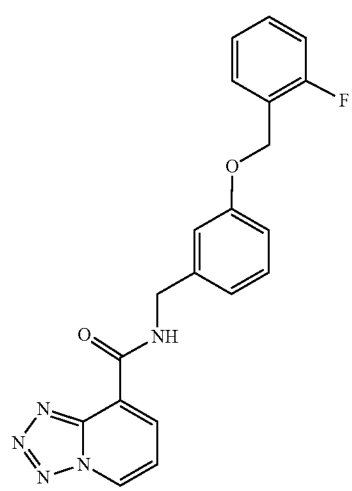 [SMILES: O=C(NCc1cccc(OCc2ccccc2F)c1)c1cccn2nnnc12] | 377.379 | 378.25 | | A | D |
| 38 | 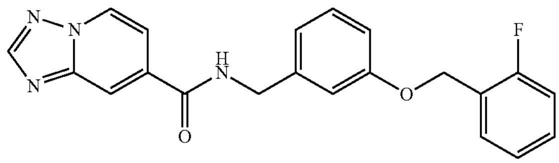 [SMILES: O=C(NCc1cccc(OCc2ccccc2F)c1)c1ccn2ncnc2c1] | 376.391 | 377.25 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 39 | 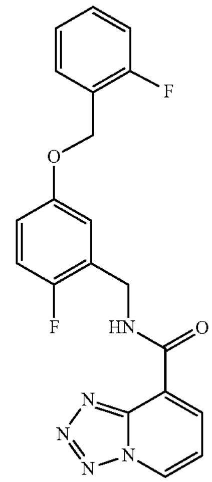 [SMILES: O=C(NCc1cc(OCc2ccccc2F)ccc1F)c1cccn2nnnc12] | 395.37 | 396.25 | | A | D |
| 40 | 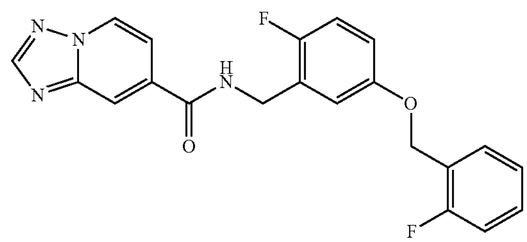 | 394.382 | 395.25 | | A | D |
| 41 | 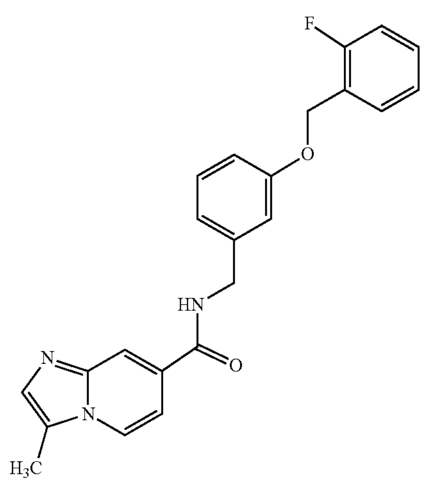 [SMILES: Cc1cnc2cc(C(=O)NCc3cccc(OCc4ccccc4F)c3)ccn12] | 389.43 | 390.42 | | A | D |
| 42 | 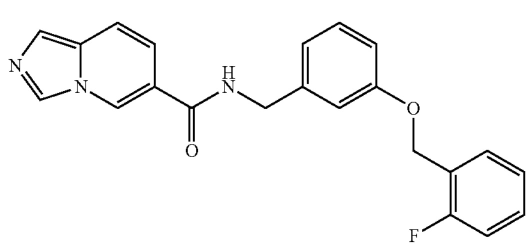 [SMILES: O=C(NCc1cccc(OCc2ccccc2F)c1)c1ccc2cncn2c1] | 375.403 | 376.33 | | A | D |

TABLE 1-continued
| Number | Structure | Mol Weight | Mass (M + H) | Mass (M − H) | Synthesis - Benzylamine | Synthesis - Amide Coupling |
|---|---|---|---|---|---|---|
| 43 | 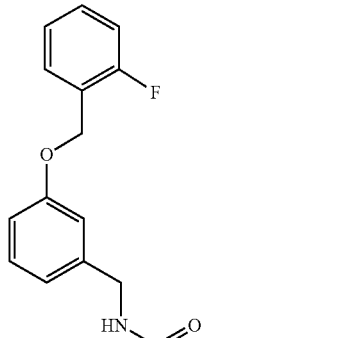 | 393.394 | 394.33 | | A | D |
| 44 | 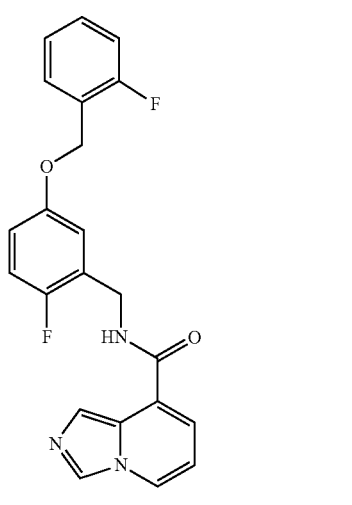 | 375.403 | 376.25 | | A | D |
| 45 | 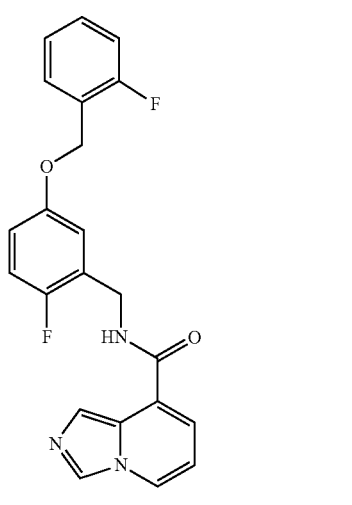 | 393.394 | 394.33 | | A | D |
| 46 | 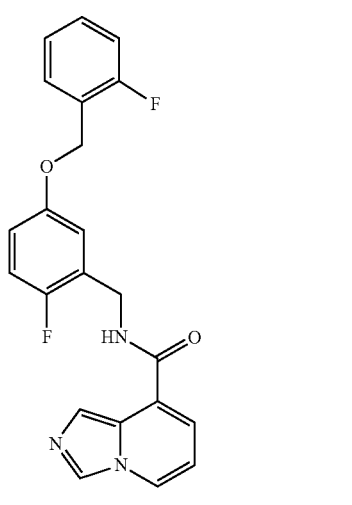 | 376.391 | 377.17 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 47 | 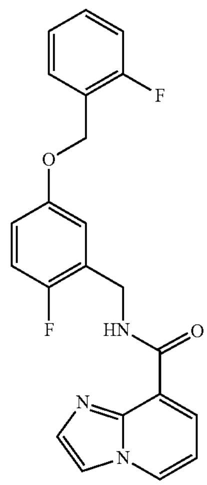 [SMILES: O=C(NCc1cc(OCc2ccccc2F)ccc1F)c1cccn2ccnc12] | 393.394 | 394.33 | | A | D |
| 48 | 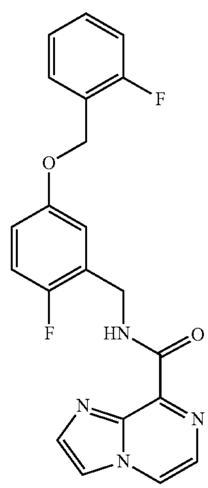 | 394.382 | 395.33 | | A | D |
| 49 | 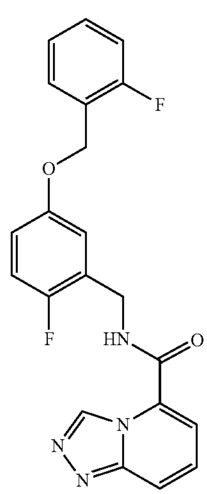 [SMILES: O=C(NCc1cc(OCc2ccccc2F)ccc1F)c1cccc2nncn12] | 394.382 | 395.33 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 50 | 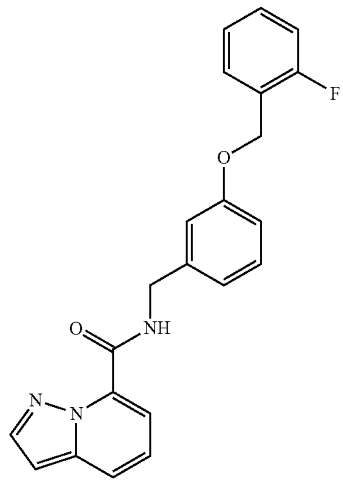 [SMILES: O=C(NCc1cccc(OCc2ccccc2F)c1)c1cccc2ccnn12] | 375.403 | 376.33 | | A | D |
| 51 | 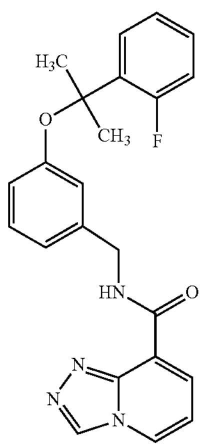 [SMILES: CC(C)(Oc1cccc(CNC(=O)c2cccn3cnnc23)c1)c1ccccc1F] | 404.445 | 405.25 | | E | D |
| 52 | 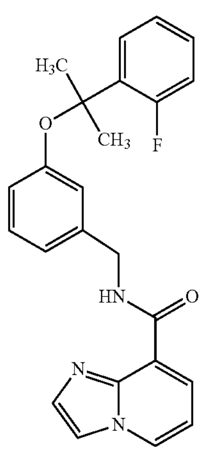 [SMILES: CC(C)(Oc1cccc(CNC(=O)c2cccn3ccnc23)c1)c1ccccc1F] | 403.457 | 404.33 | | E | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 53 | 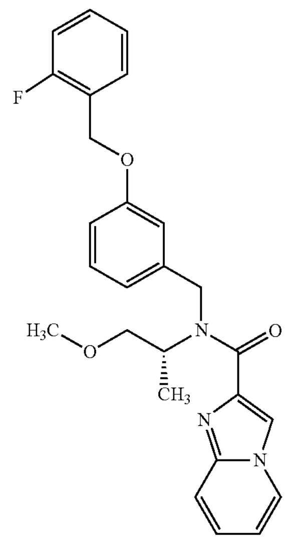 [SMILES: COC[C@@H](C)N(Cc1cccc(OCc2ccccc2F)c1)C(=O)c1cn2ccccc2n1] | 447.51 | 448.42 | | G then H | D |
| 54 | 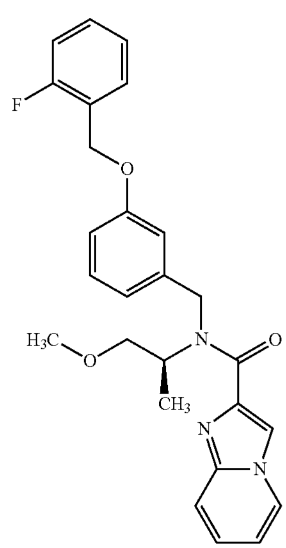 | 447.51 | 448.42 | | G then H | D |

TABLE 1-continued

| Number | Structure | Mol Weight | Mass (M + H) | Mass (M − H) | Synthesis - Benzylamine | Synthesis - Amide Coupling |
| --- | --- | --- | --- | --- | --- | --- |
| 55 | 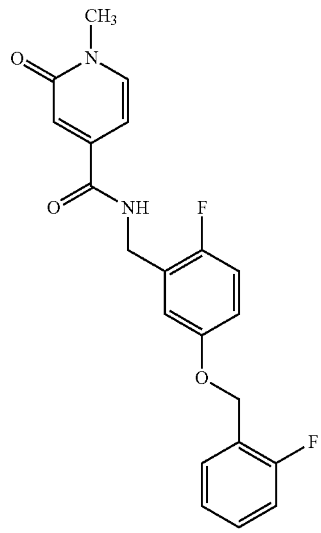 [SMILES: Cn1ccc(C(=O)NCc2cc(OCc3ccccc3F)ccc2F)cc1=O] | 384.383 | 385.33 | | A | D |
| 56 | 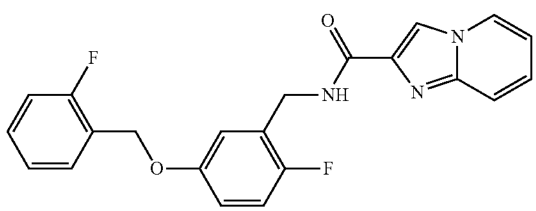 [SMILES: O=C(NCc1cc(OCc2ccccc2F)ccc1F)c1cn2ccccc2n1] | 393.394 | 394.25 | | A | D |
| 57 | 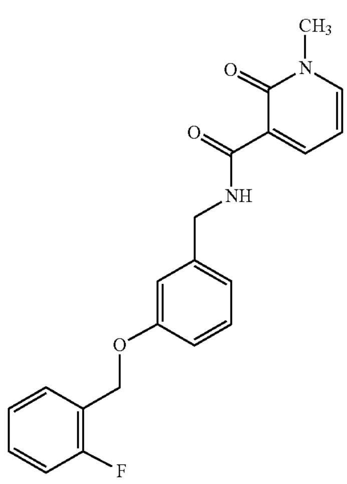 [SMILES: Cn1cccc(C(=O)NCc2cccc(OCc3ccccc3F)c2)c1=O] | 366.392 | 367.25 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 58 | 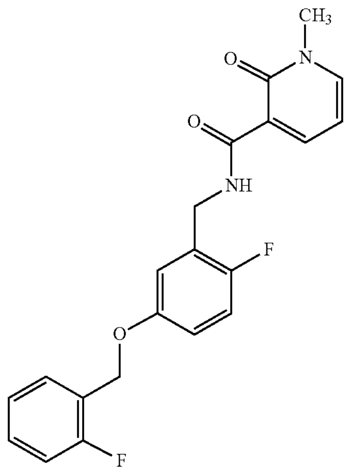 | 384.383 | 385.25 | | A | D |
| 59 | 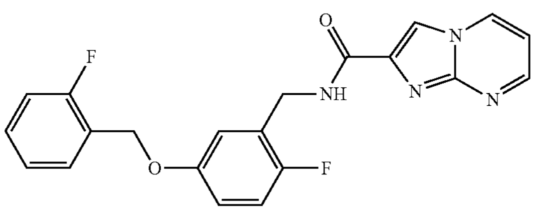 | 394.382 | 395.33 | | A | D |
| 60 | 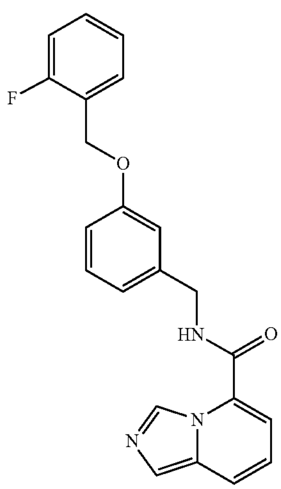 [SMILES: O=C(NCc1cccc(OCc2ccccc2F)c1)c1cccc2cncn12] | 375.403 | 376.33 | | A | D |
| 61 | 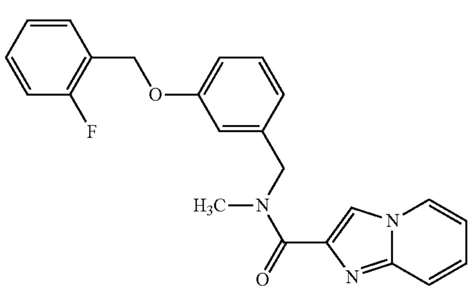 [SMILES: CN(Cc1cccc(OCc2ccccc2F)c1)C(=O)c1cn2ccccc2n1] | 389.43 | 390.33 | | A | D then F |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 62 | 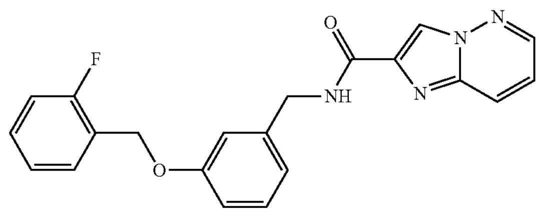 [SMILES: O=C(NCc1cccc(OCc2ccccc2F)c1)c1cn2ncccc2n1] | 376.391 | 377.33 | | A | D |
| 63 | 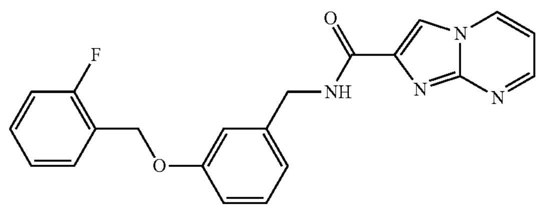 [SMILES: O=C(NCc1cccc(OCc2ccccc2F)c1)c1cn2cccnc2n1] | 376.391 | 377.25 | | A | D |
| 64 | 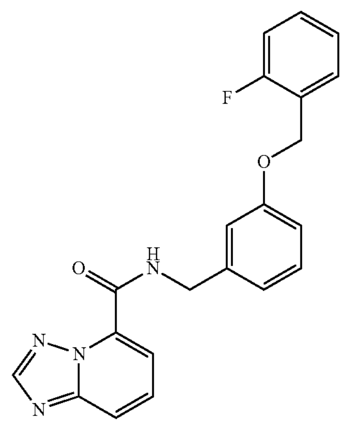 [SMILES: O=C(NCc1cccc(OCc2ccccc2F)c1)c1cccc2ncnn12] | 376.391 | 377.33 | | A | D |
| 65 | 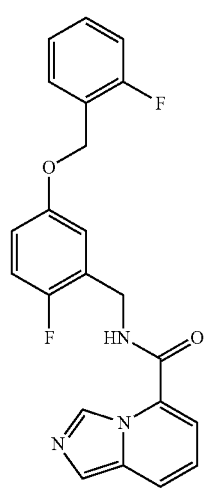 | 394.382 | 395.17 | | A | D |

TABLE 1-continued
| Number | Structure | Mol Weight | Mass (M + H) | Mass (M − H) | Synthesis - Benzylamine | Synthesis - Amide Coupling |
|---|---|---|---|---|---|---|
| 66 | 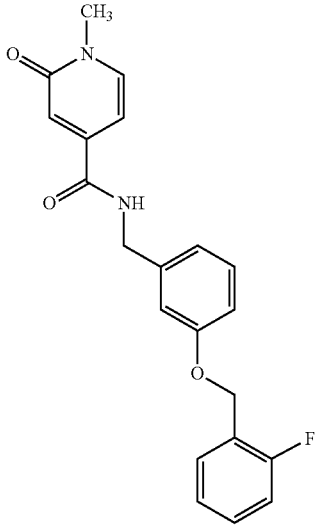 | 366.392 | 367.33 | | A | D |
| 67 | 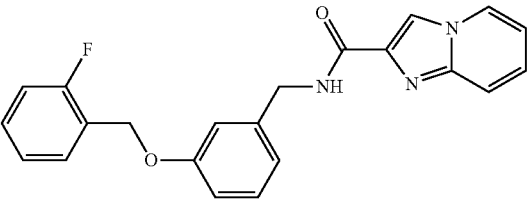 | 376.391 | 377.25 | | A | D |
| 68 | 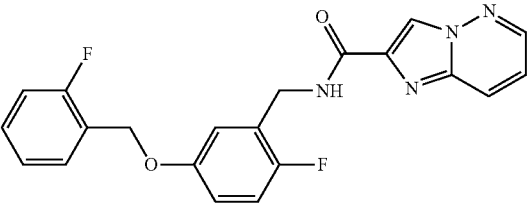 [SMILES: O=C(NCc1cc(OCc2ccccc2F)ccc1F)c1cn2ncccc2n1] | 394.382 | 395.33 | | A | D |
| 69 | 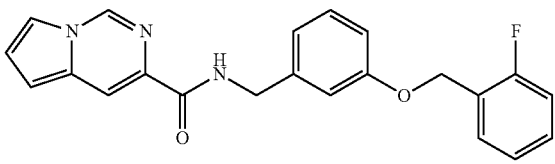 [SMILES: O=C(NCc1cccc(OCc2ccccc2F)c1)c1cc2cccn2cn1] | 375.403 | 376.25 | | A | D |
| 70 | 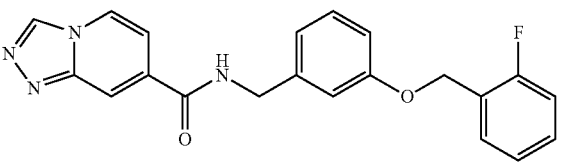 [SMILES: O=C(NCc1cccc(OCc2ccccc2F)c1)c1ccn2cnnc2c1] | 376.391 | 377.33 | | A | D |
| 71 | 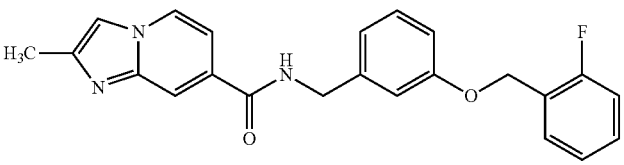 [SMILES: Cc1cn2ccc(C(=O)NCc3cccc(OCc4ccccc4F)c3)cc2n1] | 389.43 | 390.33 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 72 | 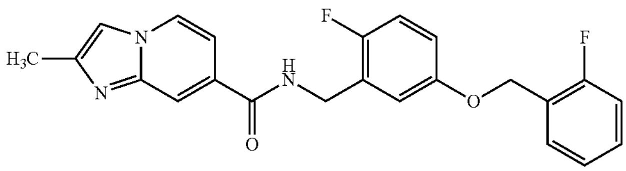 [SMILES: Cc1cn2ccc(C(=O)NCc3cc(OCc4ccccc4F)ccc3F)cc2n1] | 407.421 | 408.25 | | A | D |
| 73 | 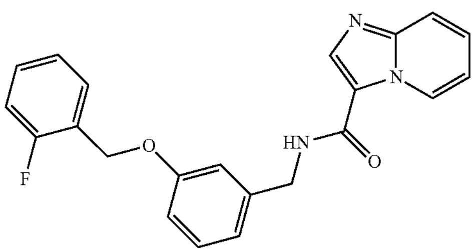 [SMILES: O=C(NCc1cccc(OCc2ccccc2F)c1)c1cnc2ccccn12] | 375.403 | 376.33 | | A | D |
| 74 | 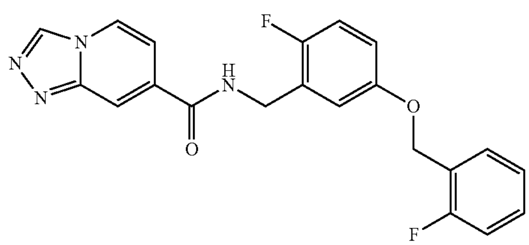 [SMILES: O=C(NCc1cc(OCc2ccccc2F)ccc1F)c1ccn2cnnc2c1] | 394.382 | 395.42 | | A | D |
| 75 | 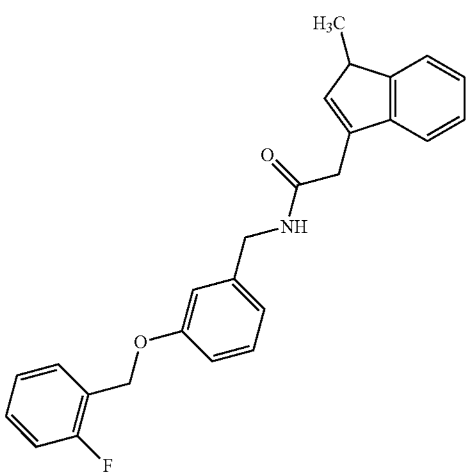 [SMILES: CC1C=C(CC(=O)NCc2cccc(OCc3ccccc3F)c2)c2ccccc21] | 402.469 | 403.33 | | A | D |
| 76 | 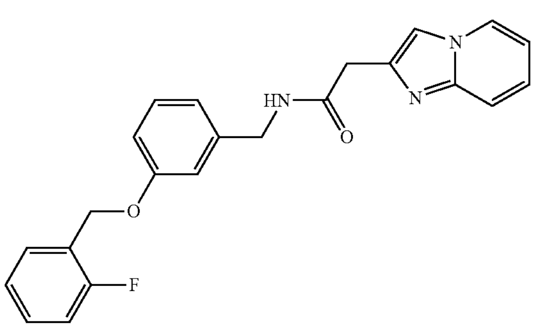 [SMILES: O=C(Cc1cn2ccccc2n1)NCc1cccc(OCc2ccccc2F)c1] | 389.43 | 390.33 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 77 | 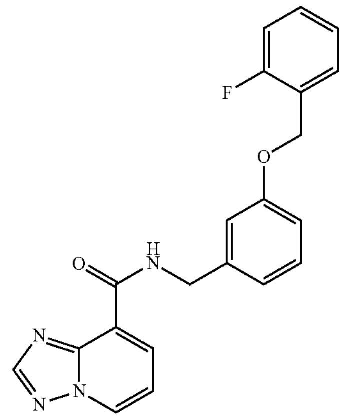 [SMILES: O=C(NCc1cccc(OCc2ccccc2F)c1)c1cccn2ncnc12] | 376.391 | 377.25 | | A | D |
| 78 | 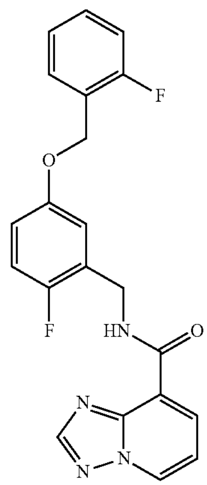 | 394.382 | 395.25 | | A | D |
| 79 | 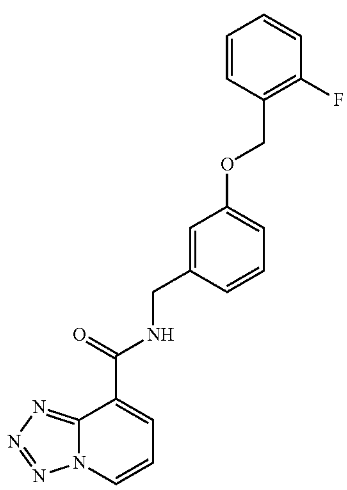 [SMILES: O=C(NCc1cccc(OCc2ccccc2F)c1)c1cccn2nnnc12] | 377.379 | 378.25 | | A | D |
| 80 | 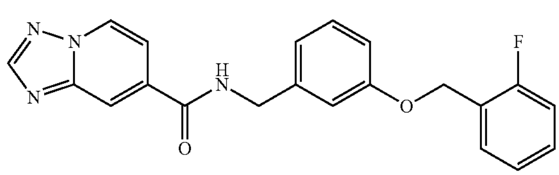 [SMILES: O=C(NCc1cccc(OCc2ccccc2F)c1)c1ccn2ncnc2c1] | 376.391 | 377.25 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 81 | 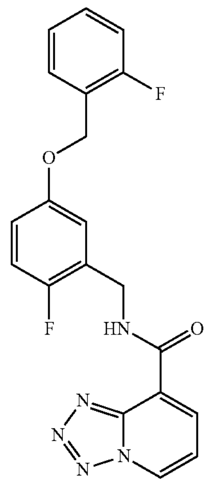 | 395.37 | 395.25 | | A | D |
| 82 | 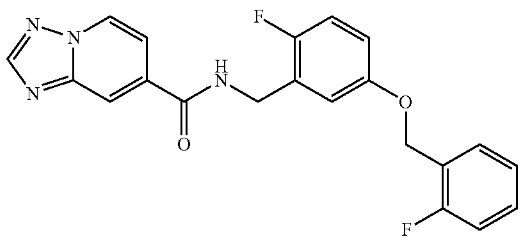 [SMILES: O=C(NCc1cc(OCc2ccccc2F)ccc1F)c1ccn2ncnc2c1] | 394.382 | 395.25 | | A | D |
| 83 | 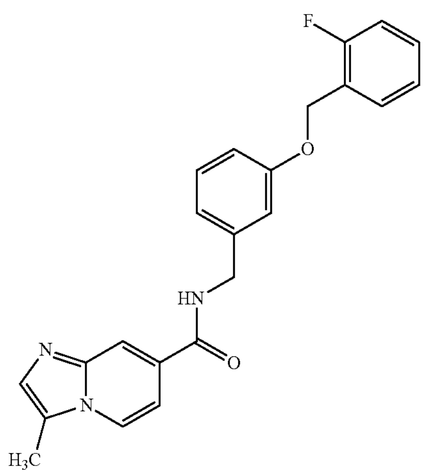 [SMILES: Cc1cnc2cc(C(=O)NCc3cccc(OCc4ccccc4F)c3)ccn12] | 389.43 | 390.42 | | A | D |
| 84 | 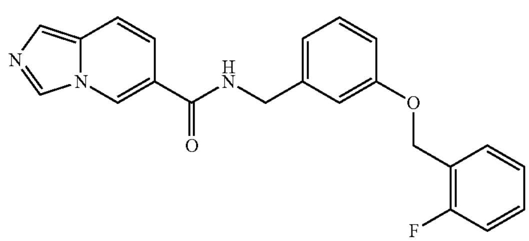 | 375.403 | 376.33 | | A | D |

TABLE 1-continued
| Number | Structure | Mol Weight | Mass (M + H) | Mass (M − H) | Synthesis - Benzylamine | Synthesis - Amide Coupling |
|---|---|---|---|---|---|---|
| 85 | 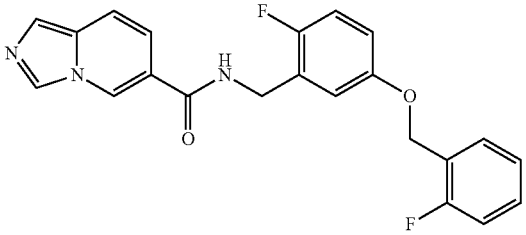 [SMILES: O=C(NCc1cc(OCc2ccccc2F)ccc1F)c1ccc2cncn2c1] | 393.394 | 394.33 | | A | D |
| 86 | 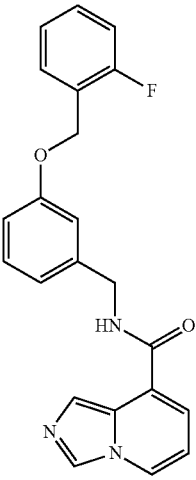 | 375.403 | 376.25 | | A | D |
| 87 | 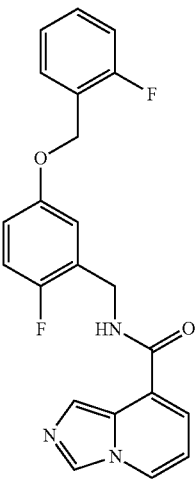 | 393.394 | 394.33 | | A | D |
| 88 | 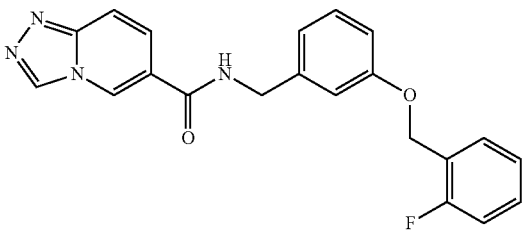 | 376.391 | 377.17 | | A | D |

TABLE 1-continued

| Number | Structure | Mol Weight | Mass (M + H) | Mass (M − H) | Synthesis - Benzylamine | Synthesis - Amide Coupling |
|---|---|---|---|---|---|---|
| 89 | 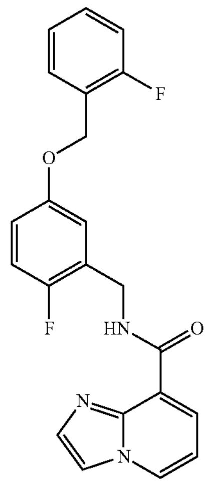 | 393.394 | 394.33 | | A | D |
| 90 | 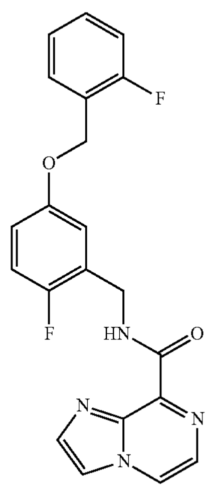 | 394.382 | 395.33 | | A | D |
| 91 | 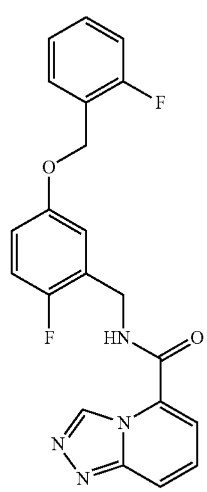 | 394.382 | 395.33 | | A | D |

TABLE 1-continued
| Number | Structure | Mol Weight | Mass (M + H) | Mass (M − H) | Synthesis - Benzylamine | Synthesis - Amide Coupling |
|---|---|---|---|---|---|---|
| 92 | 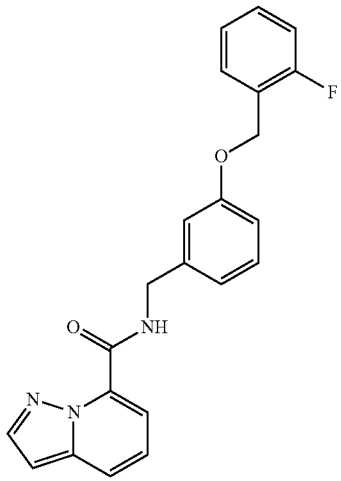 [SMILES: O=C(NCc1cccc(OCc2ccccc2F)c1)c1cccc2ccnn12] | 375.403 | 376.33 | | A | D |
| 93 | 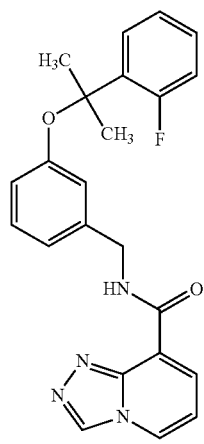 | 404.445 | 405.25 | | E | D |
| 94 | 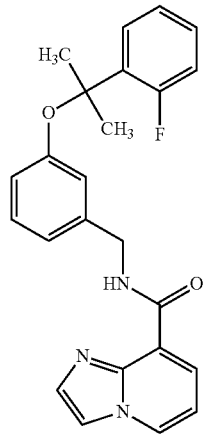 | 403.457 | 404.33 | | E | D |

| Number | Structure | Mol Weight | Mass (M + H) | Mass (M − H) | Synthesis - Benzylamine | Synthesis - Amide Coupling |
|---|---|---|---|---|---|---|
| 95 | 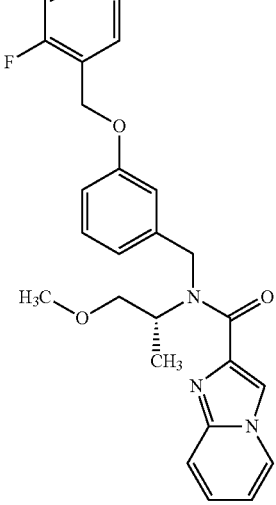 | 447.51 | 448.42 | | G then H | D |
| 96 | 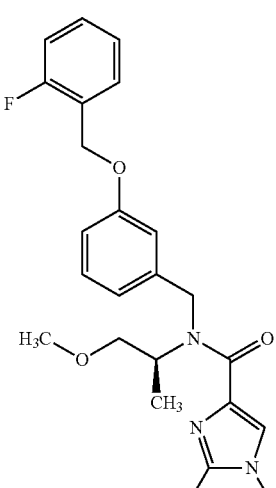 | 447.51 | 448.42 | | G then H | D |

Pharmacology

Cell Lines hNav1.7, hNav1.2, hNav1.3, hNav1.4, hNav1.5, hNav1.6 were stably expressed in human embryonic kidney cells and kept under constant antibiotic selection. For in vitro assays, cells were maintained in appropriate growth medium at 37° C. and 5% $CO_2$ in a humidified incubator.

Electrophysiology

Nav1.x expressing cells plated in T-25 flasks for 2-3 days prior to use and grown to 70-85% confluence were briefly trypsinized to obtain a single cell suspension of ~2-3×10⁶ cells/ml. All electrophysiological recordings were performed at ambient temperature (21-23° C.) using automated patch clamp (Patchliner, Nanion Technologies GmbH) in the whole-cell configuration using the following solutions: Internal solution contained (in mM): CsCl (50), NaCl (10), CsF (60), EGTA (20), HEPES (10), pH 7.2 KOH, 285 mOsmol·Kg⁻¹. External (bath) solution contained (in mM): NaCl (140), KCl (4), $MgCl_2$ (1), $CaCl_2$) (2) D-Glucose monohydrate (5), HEPES (10), pH 7.4 NaOH, 298 mOsmol·kg⁻¹.

The following voltage protocols were used to assess different Nav1.x channel states:

Resting State:

Cells were held at −120 mV and activated by 6×20 ms depolarising voltage pulses to −10 mV at a frequency of 0.1 Hz. Recordings were made initially in bath solution and 2-3 minutes after compound addition at increasing concentrations and steady state values were calculated from the 6$^{th}$ pulse (P6). % resting state inhibition was calculated by (1−(P6drug/P6control))*100%.

Inactivated State:

For each Nav1.x channel, a steady state inactivation curve was obtained in order to calculate the voltage resulting in 50% channel inactivation ($V_{0.5inact}$). A 2 pulse protocol was then employed in which cells held at a voltage corresponding to 20 mV more negative to $V_{0.5\ inact}$ were depolarised to −10 mV for 20 ms before returning to the previous holding voltage. This test pulse constituted P1 and represents 100% available (non-inactivated) Nav1.x channels. The same cell was then depolarised for 8 s to a voltage corresponding to 7 mV more positive than $V_{0.5inact}$ in order to cause channel inactivation. Following a brief (2 ms) hyperpolarising voltage step to −120 mV (to reset the activation gate), cells were again subjected to a depolarising test pulse (P2) to −10 mV for 20 ms before returning to the holding potential. Each sequence was repeated 6× at 30 s intervals. Using this protocol, control P2 current amplitudes (representing the % channels available following 8 s inactivation) was ~50% of control P1 current amplitude. 6 repetitions of this recording sequence were made in the control bath solution and then again 2 minutes after compound addition and thereafter at increasing compound concentrations. % inhibition was calculated by (1−(P2drug at repetition 6/P2control at repetition 6))*100. Data were either presented as % block by a single concentration of drug or an estimated $eIC_{50}$ determined from 2-3 drug concentrations which was determined by fitting data with a sigmoidal dose response curve (variable slope) using GraphPad Prism software (Version 6.0).

Compound Preparation

All compounds were dissolved in DMSO to 20 mM initially. Subsequent dilutions in DMSO were made to achieve 200× final bath concentrations. DMSO compound stocks were finally diluted 1/200 in bath solution just prior to assay resulting in a final DMSO concentration of 0.5% which was not found to affect control current amplitude.

TABLE 2

| Number | Structure | hNav1.7 SIS (% inh) | Assay Conc. (uM) | hNav1.7 SIS (IC50 uM) |
|---|---|---|---|---|
| 1 | 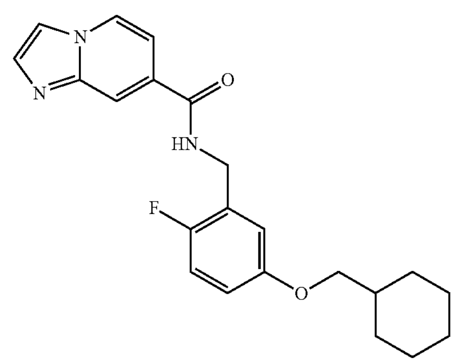 [SMILES: O=C(NCc1cc(OCC2CCCCC2)ccc1F)c1ccn2ccnc2c1] | | | 0.41 |
| 2 | 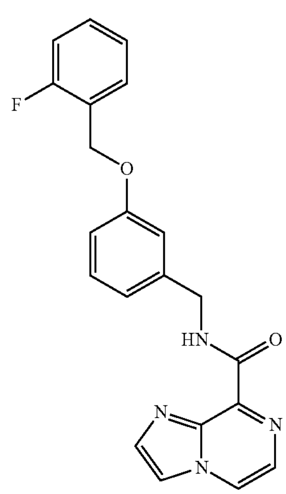 [SMILES: O=C(NCc1cccc(OCc2ccccc2F)c1)c1nccn2ccnc12] | | | 1.3 |

TABLE 2-continued
| Number | Structure | hNav1.7 SIS (% inh) | Assay Conc. (uM) | hNav1.7 SIS (IC50 uM) |
|---|---|---|---|---|
| 3 | 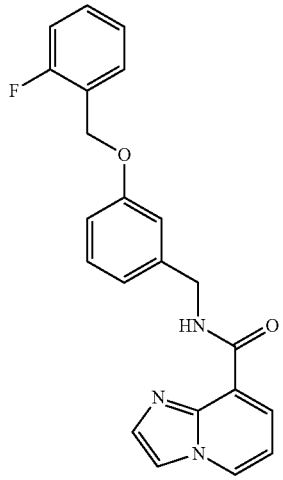 | | | 2.7 |
| 4 | 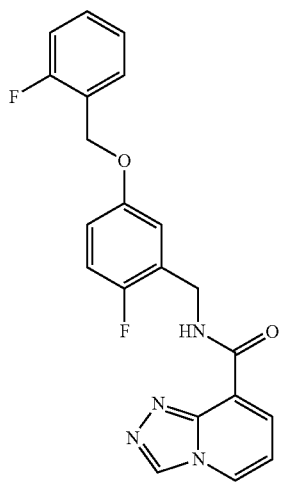 | | | 1.1 |
| 5 | 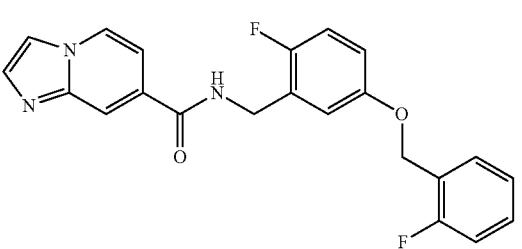 [SMILES: O=C(NCc1cc(OCc2ccccc2F)ccc1F)c1ccn2ccnc2c1] | | | 1.3 |

TABLE 2-continued
| Number | Structure | hNav1.7 SIS (% inh) | Assay Conc. (uM) | hNav1.7 SIS (IC50 uM) |
|---|---|---|---|---|
| 6 | 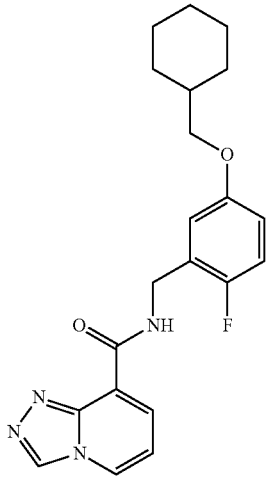 [SMILES: O=C(NCc1cc(OCC2CCCCC2)ccc1F)c1cccn2cnnc12] | | | 0.13 |
| 7 | 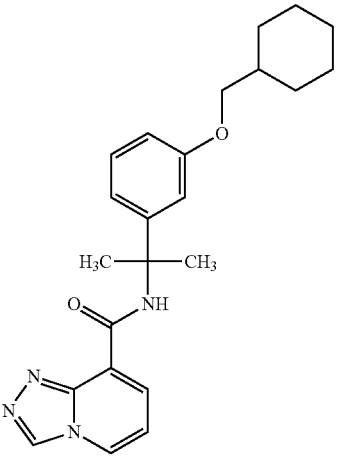 [SMILES: CC(C)(NC(=O)c1cccn2cnnc12)c1cccc(OCC2CCCCC2)c1] | | | 4.8 |
| 8 | 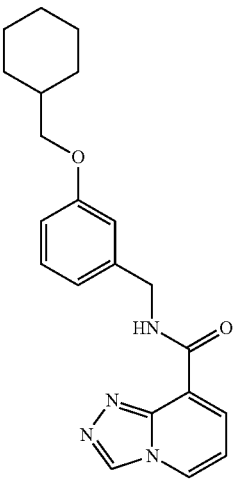 [SMILES: O=C(NCc1cccc(OCC2CCCCC2)c1)c1cccn2cnnc12] | | | 0.91 |

TABLE 2-continued

| Number | Structure | hNav1.7 SIS (% inh) | Assay Conc. (uM) | hNav1.7 SIS (IC50 uM) |
|---|---|---|---|---|
| 9 | 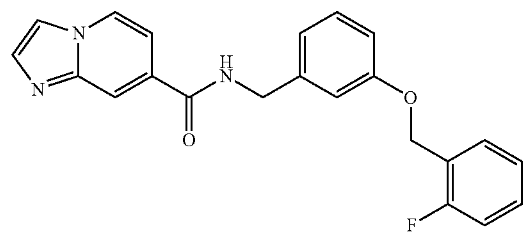 [SMILES: O=C(NCc1cccc(OCc2ccccc2F)c1)c1ccn2ccnc2c1] | | | 8.9 |
| 10 | 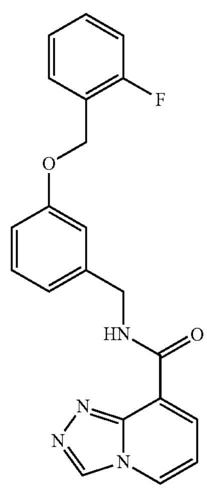 [SMILES: O=C(NCc1cccc(OCc2ccccc2F)c1)c1cccn2cnnc12] | | | 3.3 |
| 11 | 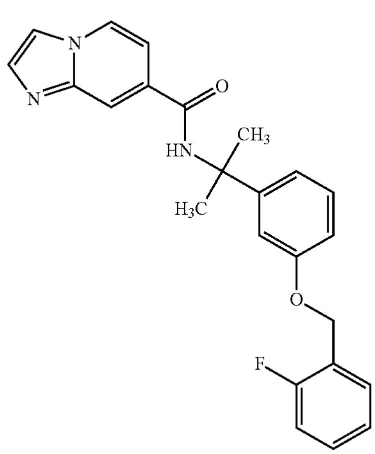 [SMILES: CC(C)(NC(=O)c1ccn2ccnc2c1)c1cccc(OCc2ccccc2F)c1] | 45 | 10 | |

TABLE 2-continued

| Number | Structure | hNav1.7 SIS (% inh) | Assay Conc. (uM) | hNav1.7 SIS (IC50 uM) |
|---|---|---|---|---|
| 12 | 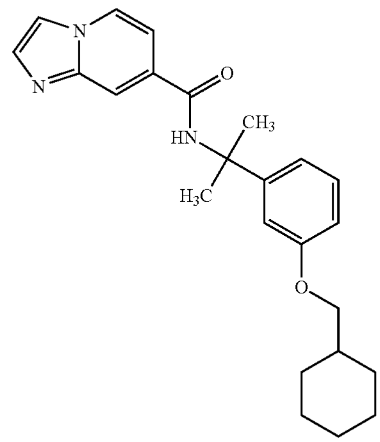 [SMILES: CC(C)(NC(=O)c1ccn2ccnc2c1)c1cccc(OCC2CCCCC2)c1] | | | 0.51 |
| 13 | 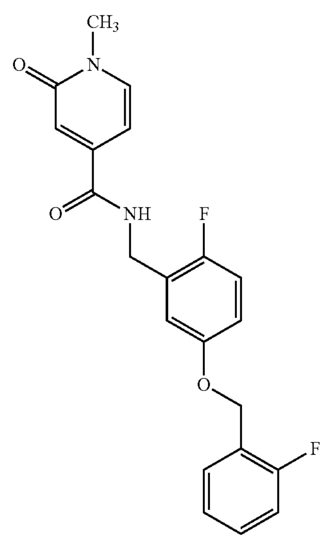 [SMILES: Cn1ccc(C(=O)NCc2cc(OCc3ccccc3F)ccc2F)cc1=O] | 49 | 10.00 | |
| 14 | 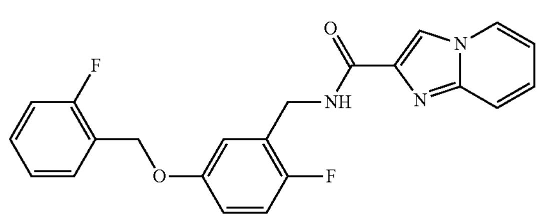 [SMILES: O=C(NCc1cc(OCc2ccccc2F)ccc1F)c1cn2ccccc2n1] | | | 2.2 |

TABLE 2-continued

| Number | Structure | hNav1.7 SIS (% inh) | Assay Conc. (uM) | hNav1.7 SIS (IC50 uM) |
|---|---|---|---|---|
| 15 | 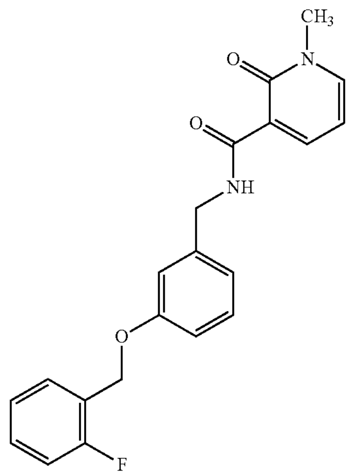 [SMILES: Cn1cccc(C(=O)NCc2cccc(OCc3ccccc3F)c2)c1=O] | 53 | 10.00 | |
| 16 | 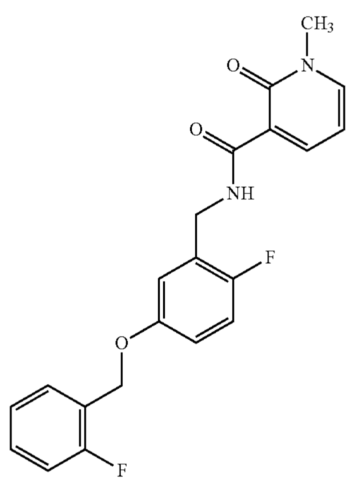 [SMILES: Cn1cccc(C(=O)NCc2cc(OCc3ccccc3F)ccc2F)c1=O] | 52 | 10.00 | |
| 17 | 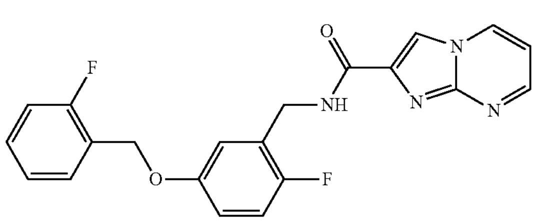 | 42 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 18 | 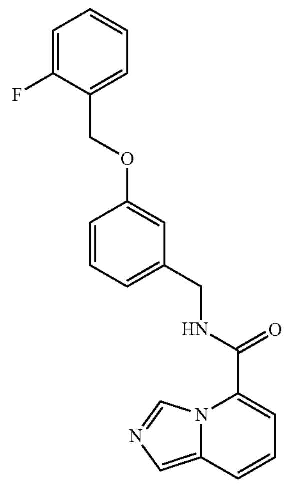 [SMILES: O=C(NCc1cccc(OCc2ccccc2F)c1)c1cccc2cncn12] | 49 | 10.00 | |
| 19 | 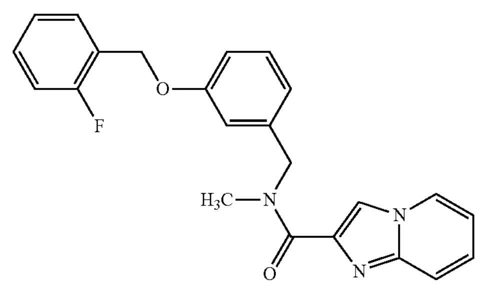 [SMILES: CN(Cc1cccc(OCc2ccccc2F)c1)C(=O)c1cn2ccccc2n1] | | | 1.6 |
| 20 | 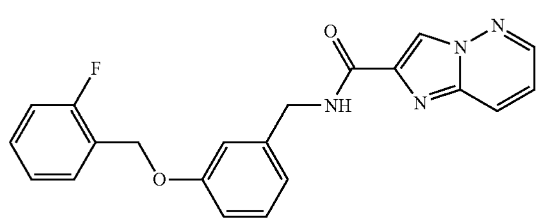 [SMILES: O=C(NCc1cccc(OCc2ccccc2F)c1)c1cn2ncccc2n1] | 50 | 10.00 | |
| 21 | 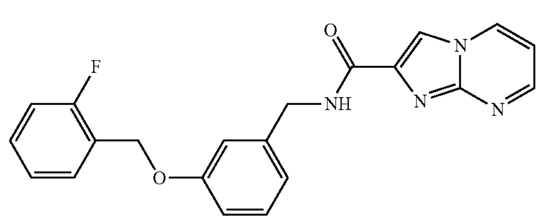 [SMILES: O=C(NCc1cccc(OCc2ccccc2F)c1)c1cn2cccnc2n1] | 42 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 22 | 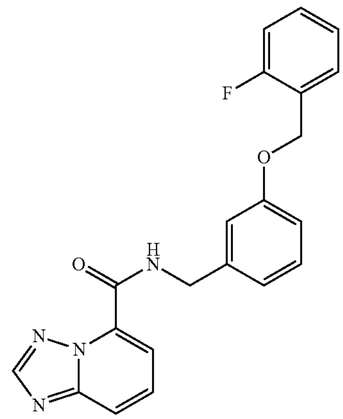 [SMILES: O=C(NCc1cccc(OCc2ccccc2F)c1)c1cccc2ncnn12] | 48 | 10.00 | |
| 23 | 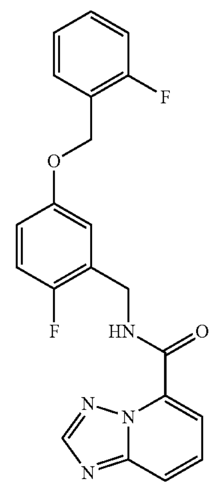 [SMILES: O=C(NCc1cc(OCc2ccccc2F)ccc1F)c1cccc2ncnn12] | | | 10 |
| 24 | 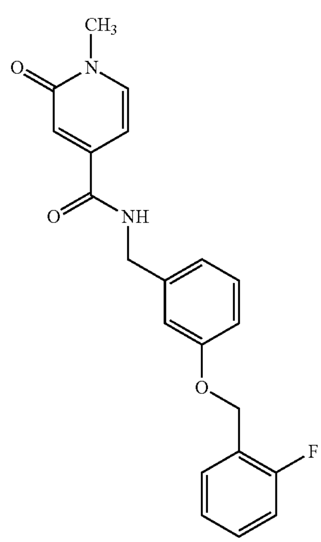 | 30 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 25 | 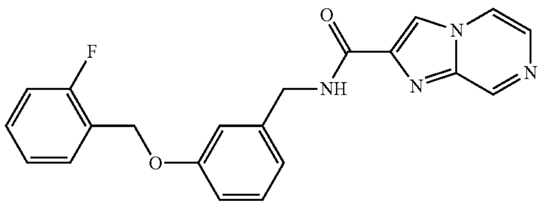 [SMILES: O=C(NCc1cccc(OCc2ccccc2F)c1)c1cn2ccncc2n1] | 34 | 10.00 | |
| 26 | 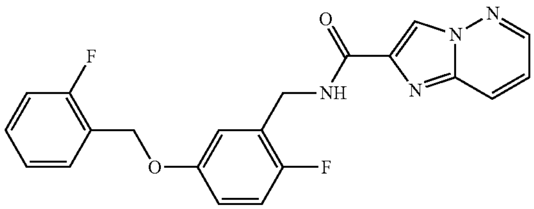 | 53 | 10.00 | |
| 27 | 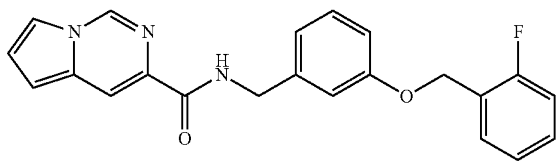 [SMILES: O=C(NCc1cccc(OCc2ccccc2F)c1)c1cc2cccn2cn1] | 92 | 10.00 | |
| 28 | 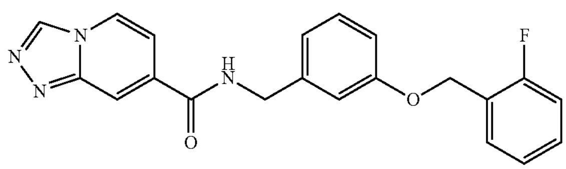 [SMILES: O=C(NCc1cccc(OCc2ccccc2F)c1)c1ccn2cnnc2c1] | 66 | 10.00 | |
| 29 | 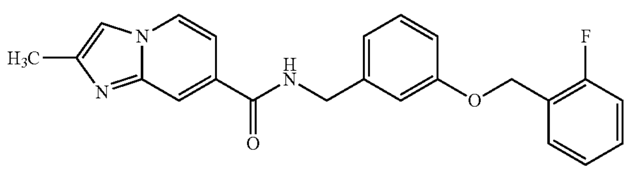 [SMILES: Cc1cn2ccc(C(=O)NCc3cccc(OCc4ccccc4F)c3)cc2n1] | 66 | 10.00 | |
| 30 | 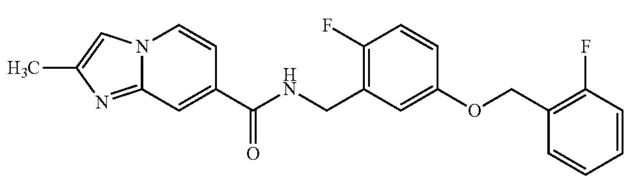 [SMILES: Cc1cn2ccc(C(=O)NCc3cc(OCc4ccccc4F)ccc3F)cc2n1] | 100 | 10.00 | |
| 31 | 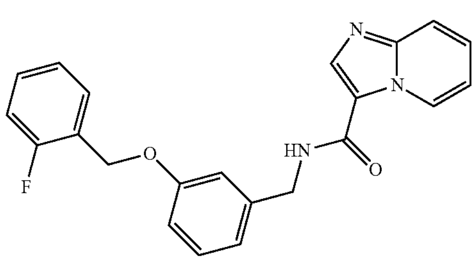 [SMILES: O=C(NCc1cccc(OCc2ccccc2F)c1)c1cnc2ccccn12] | 47 | 10.00 | |

TABLE 2-continued
| Number | Structure | hNav1.7 SIS (% inh) | Assay Conc. (uM) | hNav1.7 SIS (IC50 uM) |
|---|---|---|---|---|
| 32 | 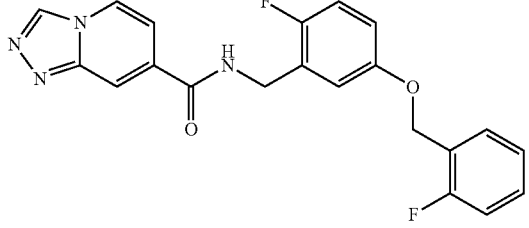 | 58 | 10.00 | |
| 33 | 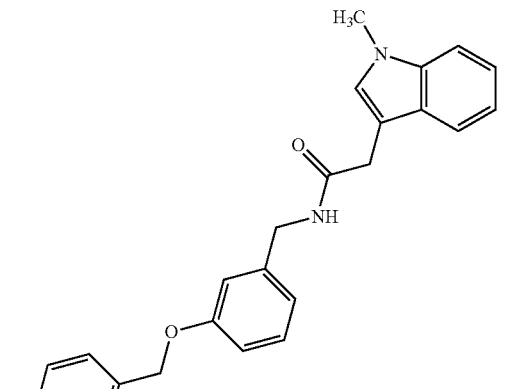 | 74 | 10.00 | |
| 34 | 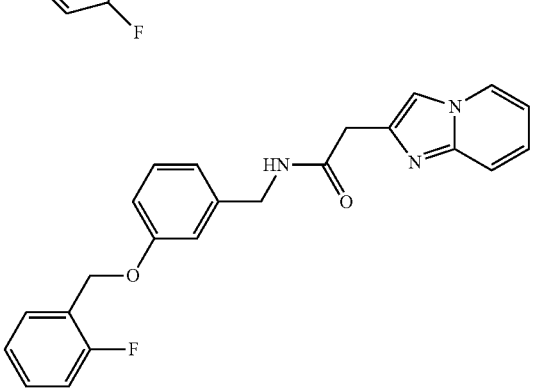 | 44 | 10.00 | |
| 35 | 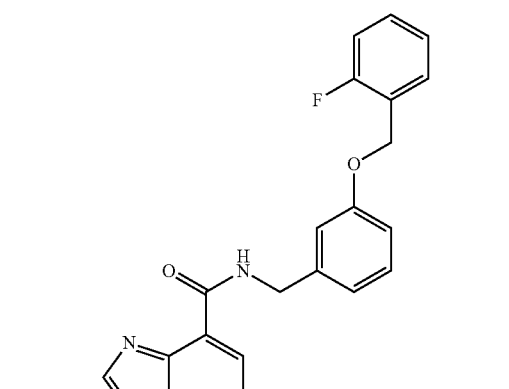 | 70 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 36 | 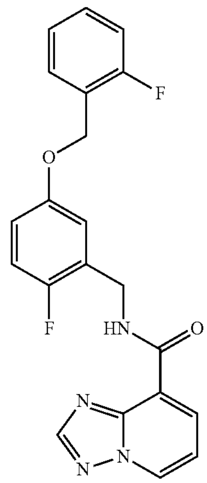 [SMILES: O=C(NCc1cc(OCc2ccccc2F)ccc1F)c1cccn2ncnc12] | 83 | 10.00 | |
| 37 | 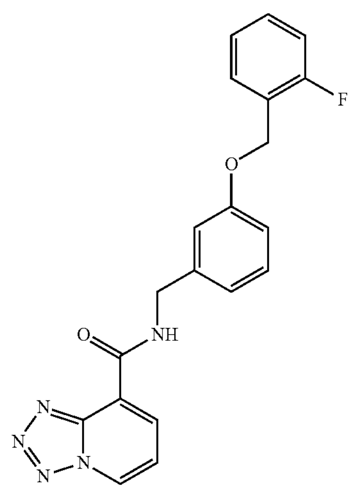 [SMILES: O=C(NCc1cccc(OCc2ccccc2F)c1)c1cccn2nnnc12] | 42 | 10.00 | |
| 38 | 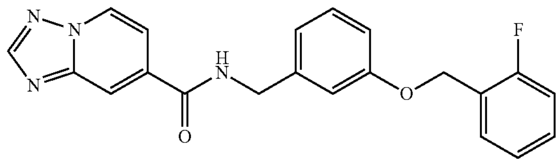 [SMILES: O=C(NCc1cccc(OCc2ccccc2F)c1)c1ccn2ncnc2c1] | 30 | 10.00 | |

TABLE 2-continued
| Number | Structure | hNav1.7 SIS (% inh) | Assay Conc. (uM) | hNav1.7 SIS (IC50 uM) |
|---|---|---|---|---|
| 39 | 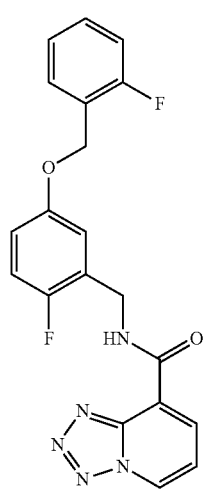 [SMILES: O=C(NCc1cc(OCc2ccccc2F)ccc1F)c1cccn2nnnc12] | 88 | 10.00 | |
| 40 | 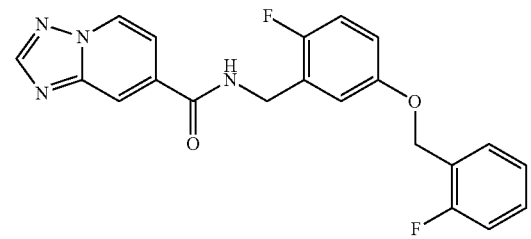 | 42 | 10.00 | |
| 41 | 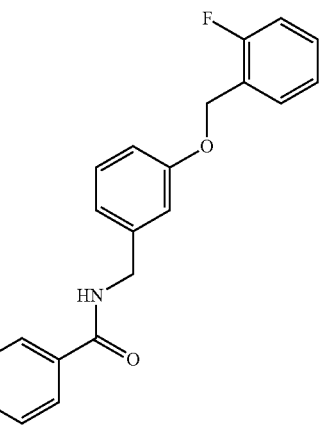 | 59 | 10.00 | |
| 42 | 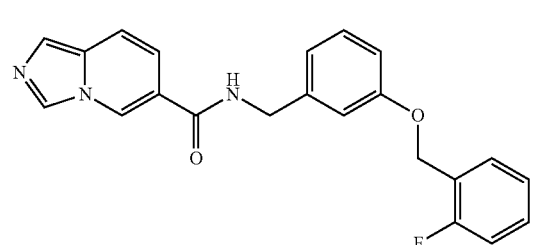 | 45 | 10.00 | |

TABLE 2-continued
| Number | Structure | hNav1.7 SIS (% inh) | Assay Conc. (uM) | hNav1.7 SIS (IC50 uM) |
|---|---|---|---|---|
| 43 | 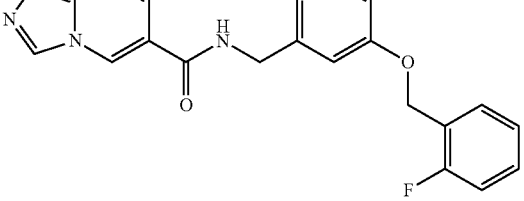 | 55 | 10.00 | |
| 44 | 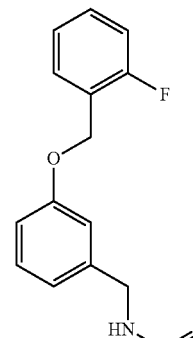 | 92 | 10.00 | |
| 45 | 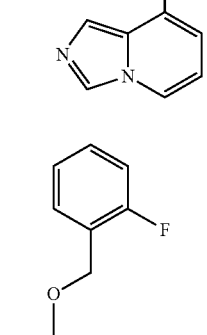 | 66 | 10.00 | |
| 46 | 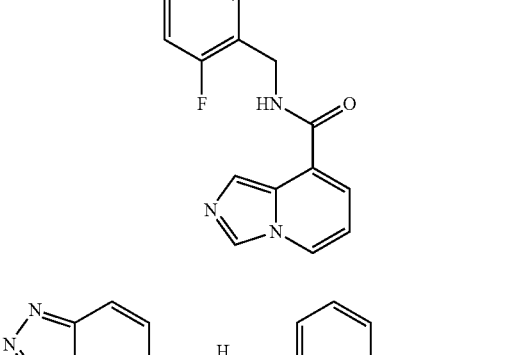 | 49 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 47 | 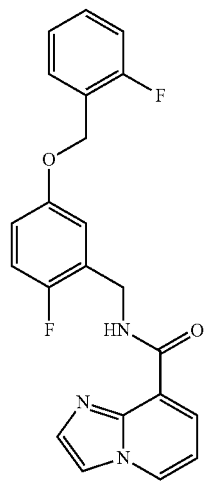 [SMILES: O=C(NCc1cc(OCc2ccccc2F)ccc1F)c1cccn2ccnc12] | 99 | 10.00 | |
| 48 | 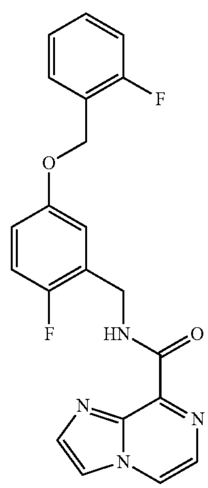 [SMILES: O=C(NCc1cc(OCc2ccccc2F)ccc1F)c1nccn2ccnc12] | 100 | 10.00 | |
| 49 | 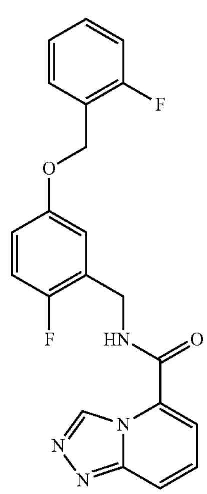 [SMILES: O=C(NCc1cc(OCc2ccccc2F)ccc1F)c1cccc2nncn12] | 38 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 50 | 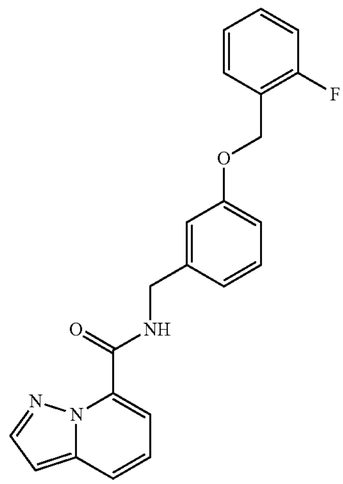 [SMILES: O=C(NCc1cccc(OCc2ccccc2F)c1)c1cccc2ccnn12] | 80 | 10.00 | |
| 51 | 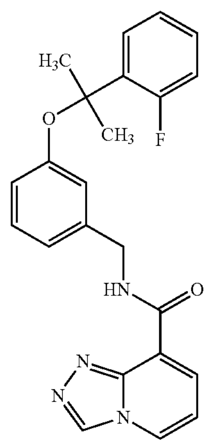 [SMILES: CC(C)(Oc1cccc(CNC(=O)c2cccn3cnnc23)c1)c1ccccc1F] | 36 | 10.00 | |
| 52 | 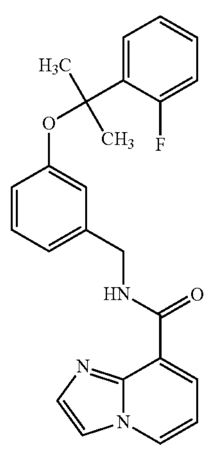 [SMILES: CC(C)(Oc1cccc(CNC(=O)c2cccn3ccnc23)c1)c1ccccc1F] | 83 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 53 | 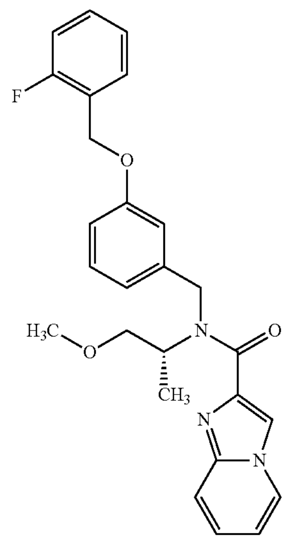 [SMILES: COC[C@@H](C)N(Cc1cccc(OCc2ccccc2F)c1)C(=O)c1cn2ccccc2n1] | 74 | 10.00 | |
| 54 | 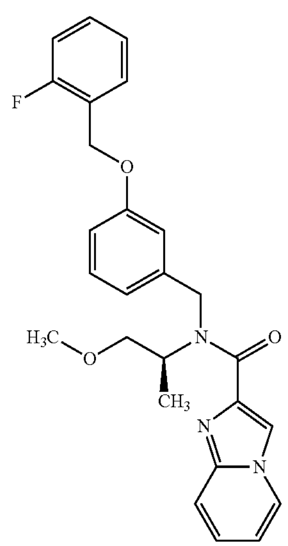 [SMILES: COC[C@H](C)N(Cc1cccc(OCc2ccccc2F)c1)C(=O)c1cn2ccccc2n1] | 55 | 10.00 | |

TABLE 2-continued

| Number | Structure | hNav1.7 SIS (% inh) | Assay Conc. (uM) | hNav1.7 SIS (IC50 uM) |
|--------|-----------|---------------------|------------------|------------------------|
| 55 | *structure* | 49 | 10.00 | |
| 56 | *structure* | | | 2.2 |
| 57 | *structure* | 53 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 58 | 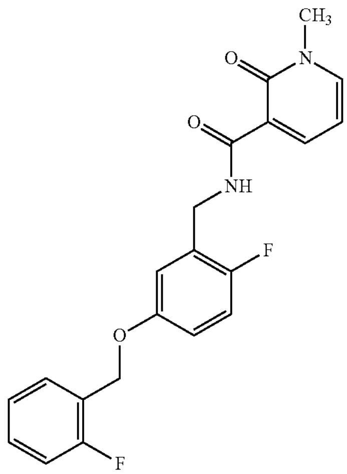 | 52 | 10.00 | |
| 59 | 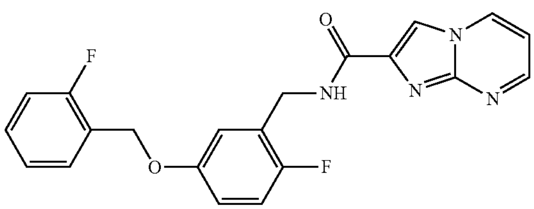 [SMILES: O=C(NCc1cc(OCc2ccccc2F)ccc1F)c1cn2ccccc2n1] | 42 | 10.00 | |
| 60 | 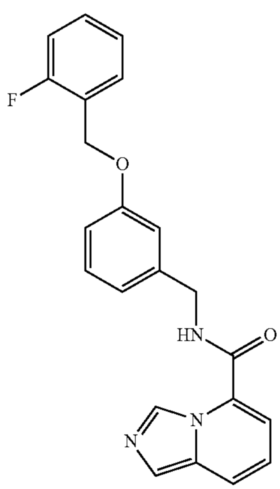 [SMILES: O=C(NCc1cccc(OCc2ccccc2F)c1)c1cccc2cncn12] | 49 | 10.00 | |
| 61 | 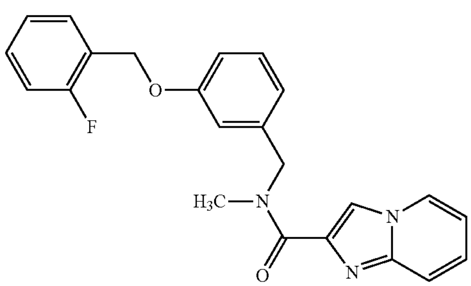 [SMILES: CN(Cc1cccc(OCc2ccccc2F)c1)C(=O)c1cn2ccccc2n1] | | | 1.6 |

TABLE 2-continued

| Number | Structure | hNav1.7 SIS (% inh) | Assay Conc. (uM) | hNav1.7 SIS (IC50 uM) |
| --- | --- | --- | --- | --- |
| 62 | 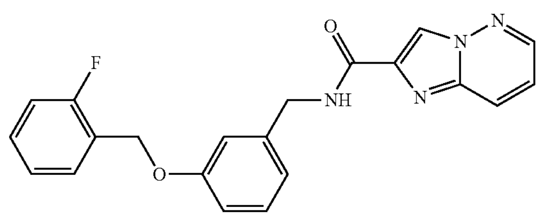 [SMILES: O=C(NCc1cccc(OCc2ccccc2F)c1)c1cn2ncccc2n1] | 50 | 10.00 | |
| 63 | 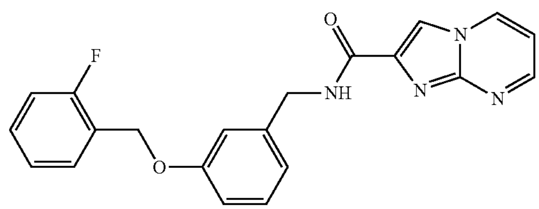 [SMILES: O=C(NCc1cccc(OCc2ccccc2F)c1)c1cn2cccnc2n1] | 42 | 10.00 | |
| 64 | 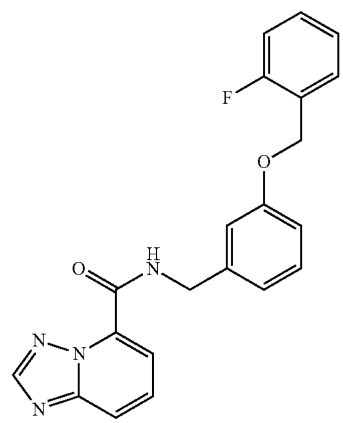 [SMILES: O=C(NCc1cccc(OCc2ccccc2F)c1)c1cccc2ncnn12] | 48 | 10.00 | |
| 65 | 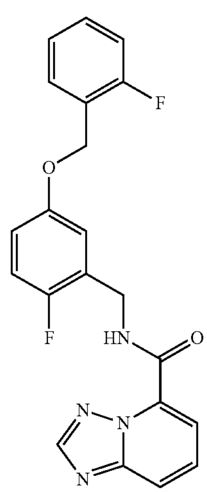 [SMILES: O=C(NCc1cc(OCc2ccccc2F)ccc1F)c1cccc2ncnn12] | | | 10 |

TABLE 2-continued

| Number | Structure | hNav1.7 SIS (% inh) | Assay Conc. (uM) | hNav1.7 SIS (IC50 uM) |
|---|---|---|---|---|
| 66 | 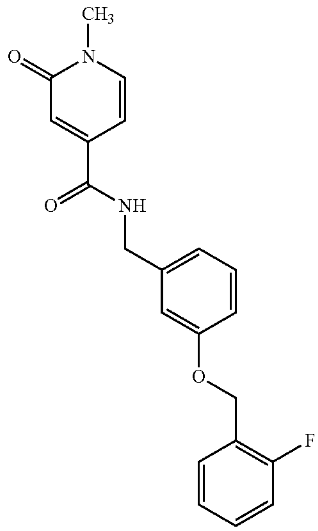 | 30 | 10.00 | |
| 67 | 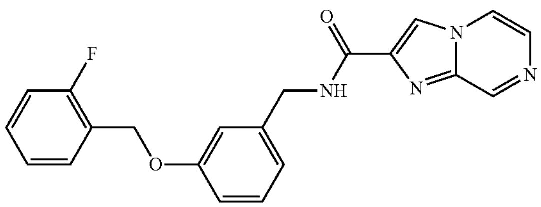 [SMILES: O=C(NCc1cccc(OCc2ccccc2F)c1)c1cn2ccncc2n1] | 34 | 10.00 | |
| 68 | 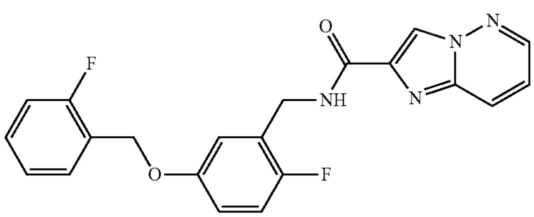 | 53 | 10.00 | |
| 69 | 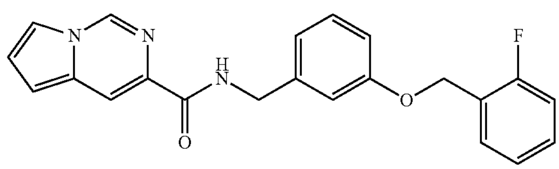 [SMILES: O=C(NCc1cccc(OCc2ccccc2F)c1)c1cc2cccn2cn1] | 92 | 10.00 | |
| 70 | 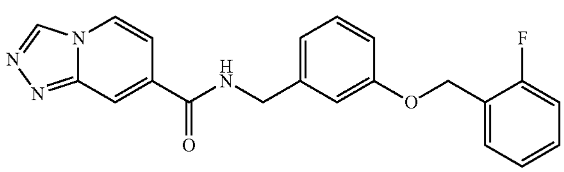 [SMILES: O=C(NCc1cccc(OCc2ccccc2F)c1)c1ccn2cnnc2c1] | 66 | 10.00 | |
| 71 | 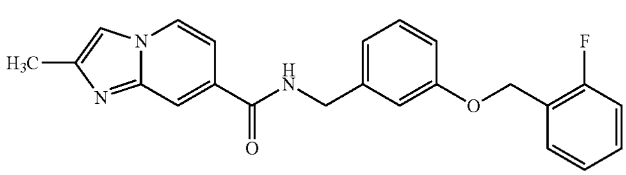 [SMILES: Cc1cn2ccc(C(=O)NCc3cccc(OCc4ccccc4F)c3)cc2n1] | 66 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 72 | 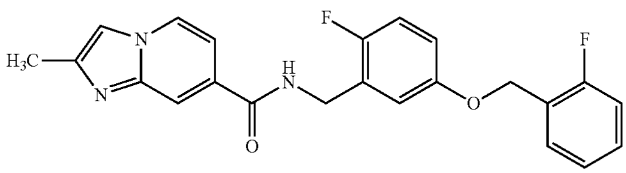 [SMILES: Cc1cn2ccc(C(=O)NCc3cc(OCc4ccccc4F)ccc3F)cc2n1] | 100 | 10.00 | |
| 73 | 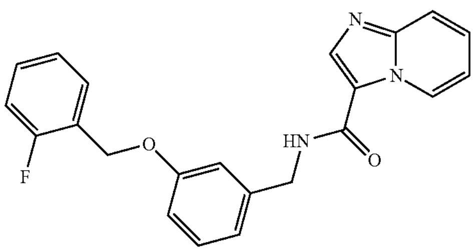 [SMILES: O=C(NCc1cccc(OCc2ccccc2F)c1)c1cnc2ccccn12] | 47 | 10.00 | |
| 74 | 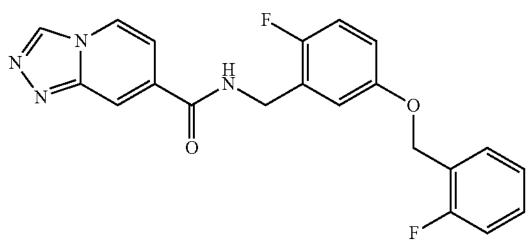 [SMILES: O=C(NCc1cc(OCc2ccccc2F)ccc1F)c1ccn2cnnc2c1] | 58 | 10.00 | |
| 75 | 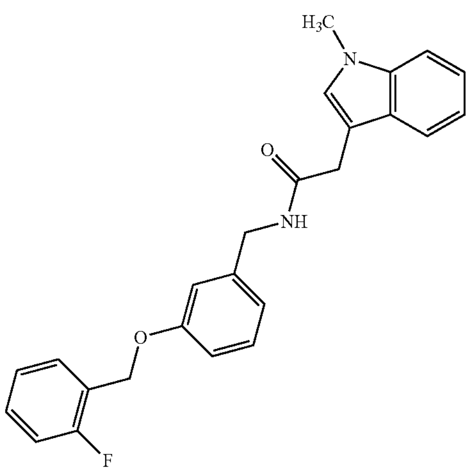 [SMILES: Cn1cc(CC(=O)NCc2cccc(OCc3ccccc3F)c2)c2ccccc21] | 74 | 10.00 | |
| 76 | 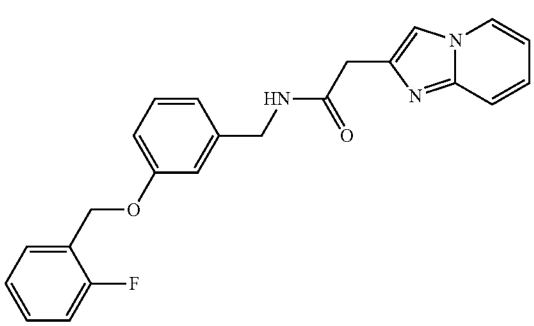 [SMILES: O=C(Cc1cn2ccccc2n1)NCc1cccc(OCc2ccccc2F)c1] | 44 | 10.00 | |

TABLE 2-continued
| Number | Structure | hNav1.7 SIS (% inh) | Assay Conc. (uM) | hNav1.7 SIS (IC50 uM) |
|---|---|---|---|---|
| 77 | 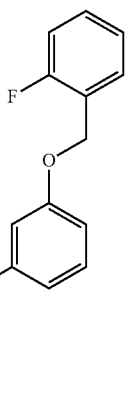 | 70 | 10.00 | |
| 78 | 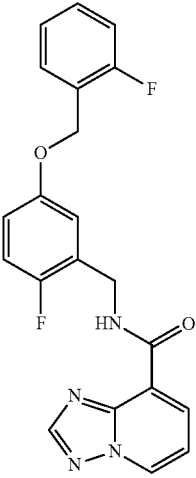 | 83 | 10.00 | |
| 79 | 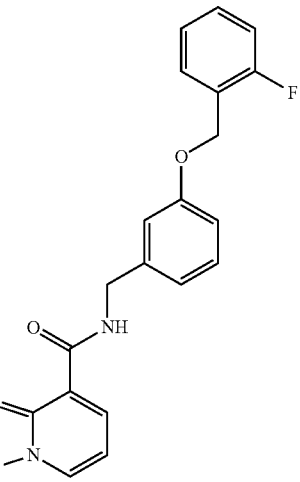 | 42 | 10.00 | |
| 80 | 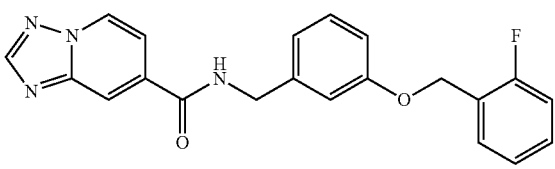 [SMILES: O=C(NCc1cccc(OCc2ccccc2F)c1)c1ccn2ncnc2c1] | 30 | 10.00 | |

TABLE 2-continued
| Number | Structure | hNav1.7 SIS (% inh) | Assay Conc. (uM) | hNav1.7 SIS (IC50 uM) |
|---|---|---|---|---|
| 81 | 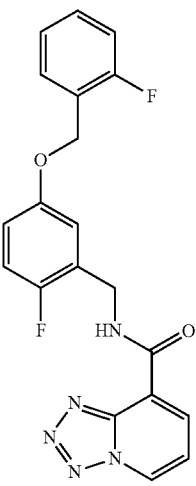 [SMILES: O=C(NCc1cc(OCc2ccccc2F)ccc1F)c1cccn2nnnc12] | 88 | 10.00 | |
| 82 | 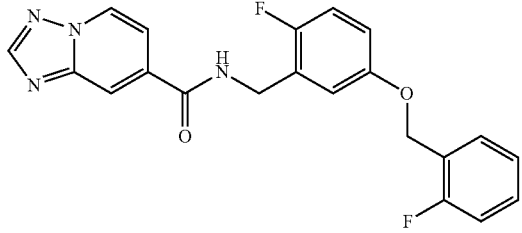 [SMILES: O=C(NCc1cc(OCc2ccccc2F)ccc1F)c1ccn2ncnc2c1] | 42 | 10.00 | |
| 83 | 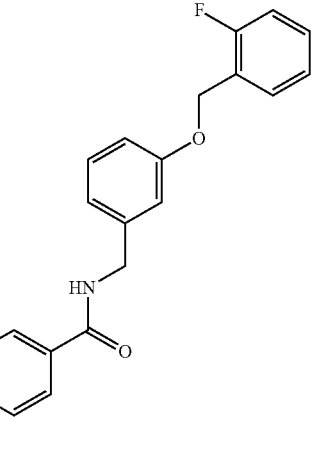 | 59 | 10.00 | |
| 84 | 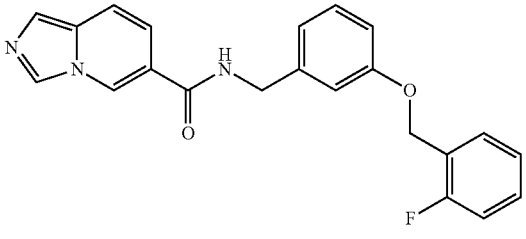 [SMILES: O=C(NCc1cccc(OCc2ccccc2F)c1)c1ccc2cncn2c1] | 45 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 85 | 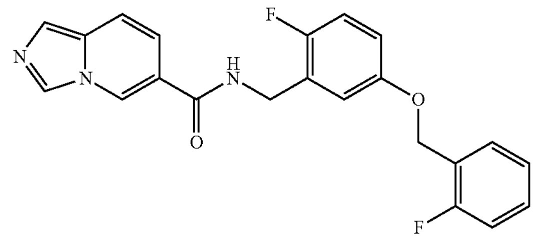 [SMILES: O=C(NCc1cc(OCc2ccccc2F)ccc1F)c1ccc2cncn2c1] | 55 | 10.00 | |
| 86 | 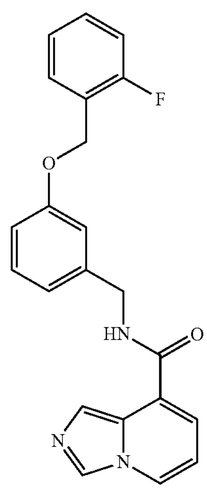 [SMILES: O=C(NCc1cccc(OCc2ccccc2F)c1)c1cccn2cncc12] | 92 | 10.00 | |
| 87 | 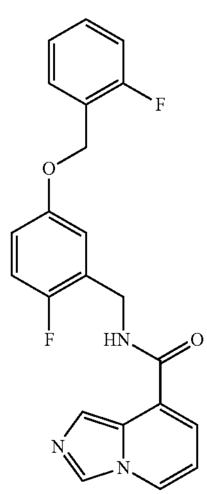 [SMILES: O=C(NCc1cc(OCc2ccccc2F)ccc1F)c1cccn2cncc12] | 66 | 10.00 | |
| 88 | 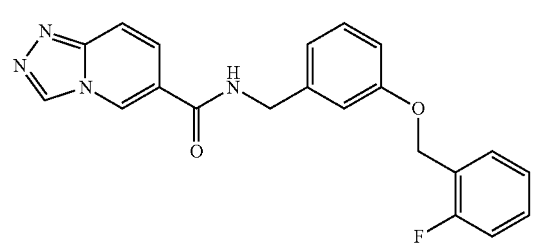 [SMILES: O=C(NCc1cccc(OCc2ccccc2F)c1)c1ccc2nncn2c1] | 49 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 89 | 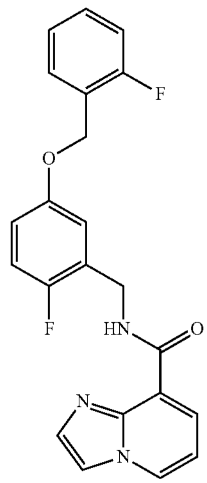 [SMILES: O=C(NCc1cc(OCc2ccccc2F)ccc1F)c1cccn2ccnc12] | 99 | 10.00 | |
| 90 | 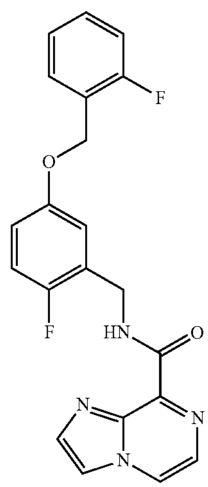 [SMILES: O=C(NCc1cc(OCc2ccccc2F)ccc1F)c1nccn2ccnc12] | 100 | 10.00 | |
| 91 | 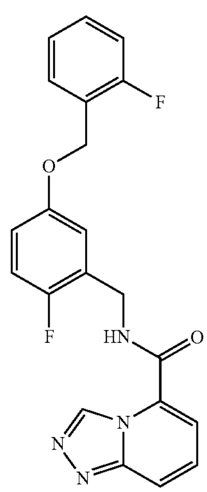 [SMILES: O=C(NCc1cc(OCc2ccccc2F)ccc1F)c1cccc2nncn12] | 38 | 10.00 | |

TABLE 2-continued
| Number | Structure | hNav1.7 SIS (% inh) | Assay Conc. (uM) | hNav1.7 SIS (IC50 uM) |
|---|---|---|---|---|
| 92 | 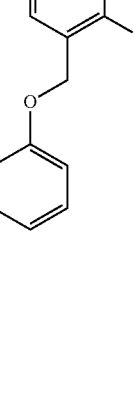 | 80 | 10.00 | |
| 93 | 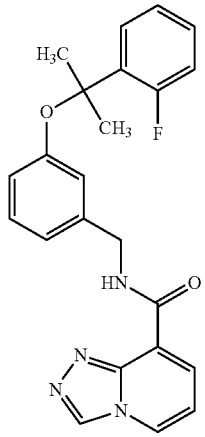 [SMILES: CC(C)(Oc1cccc(CNC(=O)c2cccn3cnnc23)c1)c1ccccc1F] | 36 | 10.00 | |
| 94 | 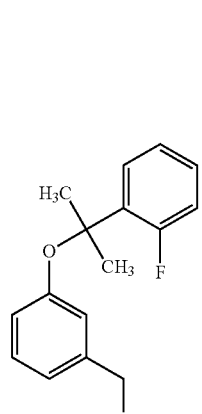 | 83 | 10.00 | |

TABLE 2-continued

| Number | Structure | hNav1.7 SIS (% inh) | Assay Conc. (uM) | hNav1.7 SIS (IC50 uM) |
|---|---|---|---|---|
| 95 | 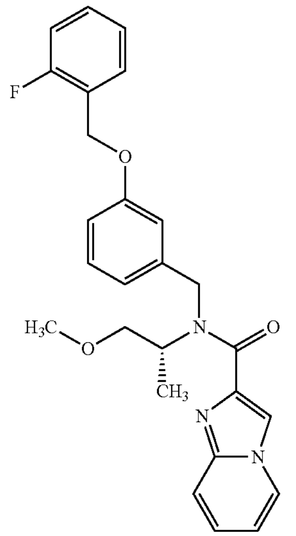 [SMILES: COC[C@@H](C)N(Cc1cccc(OCc2ccccc2F)c1)C(=O)c1cn2ccccc2n1] | 74 | 10.00 | |
| 96 | 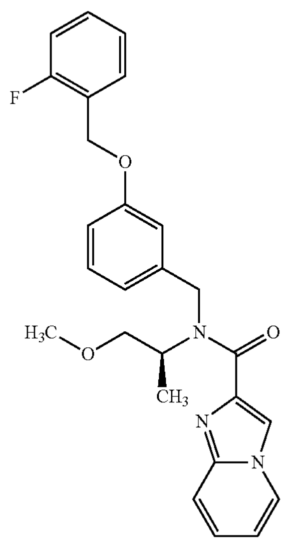 [SMILES: COC[C@H](C)N(Cc1cccc(OCc2ccccc2F)c1)C(=O)c1cn2ccccc2n1] | 55 | 10.00 | |

The claims defining the invention are as follows:

1. A compound of formula (I)

or a salt, stereoisomer, solvate or prodrug thereof, wherein
R is an optionally substituted aryl, optionally substituted heterocycyl or optionally substituted heteroaryl;
$R^1$ is H or an optionally substituted $C_1$-$C_4$ alkyl;
$R^2$, $R^3$, $R^4$ and $R^5$ are independently H or a $C_1$-$C_4$ alkyl or $R^2$ and $R^3$, or $R^4$ and $R^5$ together form a cycloalkyl ring;

Y is selected from

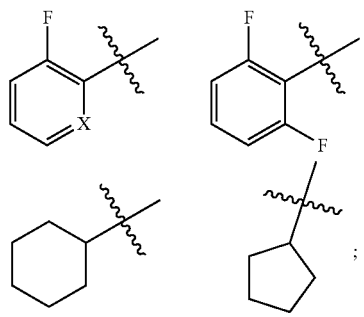

X is CH or N; and
Z is F or $CF_3$.

2. The compound of formula (I) according to claim 1,

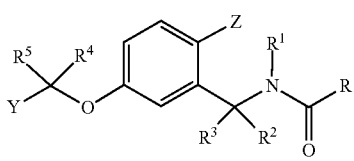
(I)

or a salt, stereoisomer, solvate or prodrug thereof, wherein:
R is an optionally substituted heteroaryl;
$R^1$ is H or an optionally substituted $C_1$-$C_4$ alkyl;
$R^2$, $R^3$, $R^4$ and $R^5$ are independently H or a $C_1$-$C_4$ alkyl, or $R^2$ and $R^3$, or $R^4$ and $R^5$ together form a cycloalkyl ring;
Y is selected from

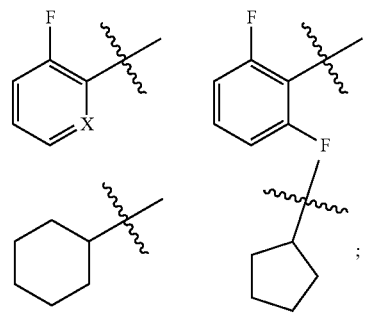

X is CH or N; and
Z is F or $CF_3$.

3. The compound of formula (I) according to claim 1,

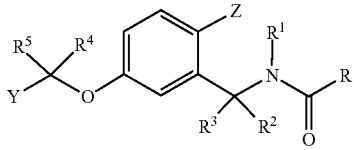
(I)

or a salt, stereoisomer, solvate or prodrug thereof, wherein
R is an optionally substituted 7-12 membered heteroaryl;
$R^1$ is H or an optionally substituted $C_1$-$C_4$ alkyl;
$R^2$, $R^3$, $R^4$ and $R^5$ are independently H or a $C_1$-$C_4$ alkyl, or $R^2$ and $R^3$, or $R^4$ and $R^5$ together form a cycloalkyl ring;
Y is selected from

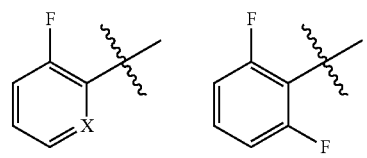

-continued

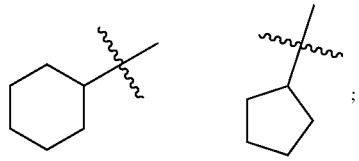

X is CH or N; and
Z is F or $CF_3$.

4. The compound of formula (I) according to claim 1,

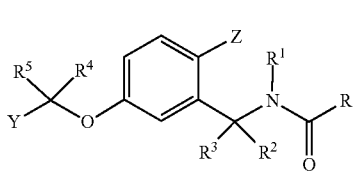
(I)

or a salt, stereoisomer, solvate or prodrug thereof, wherein:
R is an optionally substituted 7-12 membered heteroaryl with 2 or more N atoms;
$R^1$ is H or an optionally substituted $C_1$-$C_4$ alkyl;
$R^2$, $R^3$, $R^4$ and $R^5$ are independently H or a $C_1$-$C_4$ alkyl, or $R^2$ and $R^3$, or $R^4$ and $R^5$ together form a cycloalkyl ring;
Y is selected from

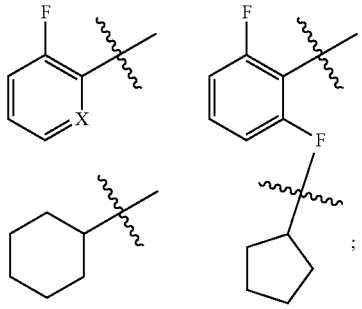

X is CH or N; and
Z is F or $CF_3$.

5. The compound of formula (I) according to claim 1,

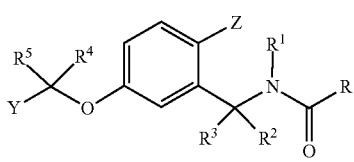
(I)

or a salt, stereoisomer, solvate or prodrug thereof, wherein:
R is an optionally substituted 7-12 membered heteroaryl with 2 nitrogen atoms;
$R^1$ is H or an optionally substituted $C_1$-$C_4$ alkyl;
$R^2$, $R^3$, $R^4$ and $R^5$ are independently H or a $C_1$-$C_4$ alkyl, or $R^2$ and $R^3$, or $R^4$ and $R^5$ together form a cycloalkyl ring;

Y is selected from

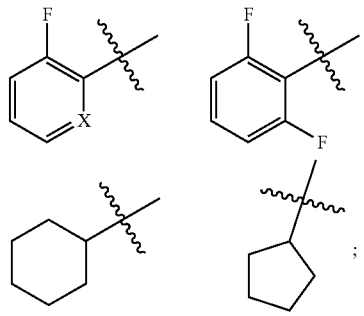

X is CH or N; and

Z is F or CF$_3$.

6. The compound according to claim 1, wherein R$^1$ is H.

7. The compound according to claim 1, wherein R$^2$, R$^3$, R$^4$ and R$^5$ are each H.

8. The compound according to any claim 1, wherein Z is F.

9. The compound according to claim 1, wherein Y is

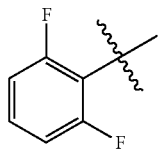

10. The compound according to claim 1, wherein Y is

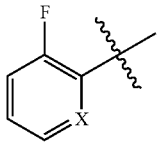

and X is CH or N.

11. The compound according to claim 10, wherein X is CH.

12. The compound according to claim 1, wherein R is selected from one of the following moieties:

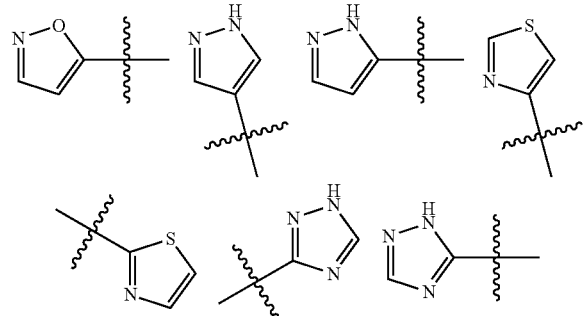

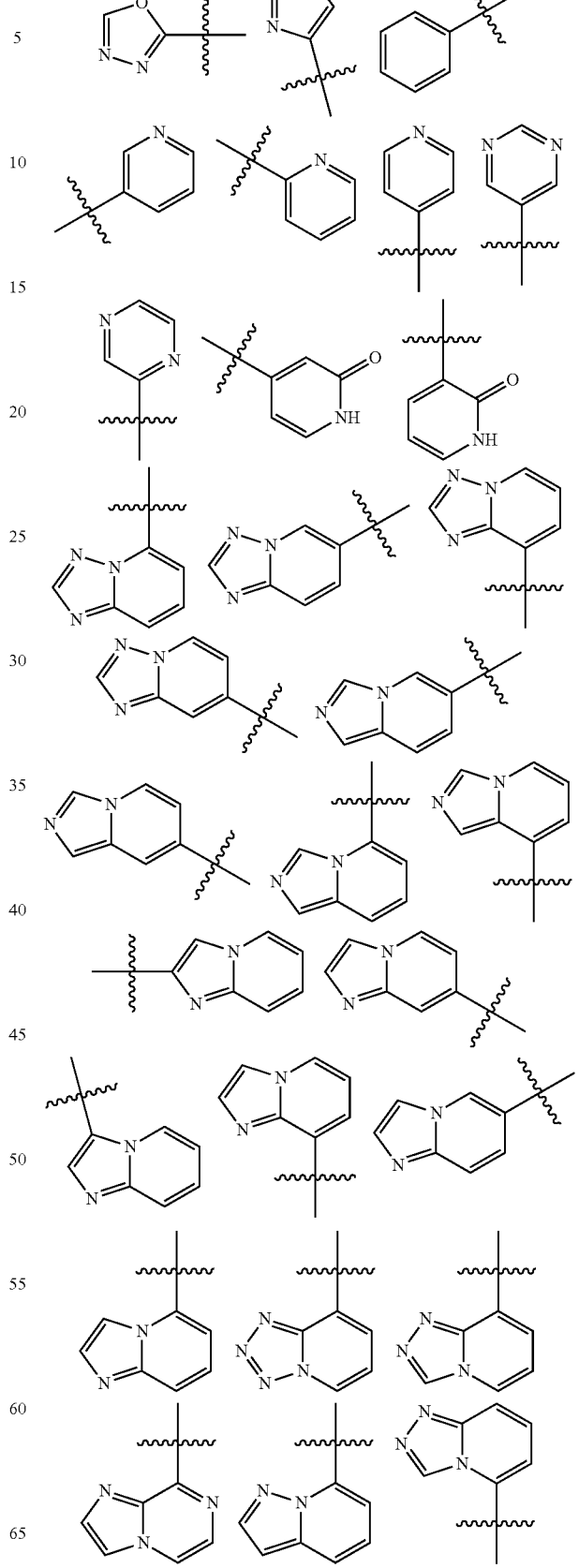

-continued

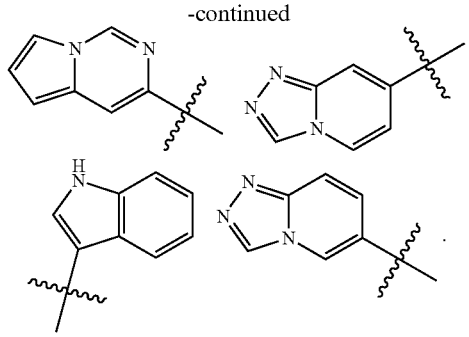

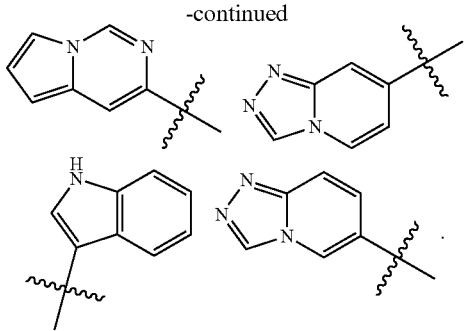

13. The compound according to claim 1, wherein R is selected from one of the following moieties:

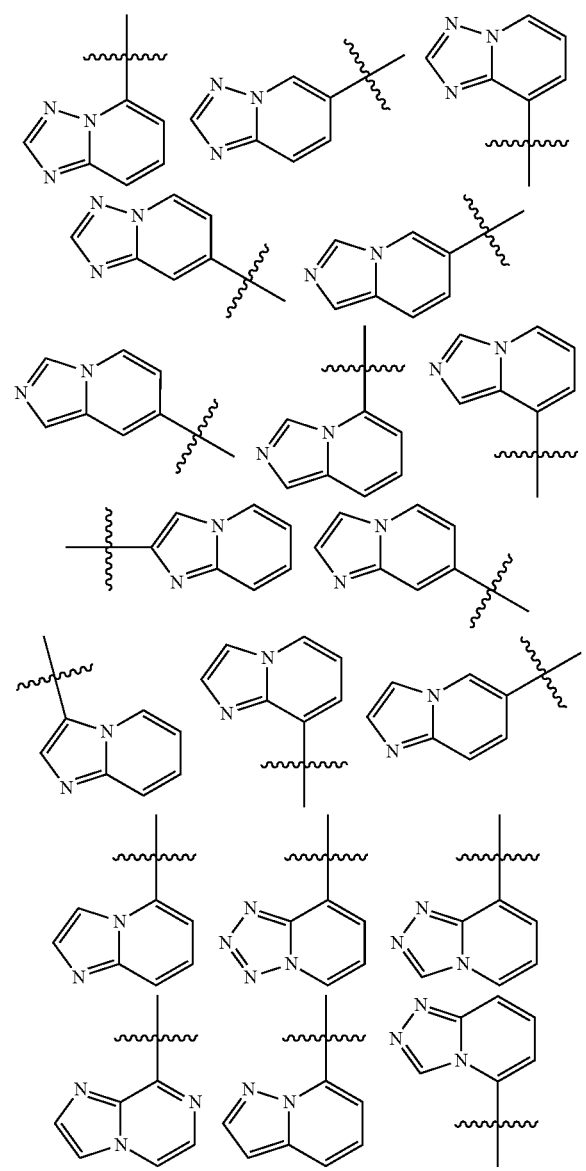

14. A pharmaceutical composition comprising the compound according to claim 1, together with a diluent or carrier adjuvant.

15. A method of manufacturing a medicament for treating pain disorders, said method comprising preparing a compound of formula (I)

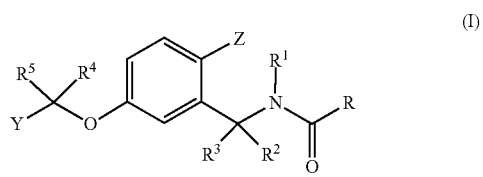

(I)

or a salt, stereoisomer, solvate or prodrug thereof, wherein:

R is an optionally substituted aryl, optionally substituted heterocycyl or optionally substituted heteroaryl;

$R^1$ is H or an optionally substituted $C_1$-$C_4$ alkyl;

$R^2$, $R^3$, $R^4$ and $R^5$ are independently H or a $C_1$-$C_4$ alkyl or $R^2$ and $R^3$, or $R^4$ and $R^5$ together form a cycloalkyl ring;

Y is selected from

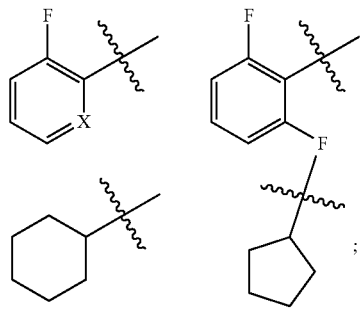

X is CH or N; and

Z is F or $CF_3$.

16. The method according to claim 15, wherein the pain disorder is selected from the group consisting of chronic pain, neuropathic pain, inflammatory pain, and cancer pain.

* * * * *